(12) United States Patent
Aburatani et al.

(10) Patent No.: US 9,920,129 B2
(45) Date of Patent: Mar. 20, 2018

(54) DIAGNOSIS AND TREATMENT OF CANCER USING ANTI-ITM2A ANTIBODY

(71) Applicants: THE UNIVERSITY OF TOKYO, Bunkyo-ku, Tokyo (JP); CHUGAI SEIYAKU KABUSHIKI KAISHA, Kita-ku, Tokyo (JP)

(72) Inventors: Hiroyuki Aburatani, Bunkyo-ku (JP); Shumpei Ishikawa, Bunkyo-ku (JP); Shigeto Kawai, Meguro-ku (JP)

(73) Assignees: THE UNIVERSITY OF TOKYO, Tokyo (JP); CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/142,234

(22) Filed: Apr. 29, 2016

(65) Prior Publication Data

US 2016/0311920 A1    Oct. 27, 2016

Related U.S. Application Data

(62) Division of application No. 14/112,590, filed as application No. PCT/JP2012/002697 on Apr. 18, 2012, now abandoned.

(30) Foreign Application Priority Data

Apr. 18, 2011    (JP) .................................. 2011-092488

(51) Int. Cl.
*C07K 16/30*     (2006.01)
*C07K 16/28*     (2006.01)
*G01N 33/574*    (2006.01)

(52) U.S. Cl.
CPC .......... *C07K 16/3061* (2013.01); *C07K 16/28* (2013.01); *G01N 33/57407* (2013.01); *G01N 33/57426* (2013.01); *C07K 2317/56* (2013.01); *C07K 2317/565* (2013.01); *C07K 2317/73* (2013.01); *C07K 2317/732* (2013.01); *G01N 2800/52* (2013.01)

(58) Field of Classification Search
None
See application file for complete search history.

(56) References Cited

U.S. PATENT DOCUMENTS

| 2007/0071757 A1 | 3/2007 | Yu et al. |
| 2010/0297664 A1 | 11/2010 | Wadhwa et al. |

FOREIGN PATENT DOCUMENTS

| JP | 2004187679 | 7/2004 |
| WO | 2008131298 | 10/2008 |
| WO | 2008137500 | 11/2008 |
| WO | 2008146854 | 12/2008 |
| WO | 2010132659 | 11/2010 |

OTHER PUBLICATIONS

Berger et al. (Cancer Research, 48: 1238-1243, 1988).*
Owen, Leah A. et al., "Identification of Target Genes in Their Native Cellular Context", Cell Cycle, Sep. 15, 2006, No. 5, Issue 18, pp. 2049-2053 (total 6 pages).
Communication dated Aug. 30, 2016 from the Japanese Patent Office in counterpart Application No. 2013-510890.
Miller, et al., "Integrative Meta-Analysis of Differential Gene Expression in Acute Myeloid Leukemia", PLoS ONE, 5(Issue 3):e9466(1-13), (2010).
Communication from the European Patent Office in Counterpart Application No. 12774392.0, dated Jun. 15, 2015.
Plas et al., "In vitro studies Itm2a reveal its involvement in early stages of the chondrogenic differentiation pathway", Biology of the Cell, 96:463-470 (2004).
Kirchner et al., "ITM2A Is Induced during Thymocyte Selection and T cell Activation and Causes Downregulation of CD8 when Overexpressed in CD4+CD8+ Double Positive Thymocytes.", J. Exp. Med., 190(2):217-228 (1999).
Staege et al., "DNA Microarrays Reveal Relationship of Ewing Family Tumors to Both Endothelial and Fetal Neural Crest-Derived Cells and Define Novel Targets.", Cancer Research, 64(22):8213-8221 (2004).
Riggi et al., "EWS-FLI-1 Expression Triggers a Ewing's Sarcoma Initiation Program in Primary Human Mesenchymal Stem Cells", Cancer Res, 68(7):2176-2185 (2008).
Boeuf et al., "Enhanced ITM2A expression inhibits chondrogenic differentiation of mesenchymal stem cells", Differentiation, 78:108-115 (2009).
Deleersnijder et al., "Isolation of Makers for Chondro-osteogenic Differentiation Using cDNA Library Substraction", The Journal of Biological Chemistry, 271(32):19475-19482 (1996).
Rudikoff et al., "Single amino acid substitution altering antigen-binding specificity", Proc. Natl. Acad. Sci. USA, 79(6):1979-1983 (1982).
McCarthy et al., "Altering the fine specificity of an anti-Legionella single chain antibody by a single amino acid insertion", J. Immunol. Methods, 251(1-2): 137-149 (2001).
Stancovski et al., "Mechanistic aspects of the opposing effects of monoclonal antibodies to the ERBB2 receptor on tumor growth", PNAS, 88:8691-8695 (1991).

(Continued)

*Primary Examiner* — Nelson B Moseley, II
(74) *Attorney, Agent, or Firm* — Sughrue Mion, PLLC

(57) ABSTRACT

Disclosed is a monoclonal antibody binding to an ITM2A protein. This antibody is useful in the diagnosis, prevention, and treatment of cancer such as Ewing's sarcoma, T cell leukemia, T cell lymphoma, acute myeloid leukemia, B cell tumor, and multiple myeloma. The present invention also provides a pharmaceutical composition, a cell growth inhibitor, and an anticancer agent containing the antibody as an active ingredient, and a method for treating cancer, a method for predicting the efficacy of cancer treatment, and a method for determining the presence of cancer in a test subject using the antibody.

8 Claims, 9 Drawing Sheets

(56) References Cited

OTHER PUBLICATIONS

Jiang et al., "A Novel Peptide Isolated from a Phage Display Peptide Library with Trastuzumab Can Mimic Antigen Epitope of HER-2", J. Biol. Chem., 280:4656-4662 (2005).

* cited by examiner

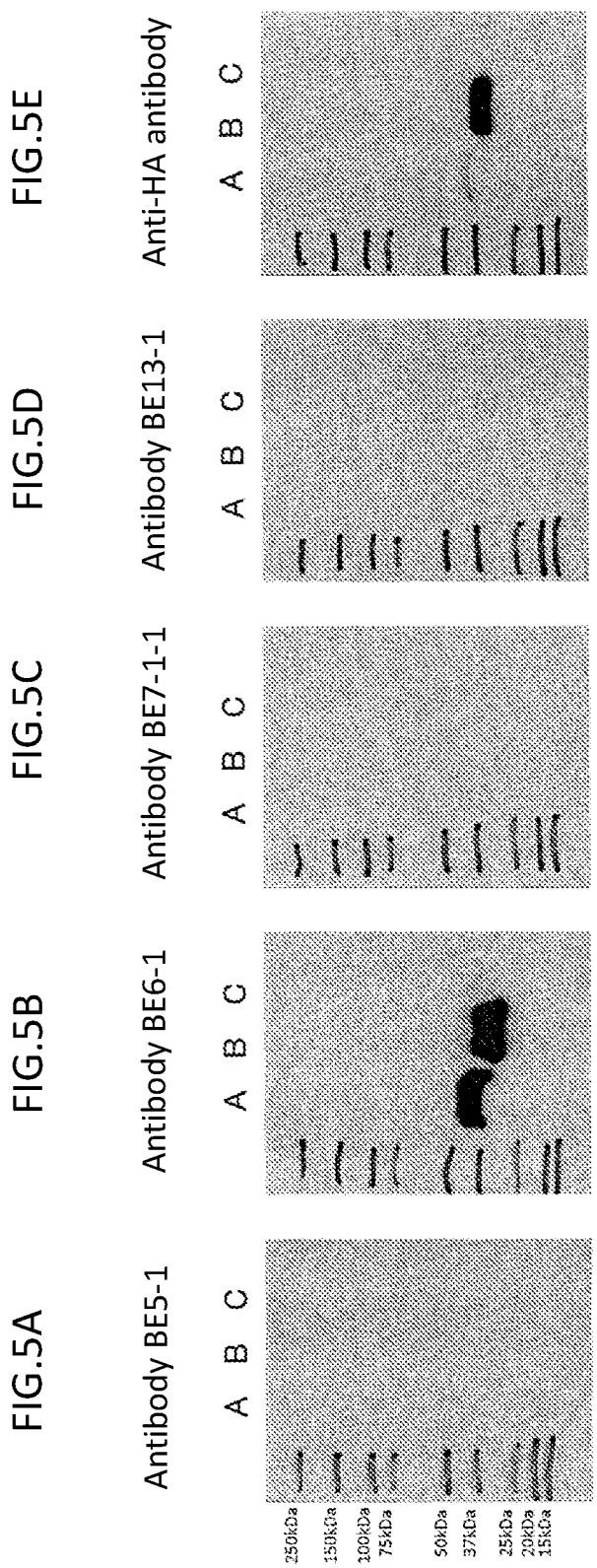

A-673

RD-ES

SK-ES-1

SK-N-MC

CCRF-CEM

Jurkat

MOLT-4

HuT78

KG-1a

TF-1a

——— BE6-1
·········· Mouse IgG1

SEQUENCE LISTING

<160> NUMBER OF SEQ ID NOS: 86

<210> SEQ ID NO 1
<211> LENGTH: 263

```
<212> TYPE: PRT
<213> ORGANISM: homo sapiens

<400> SEQUENCE: 1

Met Val Lys Ile Ala Phe Asn Thr Pro Thr Ala Val Gln Lys Glu Glu
1               5                   10                  15

Ala Arg Gln Asp Val Glu Ala Leu Leu Ser Arg Thr Val Arg Thr Gln
                20                  25                  30

Ile Leu Thr Gly Lys Glu Leu Arg Val Ala Thr Gln Glu Lys Glu Gly
            35                  40                  45

Ser Ser Gly Arg Cys Met Leu Thr Leu Leu Gly Leu Ser Phe Ile Leu
        50                  55                  60

Ala Gly Leu Ile Val Gly Gly Ala Cys Ile Tyr Lys Tyr Phe Met Pro
65                  70                  75                  80

Lys Ser Thr Ile Tyr Arg Gly Glu Met Cys Phe Phe Asp Ser Glu Asp
                85                  90                  95

Pro Ala Asn Ser Leu Arg Gly Gly Glu Pro Asn Phe Leu Pro Val Thr
            100                 105                 110

Glu Glu Ala Asp Ile Arg Glu Asp Asp Asn Ile Ala Ile Ile Asp Val
        115                 120                 125

Pro Val Pro Ser Phe Ser Asp Ser Asp Pro Ala Ala Ile Ile His Asp
130                 135                 140

Phe Glu Lys Gly Met Thr Ala Tyr Leu Asp Leu Leu Leu Gly Asn Cys
145                 150                 155                 160

Tyr Leu Met Pro Leu Asn Thr Ser Ile Val Met Pro Pro Lys Asn Leu
                165                 170                 175

Val Glu Leu Phe Gly Lys Leu Ala Ser Gly Arg Tyr Leu Pro Gln Thr
            180                 185                 190

Tyr Val Val Arg Glu Asp Leu Val Ala Val Glu Ile Arg Asp Val
        195                 200                 205

Ser Asn Leu Gly Ile Phe Ile Tyr Gln Leu Cys Asn Asn Arg Lys Ser
210                 215                 220

Phe Arg Leu Arg Arg Arg Asp Leu Leu Leu Gly Phe Asn Lys Arg Ala
225                 230                 235                 240

Ile Asp Lys Cys Trp Lys Ile Arg His Phe Pro Asn Glu Phe Ile Val
                245                 250                 255

Glu Thr Lys Ile Cys Gln Glu
            260

<210> SEQ ID NO 2
<211> LENGTH: 792
<212> TYPE: DNA
<213> ORGANISM: homo sapiens

<400> SEQUENCE: 2
atggtgaaaa tcgccttcaa taccccctacc gccgtgcaaa aggaggaggc gcggcaagac    60
gtggaggccc tcctgagccg cacggtcaga actcagatac tgaccggcaa ggagctccga   120
gttgccaccc aggaaaaaga gggctcctct gggagatgta tgcttactct cttaggcctt   180
tcattcatct tggcaggact tattgttggt ggagcctgca tttacaagta cttcatgccc   240
aagagcacca tttaccgtgg agagatgtgc ttttttgatt ctgaggatcc tgcaaattcc   300
cttcgtggag gagagcctaa cttcctgcct gtgactgagg aggctgacat tcgtgaggat   360
gacaacattg caatcattga tgtgcctgtc cccagttttct ctgatagtga ccctgcagca   420
attattcatg actttgaaaa gggaatgact gcttacctgg acttgttgct ggggaactgc   480
```

-continued

```
tatctgatgc ccctcaatac ttctattgtt atgcctccaa aaaatctggt agagctcttt    540
ggcaaactgg cgagtggcag atatctgcct caaacttatg tggttcgaga agacctagtt    600
gctgtggagg aaattcgtga tgttagtaac cttggcatct ttatttacca actttgcaat    660
aacagaaagt ccttccgcct tcgtcgcaga gacctcttgc tgggtttcaa caaacgtgcc    720
attgataaat gctggaagat tagacacttc cccaacgaat ttattgttga gaccaagatc    780
tgtcaagagt aa                                                        792

<210> SEQ ID NO 3
<211> LENGTH: 5
<212> TYPE: PRT
<213> ORGANISM: homo sapiens

<400> SEQUENCE: 3

Asp Tyr Arg Met His
1               5

<210> SEQ ID NO 4
<211> LENGTH: 19
<212> TYPE: PRT
<213> ORGANISM: Mus musculus

<400> SEQUENCE: 4

Val Ile Thr Gly Lys Ser Asp Asn Tyr Gly Ala Ser Tyr Ala Glu Ser
1               5                   10                  15

Val Lys Gly

<210> SEQ ID NO 5
<211> LENGTH: 3
<212> TYPE: PRT
<213> ORGANISM: Mus musculus

<400> SEQUENCE: 5

Arg Asp Tyr
1

<210> SEQ ID NO 6
<211> LENGTH: 16
<212> TYPE: PRT
<213> ORGANISM: Mus musculus

<400> SEQUENCE: 6

Arg Ser Ser Lys Ser Leu Leu His Ser Asn Gly Asn Thr Tyr Leu Tyr
1               5                   10                  15

<210> SEQ ID NO 7
<211> LENGTH: 7
<212> TYPE: PRT
<213> ORGANISM: Mus musculus

<400> SEQUENCE: 7

Arg Met Ser Asn Leu Ala Pro
1               5

<210> SEQ ID NO 8
<211> LENGTH: 9
<212> TYPE: PRT
<213> ORGANISM: Mus musculus

<400> SEQUENCE: 8

Met Gln His Leu Glu Tyr Pro Phe Thr
```

<210> SEQ ID NO 9
<211> LENGTH: 5
<212> TYPE: PRT
<213> ORGANISM: Mus musculus

<400> SEQUENCE: 9

Glu Tyr Thr Met His
1               5

<210> SEQ ID NO 10
<211> LENGTH: 17
<212> TYPE: PRT
<213> ORGANISM: Mus musculus

<400> SEQUENCE: 10

Gly Ile Asn Pro Asn Asn Gly Asp Thr Ser Tyr Asn Gln Lys Phe Lys
1               5                   10                  15

Gly

<210> SEQ ID NO 11
<211> LENGTH: 5
<212> TYPE: PRT
<213> ORGANISM: Mus musculus

<400> SEQUENCE: 11

Gly Pro Phe Ala Tyr
1               5

<210> SEQ ID NO 12
<211> LENGTH: 16
<212> TYPE: PRT
<213> ORGANISM: Mus musculus

<400> SEQUENCE: 12

Arg Ser Ser Gln Ser Leu Val His Ser Asn Gly Asn Thr Tyr Phe His
1               5                   10                  15

<210> SEQ ID NO 13
<211> LENGTH: 7
<212> TYPE: PRT
<213> ORGANISM: Mus musculus

<400> SEQUENCE: 13

Lys Val Ser Asn Arg Phe Phe
1               5

<210> SEQ ID NO 14
<211> LENGTH: 9
<212> TYPE: PRT
<213> ORGANISM: Mus musculus

<400> SEQUENCE: 14

Ser Gln Thr Thr His Phe Pro Phe Thr
1               5

<210> SEQ ID NO 15
<211> LENGTH: 5
<212> TYPE: PRT
<213> ORGANISM: Mus musculus

<400> SEQUENCE: 15

Ser Tyr Trp Met His

```
<210> SEQ ID NO 16
<211> LENGTH: 17
<212> TYPE: PRT
<213> ORGANISM: Mus musculus

<400> SEQUENCE: 16

Glu Ile Asp Pro Ser Asp Ser Tyr Asn Asp Tyr Asn Gln Lys Phe Lys
1               5                   10                  15

Gly

<210> SEQ ID NO 17
<211> LENGTH: 5
<212> TYPE: PRT
<213> ORGANISM: Mus musculus

<400> SEQUENCE: 17

Trp Gly Glu Asp Tyr
1               5

<210> SEQ ID NO 18
<211> LENGTH: 16
<212> TYPE: PRT
<213> ORGANISM: Mus musculus

<400> SEQUENCE: 18

Lys Ser Ser Gln Ser Leu Leu Asp Ser Asp Gly Lys Thr Tyr Leu Asn
1               5                   10                  15

<210> SEQ ID NO 19
<211> LENGTH: 7
<212> TYPE: PRT
<213> ORGANISM: Mus musculus

<400> SEQUENCE: 19

Leu Val Ser Lys Leu Asp Ser
1               5

<210> SEQ ID NO 20
<211> LENGTH: 9
<212> TYPE: PRT
<213> ORGANISM: Mus musculus

<400> SEQUENCE: 20

Trp Gln Gly Thr His Phe Pro Arg Thr
1               5

<210> SEQ ID NO 21
<211> LENGTH: 5
<212> TYPE: PRT
<213> ORGANISM: Mus musculus

<400> SEQUENCE: 21

Asp Tyr Tyr Met Lys
1               5

<210> SEQ ID NO 22
<211> LENGTH: 17
<212> TYPE: PRT
<213> ORGANISM: Mus musculus

<400> SEQUENCE: 22

Asp Ile Asn Pro Asn Asn Gly Gly Leu Ser Tyr Asn Gln Lys Phe Lys
```

```
1               5                   10                  15
Gly

<210> SEQ ID NO 23
<211> LENGTH: 5
<212> TYPE: PRT
<213> ORGANISM: Mus musculus

<400> SEQUENCE: 23

Trp Ser Gly Ala Tyr
1               5

<210> SEQ ID NO 24
<211> LENGTH: 16
<212> TYPE: PRT
<213> ORGANISM: Mus musculus

<400> SEQUENCE: 24

Lys Ser Ser Gln Ser Leu Leu Asp Ser Asp Gly Lys Thr Tyr Leu Asn
1               5                   10                  15

<210> SEQ ID NO 25
<211> LENGTH: 7
<212> TYPE: PRT
<213> ORGANISM: Mus musculus

<400> SEQUENCE: 25

Leu Val Ser Lys Leu Asp Ser
1               5

<210> SEQ ID NO 26
<211> LENGTH: 9
<212> TYPE: PRT
<213> ORGANISM: Mus musculus

<400> SEQUENCE: 26

Trp Gln Gly Thr His Phe Pro Trp Thr
1               5

<210> SEQ ID NO 27
<211> LENGTH: 342
<212> TYPE: DNA
<213> ORGANISM: Mus musculus

<400> SEQUENCE: 27
caggtgcagc ttgtagagac cggggggaggc ttggtgaggc ctggaaattc tctgaaactc      60
tcctgtgtta cctcgggatt cactttcagt gactaccgga tgcactggct tcgccagtct     120
ccagggaaga ggctggagtg gattgctgta attacaggca aatctgataa ttatggagca     180
agttatgcag agtctgtgaa aggcagattc actatttcaa gagatgattc aaaaagcagt     240
gtctacctgc agatgaacag attaagagag gaagacactg ccacttatta ttgtagtaga     300
agggactact ggggtcaagg aacctcagtc accgtctcct ca                        342

<210> SEQ ID NO 28
<211> LENGTH: 114
<212> TYPE: PRT
<213> ORGANISM: Mus musculus

<400> SEQUENCE: 28

Gln Val Gln Leu Val Glu Thr Gly Gly Gly Leu Val Arg Pro Gly Asn
1               5                   10                  15
```

Ser Leu Lys Leu Ser Cys Val Thr Ser Gly Phe Thr Phe Ser Asp Tyr
                20                  25                  30

Arg Met His Trp Leu Arg Gln Ser Pro Gly Lys Arg Leu Glu Trp Ile
            35                  40                  45

Ala Val Ile Thr Gly Lys Ser Asp Asn Tyr Gly Ala Ser Tyr Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Arg Leu Arg Glu Asp Thr Ala Thr Tyr
                85                  90                  95

Tyr Cys Ser Arg Arg Asp Tyr Trp Gly Gln Gly Thr Ser Val Thr Val
                100                 105                 110

Ser Ser

<210> SEQ ID NO 29
<211> LENGTH: 336
<212> TYPE: DNA
<213> ORGANISM: Mus musculus

<400> SEQUENCE: 29
gatattgtga tgactcaggc tgcaccctct gtacctgtca ctcctggaga gtcagtatcc      60
atctcctgca ggtctagtaa gagtctcctg catagtaatg gcaacactta cttgtattgg    120
ttcctgcaga ggccaggcca gtctcctcag ctcctgatat atcggatgtc caaccttgcc    180
ccaggagtcc cagacaggtt cagtggcagt gggtcaggaa ctgctttcac actgagaatc    240
agtagagtgg aggctgagga tgtgggtgtt tattactgta tgcaacatct cgaatatcct    300
ttcacgttcg gtgctgggac caagctggag ctgaaa                              336

<210> SEQ ID NO 30
<211> LENGTH: 112
<212> TYPE: PRT
<213> ORGANISM: Mus musculus

<400> SEQUENCE: 30

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Pro Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
                100                 105                 110

<210> SEQ ID NO 31
<211> LENGTH: 342
<212> TYPE: DNA
<213> ORGANISM: Mus musculus

<400> SEQUENCE: 31
gaggtccagt tgcaacagtc tggacctgaa ctggtgaagc ctggggcttc agtgaagata      60

```
tcctgcaaga cttctggata cacattcact gaatacacca tgcactgggt gaagcagagc    120
catggaaaga gccttgagtg gattggaggt attaatccta acaatggtga tactagctac    180
aaccagaagt tcaagggcaa ggccacattg actgtagaca agtcctccat cacagcctac    240
atggagctcc gcagcctgac atctgaggat tctgcagtct attactgtgc aagaggcccg    300
tttgcttact ggggccaggg gactctggtc actgtctcta ca                       342
```

<210> SEQ ID NO 32
<211> LENGTH: 114
<212> TYPE: PRT
<213> ORGANISM: Mus musculus

<400> SEQUENCE: 32

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Ser His Gly Lys Ser Leu Glu Trp Ile
            35                  40                  45

Gly Gly Ile Asn Pro Asn Asn Gly Asp Thr Ser Tyr Asn Gln Lys Phe
        50                  55                  60

Lys Gly Lys Ala Thr Leu Thr Val Asp Lys Ser Ser Ile Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Pro Phe Ala Tyr Trp Gly Gln Gly Thr Leu Val Thr Val
            100                 105                 110

Ser Thr

<210> SEQ ID NO 33
<211> LENGTH: 336
<212> TYPE: DNA
<213> ORGANISM: Mus musculus

<400> SEQUENCE: 33

```
gatgttgtga tgacccaaac tccactctcc ctgcctgtca gtcttggaga tcaagcctcc    60
atctcttgca gatctagtca gagccttgta cacagtaatg aaacacctta cttccattgg    120
tacctgcaga agccaggcca gtctccaaag ttcctgatct acaaagtttc caaccgattt    180
tttggggtcc cagacaggtt cagtggcagt ggatcaggga cagatttcac actcaagatc    240
agcagagtgg aggctgagga tctgggagtt tatttctgct ctcaaactac acattttcca    300
ttcacgttcg gctcggggac aaagttggaa ataaaa                              336
```

<210> SEQ ID NO 34
<211> LENGTH: 112
<212> TYPE: PRT
<213> ORGANISM: Mus musculus

<400> SEQUENCE: 34

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Phe His Trp Tyr Leu Gln Lys Pro Gly Gln Ser
            35                  40                  45

Pro Lys Phe Leu Ile Tyr Lys Val Ser Asn Arg Phe Phe Gly Val Pro

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Phe Pro Phe Thr Phe Gly Ser Gly Thr Lys Leu Glu Ile Lys
            100                 105                 110
```

<210> SEQ ID NO 35
<211> LENGTH: 342
<212> TYPE: DNA
<213> ORGANISM: Mus musculus

<400> SEQUENCE: 35

```
caggtccaac tgcagcagcc tggggctgaa cttgtgaaac ctggggcttc agtgaagctg      60
tcctgcaagg cttctggcta caccttcacc agctactgga tgcactgggt gaagcagagg     120
cctggacaag gccttgagtg gatcggagag attgatcctt ctgatagcta taatgactac     180
aatcaaaagt tcaagggcaa ggccacattg actgtagaca atcctccag cacagcctac      240
atgcagctca gcagcctgac atctgaggac tctgcggtct attactgtgc aagatggggg     300
gaggactact ggggccaagg caccactctc acagtctcct ca                        342
```

<210> SEQ ID NO 36
<211> LENGTH: 114
<212> TYPE: PRT
<213> ORGANISM: Mus musculus

<400> SEQUENCE: 36

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asp Pro Ser Asp Ser Tyr Asn Asp Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Gly Glu Asp Tyr Trp Gly Gln Gly Thr Thr Leu Thr Val
            100                 105                 110

Ser Ser
```

<210> SEQ ID NO 37
<211> LENGTH: 336
<212> TYPE: DNA
<213> ORGANISM: Mus musculus

<400> SEQUENCE: 37

```
gatgttgtga tgacccagac tccactcact ttgtcggtta ccattggaca accagcctcc      60
atctcttgca agtcaagtca gagcctctta gatagtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acattttcct     300
```

```
cggacgttcg gtggaggcac aagctggaa atcaaa                                    336
```

```
<210> SEQ ID NO 38
<211> LENGTH: 112
<212> TYPE: PRT
<213> ORGANISM: Mus musculus

<400> SEQUENCE: 38
```

| | | | | | | | | | | | | | | |
|---|---|---|---|---|---|---|---|---|---|---|---|---|---|---|
|Asp|Val|Val|Met|Thr|Gln|Thr|Pro|Leu|Thr|Leu|Ser|Val|Thr|Ile|Gly|
|1| | | |5| | | | |10| | | | |15|

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

```
<210> SEQ ID NO 39
<211> LENGTH: 342
<212> TYPE: DNA
<213> ORGANISM: Mus musculus

<400> SEQUENCE: 39
```

```
gaggtccagc tgcaacaatc tggacctgag ctggtgaagc ctggggcttc agtgaggatg    60
tcctgtaagg cttctggata cacattcact gactactaca tgaagtgggt gaagcagagt   120
catggaaaga gccttgagtg gattggagat attaatccta acaatggtgg tcttagttac   180
aaccagaagt tcaagggcaa ggccacattg actgtagaca atcctccag cacagcctac    240 atgcagctcg ccagcctgac atctgaggac tctgcagtct attactgtgc aatatggtcc   300
ggggcttact ggggccaagg gactctggtc actgtctctg ca                      342
```

```
<210> SEQ ID NO 40
<211> LENGTH: 114
<212> TYPE: PRT
<213> ORGANISM: Mus musculus

<400> SEQUENCE: 40
```

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Asn Pro Asn Asn Gly Gly Leu Ser Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ala Ser Leu Thr Ser Glu Asp Ser Ala Val Tyr Tyr Cys
                85                  90                  95

Ala Ile Trp Ser Gly Ala Tyr Trp Gly Gln Gly Thr Leu Val Thr Val

<210> SEQ ID NO 41
<211> LENGTH: 336
<212> TYPE: DNA
<213> ORGANISM: Mus musculus

<400> SEQUENCE: 41

```
gatgttgtga tgacccagac tccactcact ttgtcggtta ccattggaca accagcctcc      60
atctcttgca gtcaagtca gagcctctta gatagtgatg aaagacata tttgaattgg       120
ttgttacaga ggccaggcca gtctccaaag cgcctaatct atctggtgtc taaactggac     180
tctggagtcc ctgacaggtt cactggcagt ggatcaggga cagatttcac actgaaaatc    240
agcagagtgg aggctgagga tttgggagtt tattattgct ggcaaggtac acattttccg    300
tggacgttcg gtggaggcac caagctggaa atcaaa                               336
```

<210> SEQ ID NO 42
<211> LENGTH: 112
<212> TYPE: PRT
<213> ORGANISM: Mus musculus

<400> SEQUENCE: 42

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110
```

<210> SEQ ID NO 43
<211> LENGTH: 26
<212> TYPE: DNA
<213> ORGANISM: Artificial Sequence
<220> FEATURE:
<223> OTHER INFORMATION: PCR primer

<400> SEQUENCE: 43

```
atggtgaaaa tcgccttcaa tacccc                                           26
```

<210> SEQ ID NO 44
<211> LENGTH: 27
<212> TYPE: DNA
<213> ORGANISM: Artificial Sequence
<220> FEATURE:
<223> OTHER INFORMATION: PCR primer

<400> SEQUENCE: 44

```
ttactcttga cagatcttgg tctcaac                                          27
```

<210> SEQ ID NO 45

```
<211> LENGTH: 43
<212> TYPE: DNA
<213> ORGANISM: Artificial Sequence
<220> FEATURE:
<223> OTHER INFORMATION: PCR primer

<400> SEQUENCE: 45
ggcccagccg gccatggcgt acaagtactt catgcccaag agc              43

<210> SEQ ID NO 46
<211> LENGTH: 30
<212> TYPE: DNA
<213> ORGANISM: Artificial Sequence
<220> FEATURE:
<223> OTHER INFORMATION: PCR primer

<400> SEQUENCE: 46
gcggccgctt actcttgaca gatcttggtc                             30

<210> SEQ ID NO 47
<211> LENGTH: 648
<212> TYPE: DNA
<213> ORGANISM: Artificial Sequence
<220> FEATURE:
<223> OTHER INFORMATION: pMCN2i_mIL3ss-ITM2Aoutside insert

<400> SEQUENCE: 47
atggttcttg ccagctctac caccagcatc cacaccatgc tgctcctgct cctgatgctg     60
gcccagccgg ccatggcgta caagtacttc atgcccaaga gcaccattta ccgtggagag    120
atgtgctttt ttgattctga ggatcctgca aattcccttc gtggaggaga gcctaacttc    180
ctgcctgtga ctgaggaggc tgacattcgt gaggatgaca acattgcaat cattgatgtg    240
cctgtcccca gtttctctga tagtgaccct gcagcaatta ttcatgactt tgaaaaggga    300
atgactgctt acctggactt gttgctgggg aactgctatc tgatgcccct caatacttct    360
attgttatgc ctccaaaaaa tctggtagag ctctttggca aactggcgag tggcagatat    420
ctgcctcaaa cttatgtggt tcgagaagac ctagttgctg tggaggaaat tcgtgatgtt    480
agtaaccttg gcatctttat ttaccaactt tgcaataaca gaaagtcctt ccgccttcgt    540
cgcagagacc tcttgctggg tttcaacaaa cgtgccattg ataaatgctg gaagattaga    600
cacttcccca acgaatttat tgttgagacc aagatctgtc aagagtaa              648

<210> SEQ ID NO 48
<211> LENGTH: 215
<212> TYPE: PRT
<213> ORGANISM: Artificial Sequence
<220> FEATURE:
<223> OTHER INFORMATION: pMCN2i_mIL3ss-ITM2Aoutside insert

<400> SEQUENCE: 48

Met Val Leu Ala Ser Ser Thr Thr Ser Ile His Thr Met Leu Leu Leu
1               5                   10                  15

Leu Leu Met Leu Ala Gln Pro Ala Met Ala Tyr Lys Tyr Phe Met Pro
            20                  25                  30

Lys Ser Thr Ile Tyr Arg Gly Glu Met Cys Phe Phe Asp Ser Glu Asp
        35                  40                  45

Pro Ala Asn Ser Leu Arg Gly Gly Glu Pro Asn Phe Leu Pro Val Thr
    50                  55                  60

Glu Glu Ala Asp Ile Arg Glu Asp Asp Asn Ile Ala Ile Ile Asp Val
65                  70                  75                  80
```

```
Pro Val Pro Ser Phe Ser Asp Ser Asp Pro Ala Ala Ile Ile His Asp
                85                  90                  95

Phe Glu Lys Gly Met Thr Ala Tyr Leu Asp Leu Leu Leu Gly Asn Cys
            100                 105                 110

Tyr Leu Met Pro Leu Asn Thr Ser Ile Val Met Pro Pro Lys Asn Leu
        115                 120                 125

Val Glu Leu Phe Gly Lys Leu Ala Ser Gly Arg Tyr Leu Pro Gln Thr
    130                 135                 140

Tyr Val Val Arg Glu Asp Leu Val Ala Val Glu Ile Arg Asp Val
145                 150                 155                 160

Ser Asn Leu Gly Ile Phe Ile Tyr Gln Leu Cys Asn Asn Arg Lys Ser
                165                 170                 175

Phe Arg Leu Arg Arg Arg Asp Leu Leu Leu Gly Phe Asn Lys Arg Ala
            180                 185                 190

Ile Asp Lys Cys Trp Lys Ile Arg His Phe Pro Asn Glu Phe Ile Val
        195                 200                 205

Glu Thr Lys Ile Cys Gln Glu
    210                 215

<210> SEQ ID NO 49
<211> LENGTH: 42
<212> TYPE: DNA
<213> ORGANISM: Artificial Sequence
<220> FEATURE:
<223> OTHER INFORMATION: PCR primer

<400> SEQUENCE: 49
ctggcccagc cggccatggc gtacaagtac ttcatgccca ag                    42

<210> SEQ ID NO 50
<211> LENGTH: 38
<212> TYPE: DNA
<213> ORGANISM: Artificial Sequence
<220> FEATURE:
<223> OTHER INFORMATION: PCR primer

<400> SEQUENCE: 50
gtcggtccgc gaggttcctc ttgacagatc ttggtctc                         38

<210> SEQ ID NO 51
<211> LENGTH: 1347
<212> TYPE: DNA
<213> ORGANISM: Artificial Sequence
<220> FEATURE:
<223> OTHER INFORMATION: pMCN2i_mIL3ss-ITM2Aoutside-Fc insert

<400> SEQUENCE: 51
atggttcttg ccagctctac caccagcatc cacaccatgc tgctcctgct cctgatgctg     60
gcccagccgg ccatggcgta caagtacttc atgcccaaga gcaccattta ccgtggagag    120
atgtgctttt tgattctga ggatcctgca aattcccttc gtggaggaga gcctaacttc    180
ctgcctgtga ctgaggaggc tgacattcgt gaggatgaca acattgcaat cattgatgtg    240
cctgtcccca gtttctctga tagtgaccct gcagcaatta ttcatgactt tgaaaaggga    300
atgactgctt acctggactt gttgctgggg aactgctatc tgatgcccct caatacttct    360
attgttatgc ctccaaaaaa tctggtagag ctctttggca aactggcgag tggcagatat    420
ctgcctcaaa cttatgtggt tcgagaagac tagttgctg tggaggaaat tcgtgatgtt    480
agtaaccttg gcatctttat ttaccaactt tgcaataaca gaaagtcctt ccgccttcgt    540
```

```
cgcagagacc tcttgctggg tttcaacaaa cgtgccattg ataaatgctg gaagattaga      600
cacttcccca acgaatttat tgttgagacc aagatctgtc aagaggaacc tcgcggaccg      660
acaatcaagc cctgtcctcc atgcaaatgc ccagcaccta acctcttggg tggaccatcc      720
gtcttcatct ccctccaaa gatcaaggat gtactcatga tctccctgag ccccatagtc       780
acatgtgtgg tggtggatgt gagcgaggat gacccagatg tccagatcag ctggtttgtg      840
aacaacgtgg aagtacacac agctcagaca caaaccccata gagaggatta caacagtact    900
ctccgggtgg tcagtgccct ccccatccag caccaggact ggatgagtgg caaggagttc      960
aaatgcaagg tcaacaacaa agacctgcca gcgcccatcg agagaaccat ctcaaaaccc    1020
aaagggtcag taagagctcc acaggtatat gtcttgcctc caccagaaga agagatgact    1080
aagaaacagg tcactctgac ctgcatggtc acagacttca tgcctgaaga catttacgtg    1140
gagtggacca acaacgggaa aacagagcta aactacaaga cactgaacc agtcctggac      1200 tctgatggtt cttacttcat gtacagcaag ctgagagtgg aaaagaagaa ctgggtggaa    1260
agaaatagct actcctgttc agtggtccac gagggtctgc acaatcacca cacgactaag    1320
agcttctccc ggactccggg taaatga                                         1347
```

<210> SEQ ID NO 52
<211> LENGTH: 448
<212> TYPE: PRT
<213> ORGANISM: Artificial Sequence
<220> FEATURE:
<223> OTHER INFORMATION: pMCN2i_mIL3ss-ITM2Aoutside-Fc insert

<400> SEQUENCE: 52

```
Met Val Leu Ala Ser Ser Thr Thr Ser Ile His Thr Met Leu Leu Leu
1               5                   10                  15

Leu Leu Met Leu Ala Gln Pro Ala Met Ala Tyr Lys Tyr Phe Met Pro
            20                  25                  30

Lys Ser Thr Ile Tyr Arg Gly Glu Met Cys Phe Phe Asp Ser Glu Asp
        35                  40                  45

Pro Ala Asn Ser Leu Arg Gly Gly Glu Pro Asn Phe Leu Pro Val Thr
    50                  55                  60

Glu Glu Ala Asp Ile Arg Glu Asp Asp Asn Ile Ala Ile Ile Asp Val
65                  70                  75                  80

Pro Val Pro Ser Phe Ser Asp Ser Asp Pro Ala Ala Ile Ile His Asp
                85                  90                  95

Phe Glu Lys Gly Met Thr Ala Tyr Leu Asp Leu Leu Leu Gly Asn Cys
            100                 105                 110

Tyr Leu Met Pro Leu Asn Thr Ser Ile Val Met Pro Pro Lys Asn Leu
        115                 120                 125

Val Glu Leu Phe Gly Lys Leu Ala Ser Gly Arg Tyr Leu Pro Gln Thr
    130                 135                 140

Tyr Val Val Arg Glu Asp Leu Val Ala Val Glu Ile Arg Asp Val
145                 150                 155                 160

Ser Asn Leu Gly Ile Phe Ile Tyr Gln Leu Cys Asn Asn Arg Lys Ser
                165                 170                 175

Phe Arg Leu Arg Arg Arg Asp Leu Leu Leu Gly Phe Asn Lys Arg Ala
            180                 185                 190

Ile Asp Lys Cys Trp Lys Ile Arg His Phe Pro Asn Glu Phe Ile Val
        195                 200                 205

Glu Thr Lys Ile Cys Gln Glu Glu Pro Arg Gly Pro Thr Ile Lys Pro
    210                 215                 220
```

Cys Pro Pro Cys Lys Cys Pro Ala Pro Asn Leu Leu Gly Gly Pro Ser
225                 230                 235                 240

Val Phe Ile Phe Pro Lys Ile Lys Asp Val Leu Met Ile Ser Leu
            245                 250                 255

Ser Pro Ile Val Thr Cys Val Val Val Asp Val Ser Glu Asp Pro
        260                 265                 270

Asp Val Gln Ile Ser Trp Phe Val Asn Asn Val Glu Val His Thr Ala
            275                 280                 285

Gln Thr Gln Thr His Arg Glu Asp Tyr Asn Ser Thr Leu Arg Val Val
        290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445

<210> SEQ ID NO 53
<211> LENGTH: 35
<212> TYPE: DNA
<213> ORGANISM: Artificial Sequence
<220> FEATURE:
<223> OTHER INFORMATION: PCR primer

<400> SEQUENCE: 53
gaattcacca tggtgaaaat cgccttcaat acccc                        35

<210> SEQ ID NO 54
<211> LENGTH: 62
<212> TYPE: DNA
<213> ORGANISM: Artificial Sequence
<220> FEATURE:
<223> OTHER INFORMATION: PCR primer

<400> SEQUENCE: 54
gcggccgctt aagcgtaatc tggaacatcg tatgggtact cttgacagat cttggtctca    60
ac                                                                  62

<210> SEQ ID NO 55
<211> LENGTH: 819
<212> TYPE: DNA
<213> ORGANISM: Artificial Sequence
<220> FEATURE:
<223> OTHER INFORMATION: pMCN2i_ITM2A-HA insert

<400> SEQUENCE: 55

```
atggtgaaaa tcgccttcaa taccctacc gccgtgcaaa aggaggaggc gcggcaagac    60
gtggaggccc tcctgagccg cacggtcaga actcagatac tgaccggcaa ggagctccga   120
gttgccaccc aggaaaaaga gggctcctct gggagatgta tgcttactct cttaggcctt   180
tcattcatct tggcaggact tattgttggt ggagcctgca tttacaagta cttcatgccc   240
aagagcacca tttaccgtgg agagatgtgc tttttttgatt ctgaggatcc tgcaaattcc   300
cttcgtggag gagagcctaa cttcctgcct gtgactgagg aggctgacat tcgtgaggat   360
gacaacattg caatcattga tgtgcctgtc cccagtttct ctgatagtga ccctgcagca   420
attattcatg actttgaaaa gggaatgact gcttacctgg acttgttgct ggggaactgc   480
tatctgatgc ccctcaatac ttctattgtt atgcctccaa aaatctggt agagctcttt   540
ggcaaactgg cgagtggcag atatctgcct caaacttatg tggttcgaga agacctagtt   600
gctgtggagg aaattcgtga tgttagtaac cttggcatct ttatttacca actttgcaat   660
aacagaaagt ccttccgcct tcgtcgcaga gacctcttgc tgggtttcaa caaacgtgcc   720
attgataaat gctggaagat tagacacttc cccaacgaat ttattgttga gaccaagatc   780
tgtcaagagt acccatacga tgttccagat tacgcttaa                          819
```

<210> SEQ ID NO 56
<211> LENGTH: 272
<212> TYPE: PRT
<213> ORGANISM: Artificial Sequence
<220> FEATURE:
<223> OTHER INFORMATION: pMCN2i_ITM2A-HA insert

<400> SEQUENCE: 56

Met Val Lys Ile Ala Phe Asn Thr Pro Thr Ala Val Gln Lys Glu Glu
1               5                   10                  15

Ala Arg Gln Asp Val Glu Ala Leu Leu Ser Arg Thr Val Arg Thr Gln
            20                  25                  30

Ile Leu Thr Gly Lys Glu Leu Arg Val Ala Thr Gln Glu Lys Glu Gly
        35                  40                  45

Ser Ser Gly Arg Cys Met Leu Thr Leu Leu Gly Leu Ser Phe Ile Leu
    50                  55                  60

Ala Gly Leu Ile Val Gly Gly Ala Cys Ile Tyr Lys Tyr Phe Met Pro
65                  70                  75                  80

Lys Ser Thr Ile Tyr Arg Gly Glu Met Cys Phe Phe Asp Ser Glu Asp
                85                  90                  95

Pro Ala Asn Ser Leu Arg Gly Gly Glu Pro Asn Phe Leu Pro Val Thr
            100                 105                 110

Glu Glu Ala Asp Ile Arg Glu Asp Asp Asn Ile Ala Ile Ile Asp Val
        115                 120                 125

Pro Val Pro Ser Phe Ser Asp Ser Asp Pro Ala Ala Ile Ile His Asp
    130                 135                 140

Phe Glu Lys Gly Met Thr Ala Tyr Leu Asp Leu Leu Leu Gly Asn Cys
145                 150                 155                 160

Tyr Leu Met Pro Leu Asn Thr Ser Ile Val Met Pro Pro Lys Asn Leu
                165                 170                 175

Val Glu Leu Phe Gly Lys Leu Ala Ser Gly Arg Tyr Leu Pro Gln Thr
            180                 185                 190

Tyr Val Val Arg Glu Asp Leu Val Ala Val Glu Glu Ile Arg Asp Val
        195                 200                 205

Ser Asn Leu Gly Ile Phe Ile Tyr Gln Leu Cys Asn Asn Arg Lys Ser
    210                 215                 220

```
Phe Arg Leu Arg Arg Arg Asp Leu Leu Leu Gly Phe Asn Lys Arg Ala
225                 230                 235                 240

Ile Asp Lys Cys Trp Lys Ile Arg His Phe Pro Asn Glu Phe Ile Val
            245                 250                 255

Glu Thr Lys Ile Cys Gln Glu Tyr Pro Tyr Asp Val Pro Asp Tyr Ala
        260                 265                 270
```

<210> SEQ ID NO 57
<211> LENGTH: 27
<212> TYPE: DNA
<213> ORGANISM: Artificial Sequence
<220> FEATURE:
<223> OTHER INFORMATION: PCR primer

<400> SEQUENCE: 57

```
gaattctaca agtacttcat gcccaag                                          27
```

<210> SEQ ID NO 58
<211> LENGTH: 48
<212> TYPE: DNA
<213> ORGANISM: Artificial Sequence
<220> FEATURE:
<223> OTHER INFORMATION: PCR primer

<400> SEQUENCE: 58

```
gtcgactcag tggtggtggt ggtggtgctc ttgacagatc ttggtctc                   48
```

<210> SEQ ID NO 59
<211> LENGTH: 48
<212> TYPE: DNA
<213> ORGANISM: Artificial Sequence
<220> FEATURE:
<223> OTHER INFORMATION: PCR primer

<400> SEQUENCE: 59

```
gtcgactcag tggtggtggt ggtggtgttt gccaaagagc tctaccag                   48
```

<210> SEQ ID NO 60
<211> LENGTH: 1290
<212> TYPE: DNA
<213> ORGANISM: Artificial Sequence
<220> FEATURE:
<223> OTHER INFORMATION: pGEX_GST-ITM2A-L insert

<400> SEQUENCE: 60

```
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600 tggcctttgc agggctggca agccacgttt ggtggtggcg accatcctcc aaaatcggat     660
ctggaagttc tgttccaggg gcccctggga tccccggaat tctacaagta cttcatgccc     720
```

```
aagagcacca tttaccgtgg agagatgtgc ttttttgatt ctgaggatcc tgcaaattcc      780
cttcgtggag gagagcctaa cttcctgcct gtgactgagg aggctgacat tcgtgaggat      840
gacaacattg caatcattga tgtgcctgtc cccagtttct ctgatagtga ccctgcagca      900
attattcatg actttgaaaa gggaatgact gcttacctgg acttgttgct ggggaactgc      960
tatctgatgc ccctcaatac ttctattgtt atgcctccaa aaatctggt agagctcttt     1020 ggcaaactgg cgagtggcag atatctgcct caaacttatg tggttcgaga agacctagtt     1080
gctgtggagg aaattcgtga tgttagtaac cttggcatct ttatttacca actttgcaat     1140
aacagaaagt ccttccgcct tcgtcgcaga gacctcttgc tgggtttcaa caaacgtgcc     1200
attgataaat gctggaagat tagacacttc cccaacgaat ttattgttga gaccaagatc     1260
tgtcaagagc accaccacca ccaccactga                                       1290
```

<210> SEQ ID NO 61
<211> LENGTH: 429
<212> TYPE: PRT
<213> ORGANISM: Artificial Sequence
<220> FEATURE:
<223> OTHER INFORMATION: pGEX_GST-ITM2A-L insert

<400> SEQUENCE: 61

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Pro Glu Phe Tyr Lys Tyr Phe Met Pro
225                 230                 235                 240

Lys Ser Thr Ile Tyr Arg Gly Glu Met Cys Phe Phe Asp Ser Glu Asp
                245                 250                 255
```

```
Pro Ala Asn Ser Leu Arg Gly Gly Glu Pro Asn Phe Leu Pro Val Thr
            260                 265                 270
Glu Glu Ala Asp Ile Arg Glu Asp Asn Ile Ala Ile Ile Asp Val
        275                 280                 285
Pro Val Pro Ser Phe Ser Asp Ser Asp Pro Ala Ile Ile His Asp
        290                 295                 300
Phe Glu Lys Gly Met Thr Ala Tyr Leu Asp Leu Leu Gly Asn Cys
305                 310                 315                 320
Tyr Leu Met Pro Leu Asn Thr Ser Ile Val Met Pro Pro Lys Asn Leu
                325                 330                 335
Val Glu Leu Phe Gly Lys Leu Ala Ser Gly Arg Tyr Leu Pro Gln Thr
            340                 345                 350
Tyr Val Val Arg Glu Asp Leu Val Ala Val Glu Glu Ile Arg Asp Val
            355                 360                 365
Ser Asn Leu Gly Ile Phe Ile Tyr Gln Leu Cys Asn Asn Arg Lys Ser
370                 375                 380
Phe Arg Leu Arg Arg Arg Asp Leu Leu Leu Gly Phe Asn Lys Arg Ala
385                 390                 395                 400
Ile Asp Lys Cys Trp Lys Ile Arg His Phe Pro Asn Glu Phe Ile Val
                405                 410                 415
Glu Thr Lys Ile Cys Gln Glu His His His His His His
            420                 425

<210> SEQ ID NO 62
<211> LENGTH: 1047
<212> TYPE: DNA
<213> ORGANISM: Artificial Sequence
<220> FEATURE:
<223> OTHER INFORMATION: pGEX_GST-ITM2A-S insert

<400> SEQUENCE: 62 atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg ttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggaagttc tgttccaggg gcccctggga tccccggaat tctacaagta cttcatgccc    720
aagagcacca tttaccgtgg agagatgtgc ttttttgatt ctgaggatcc tgcaaattcc    780
cttcgtggag gagagcctaa cttcctgcct gtgactgagg aggctgacat tcgtgaggat    840
gacaacattg caatcattga tgtgcctgtc ccagtttct ctgatagtga ccctgcagca    900
attattcatg actttgaaaa gggaatgact gcttacctgg acttgttgct ggggaactgc    960
tatctgatgc ccctcaatac ttctattgtt atgcctccaa aaaatctggt agagctcttt   1020
ggcaaacacc accaccaca ccactga                                          1047
```

<210> SEQ ID NO 63
<211> LENGTH: 348
<212> TYPE: PRT
<213> ORGANISM: Artificial Sequence
<220> FEATURE:
<223> OTHER INFORMATION: pGEX_GST-ITM2A-S insert

<400> SEQUENCE: 63

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Glu Val Leu
    210                 215                 220

Phe Gln Gly Pro Leu Gly Ser Pro Glu Phe Tyr Lys Tyr Phe Met Pro
225                 230                 235                 240

Lys Ser Thr Ile Tyr Arg Gly Glu Met Cys Phe Phe Asp Ser Glu Asp
                245                 250                 255

Pro Ala Asn Ser Leu Arg Gly Gly Glu Pro Asn Phe Leu Pro Val Thr
            260                 265                 270

Glu Glu Ala Asp Ile Arg Glu Asp Asn Ile Ala Ile Ile Asp Val
        275                 280                 285

Pro Val Pro Ser Phe Ser Asp Ser Asp Pro Ala Ala Ile Ile His Asp
    290                 295                 300

Phe Glu Lys Gly Met Thr Ala Tyr Leu Asp Leu Leu Leu Gly Asn Cys
305                 310                 315                 320

Tyr Leu Met Pro Leu Asn Thr Ser Ile Val Met Pro Pro Lys Asn Leu
                325                 330                 335

Val Glu Leu Phe Gly Lys His His His His His
            340                 345

<210> SEQ ID NO 64
<211> LENGTH: 64

```
<212> TYPE: DNA
<213> ORGANISM: Artificial Sequence
<220> FEATURE:
<223> OTHER INFORMATION: PCR primer

<400> SEQUENCE: 64
gcggccgctt aagcgtaatc tggaacatcg tatgggtaaa ggcggaagga ctttctgtta    60
ttgc                                                                 64

<210> SEQ ID NO 65
<211> LENGTH: 711
<212> TYPE: DNA
<213> ORGANISM: Artificial Sequence
<220> FEATURE:
<223> OTHER INFORMATION: pMCN2i_ITM2A-furin-HA insert

<400> SEQUENCE: 65
atggtgaaaa tcgccttcaa taccectacc gccgtgcaaa aggaggaggc gcggcaagac    60
gtggaggccc tcctgagccg cacggtcaga actcagatac tgaccggcaa ggagctccga   120
gttgccaccc aggaaaaaga gggctcctct gggagatgta tgcttactct cttaggcctt   180
tcattcatct tggcaggact tattgttggt ggagcctgca tttacaagta cttcatgccc   240
aagagcacca tttaccgtgg agagatgtgc ttttttgatt ctgaggatcc tgcaaattcc   300
cttcgtggag agagcctaa cttcctgcct gtgactgagg aggctgacat tcgtgaggat   360
gacaacattg caatcattga tgtgcctgtc cccagtttct ctgatagtga ccctgcagca   420
attattcatg actttgaaaa gggaatgact gcttacctgg acttgttgct ggggaactgc   480
tatctgatgc ccctcaatac ttctattgtt atgcctccaa aaatctggt agagctcttt   540 ggcaaactgg cgagtggcag atatctgcct caaacttatg tggttcgaga agacctagtt   600
gctgtggagg aaattcgtga tgttagtaac cttggcatct ttatttacca actttgcaat   660
aacagaaagt ccttccgcct ttacccatac gatgttccag attacgctta a          711

<210> SEQ ID NO 66
<211> LENGTH: 236
<212> TYPE: PRT
<213> ORGANISM: Artificial Sequence
<220> FEATURE:
<223> OTHER INFORMATION: pMCN2i_ITM2A-furin-HA insert

<400> SEQUENCE: 66

Met Val Lys Ile Ala Phe Asn Thr Pro Thr Ala Val Gln Lys Glu Glu
1               5                   10                  15

Ala Arg Gln Asp Val Glu Ala Leu Leu Ser Arg Thr Val Arg Thr Gln
            20                  25                  30

Ile Leu Thr Gly Lys Glu Leu Arg Val Ala Thr Gln Glu Lys Glu Gly
        35                  40                  45

Ser Ser Gly Arg Cys Met Leu Thr Leu Leu Gly Leu Ser Phe Ile Leu
    50                  55                  60

Ala Gly Leu Ile Val Gly Gly Ala Cys Ile Tyr Lys Tyr Phe Met Pro
65                  70                  75                  80

Lys Ser Thr Ile Tyr Arg Gly Glu Met Cys Phe Phe Asp Ser Glu Asp
                85                  90                  95

Pro Ala Asn Ser Leu Arg Gly Gly Glu Pro Asn Phe Leu Pro Val Thr
            100                 105                 110

Glu Glu Ala Asp Ile Arg Glu Asp Asp Asn Ile Ala Ile Ile Asp Val
        115                 120                 125
```

| Pro | Val | Pro | Ser | Phe | Ser | Asp | Ser | Asp | Pro | Ala | Ala | Ile | Ile | His | Asp |
|-----|-----|-----|-----|-----|-----|-----|-----|-----|-----|-----|-----|-----|-----|-----|-----|
|     | 130 |     |     |     | 135 |     |     |     | 140 |     |     |     |     |     |     |

| Phe | Glu | Lys | Gly | Met | Thr | Ala | Tyr | Leu | Asp | Leu | Leu | Gly | Asn | Cys |
|-----|-----|-----|-----|-----|-----|-----|-----|-----|-----|-----|-----|-----|-----|-----|
| 145 |     |     |     | 150 |     |     |     |     | 155 |     |     |     |     | 160 |

| Tyr | Leu | Met | Pro | Leu | Asn | Thr | Ser | Ile | Val | Met | Pro | Pro | Lys | Asn | Leu |
|-----|-----|-----|-----|-----|-----|-----|-----|-----|-----|-----|-----|-----|-----|-----|-----|
|     |     |     | 165 |     |     |     |     | 170 |     |     |     |     | 175 |     |     |

| Val | Glu | Leu | Phe | Gly | Lys | Leu | Ala | Ser | Gly | Arg | Tyr | Leu | Pro | Gln | Thr |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Tyr | Val | Val | Arg | Glu | Asp | Leu | Val | Ala | Val | Glu | Ile | Arg | Asp | Val |
|-----|-----|-----|-----|-----|-----|-----|-----|-----|-----|-----|-----|-----|-----|-----|
|     |     | 195 |     |     |     | 200 |     |     |     |     | 205 |     |     |     |

| Ser | Asn | Leu | Gly | Ile | Phe | Ile | Tyr | Gln | Leu | Cys | Asn | Asn | Arg | Lys | Ser |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Phe | Arg | Leu | Tyr | Pro | Tyr | Asp | Val | Pro | Asp | Tyr | Ala |
|-----|-----|-----|-----|-----|-----|-----|-----|-----|-----|-----|-----|
| 225 |     |     |     |     | 230 |     |     |     |     | 235 |     |

<210> SEQ ID NO 67
<211> LENGTH: 29
<212> TYPE: DNA
<213> ORGANISM: Artificial Sequence
<220> FEATURE:
<223> OTHER INFORMATION: PCR primer

<400> SEQUENCE: 67
atggtgaaga tcgccttcaa caccccctac                                    29

<210> SEQ ID NO 68
<211> LENGTH: 28
<212> TYPE: DNA
<213> ORGANISM: Artificial Sequence
<220> FEATURE:
<223> OTHER INFORMATION: PCR primer

<400> SEQUENCE: 68
tcactcctga cagatcttgg tttcaacg                                      28

<210> SEQ ID NO 69
<211> LENGTH: 37
<212> TYPE: DNA
<213> ORGANISM: Artificial Sequence
<220> FEATURE:
<223> OTHER INFORMATION: PCR primer

<400> SEQUENCE: 69
taagaattcc accatggtga agatcgcctt caacacc                            37

<210> SEQ ID NO 70
<211> LENGTH: 59
<212> TYPE: DNA
<213> ORGANISM: Artificial Sequence
<220> FEATURE:
<223> OTHER INFORMATION: PCR primer

<400> SEQUENCE: 70
gcggccgctt aagcgtaatc tggaacatcg tatgggtact cctgacagat cttggtttc    59

<210> SEQ ID NO 71
<211> LENGTH: 819
<212> TYPE: DNA
<213> ORGANISM: Artificial Sequence
<220> FEATURE:
<223> OTHER INFORMATION: pMCN2i_mITM2A-HA insert

<400> SEQUENCE: 71

| | | | |
|---|---|---|---|
| atggtgaaga tcgccttcaa caccctacg gcggtgcaaa aggaggaggc gcggcaagat | | | 60 |
| gtagaggcgc tcgtcagtcg cactgtccga gctcaaatcc tgactggcaa ggagctcaga | | | 120 |
| gttgtcccgc aggagaaaga tggctcatct gggagatgca tgcttactct cctaggcctc | | | 180 |
| tcattcatct tggcaggact gattgttggt ggagcctgca tttacaagta cttcatgccc | | | 240 |
| aagagcacca tttaccatgg tgagatgtgc ttctttgatt ctgaggatcc tgtcaattcc | | | 300 |
| attcctggag gagagccata ctttctgcct gtgactgagg aggctgatat ccgtgaggat | | | 360 |
| gacaacattg ccatcattga tgtgcctgtg cccagtttct ctgatagcga tccggcggca | | | 420 |
| attattcacg actttgagaa gggaatgact gcttacctgg acttgctttt gggaaactgt | | | 480 |
| tatctgatgc ccctcaatac ttccattgtt atgactccaa agaatctggt ggaactttt | | | 540 |
| ggaaaactgg caagtggcaa gtatttgcct catacttatg tggttcgtga agacctggtt | | | 600 |
| gctgtggaag aaattcgtga tgttagtaac cttggtattt ttatttacca actttgcaac | | | 660 |
| aaccgaaaat ccttccgcct tagacgcaga gaccttctgc tgggtttcaa caagcgtgcc | | | 720 |
| attgacaaat gctggaagat tagacacttc cccaatgaat ttatcgttga aaccaagatc | | | 780 |
| tgtcaggagt acccatacga tgttccagat tacgcttaa | | | 819 |

<210> SEQ ID NO 72
<211> LENGTH: 272
<212> TYPE: PRT
<213> ORGANISM: Artificial Sequence
<220> FEATURE:
<223> OTHER INFORMATION: pMCN2i_mITM2A-HA insert

<400> SEQUENCE: 72

```
Met Val Lys Ile Ala Phe Asn Thr Pro Thr Ala Val Gln Lys Glu Glu
1               5                   10                  15

Ala Arg Gln Asp Val Glu Ala Leu Val Ser Arg Thr Val Arg Ala Gln
            20                  25                  30

Ile Leu Thr Gly Lys Glu Leu Arg Val Val Pro Gln Glu Lys Asp Gly
        35                  40                  45

Ser Ser Gly Arg Cys Met Leu Thr Leu Leu Gly Leu Ser Phe Ile Leu
    50                  55                  60

Ala Gly Leu Ile Val Gly Gly Ala Cys Ile Tyr Lys Tyr Phe Met Pro
65                  70                  75                  80

Lys Ser Thr Ile Tyr His Gly Glu Met Cys Phe Phe Asp Ser Glu Asp
                85                  90                  95

Pro Val Asn Ser Ile Pro Gly Gly Glu Pro Tyr Phe Leu Pro Val Thr
            100                 105                 110

Glu Glu Ala Asp Ile Arg Glu Asp Asp Asn Ile Ala Ile Ile Asp Val
        115                 120                 125

Pro Val Pro Ser Phe Ser Asp Ser Asp Pro Ala Ala Ile Ile His Asp
    130                 135                 140

Phe Glu Lys Gly Met Thr Ala Tyr Leu Asp Leu Leu Leu Gly Asn Cys
145                 150                 155                 160

Tyr Leu Met Pro Leu Asn Thr Ser Ile Val Met Thr Pro Lys Asn Leu
                165                 170                 175

Val Glu Leu Phe Gly Lys Leu Ala Ser Gly Lys Tyr Leu Pro His Thr
            180                 185                 190

Tyr Val Val Arg Glu Asp Leu Val Ala Val Glu Glu Ile Arg Asp Val
        195                 200                 205

Ser Asn Leu Gly Ile Phe Ile Tyr Gln Leu Cys Asn Asn Arg Lys Ser
    210                 215                 220
```

Phe Arg Leu Arg Arg Arg Asp Leu Leu Leu Gly Phe Asn Lys Arg Ala
225                 230                 235                 240

Ile Asp Lys Cys Trp Lys Ile Arg His Phe Pro Asn Glu Phe Ile Val
            245                 250                 255

Glu Thr Lys Ile Cys Gln Glu Tyr Pro Tyr Asp Val Pro Asp Tyr Ala
        260                 265                 270

<210> SEQ ID NO 73
<211> LENGTH: 21
<212> TYPE: DNA
<213> ORGANISM: Artificial Sequence
<220> FEATURE:
<223> OTHER INFORMATION: PCR primer

<400> SEQUENCE: 73
gggccagtgg atagacagat g                                           21

<210> SEQ ID NO 74
<211> LENGTH: 23
<212> TYPE: DNA
<213> ORGANISM: Artificial Sequence
<220> FEATURE:
<223> OTHER INFORMATION: PCR primer

<400> SEQUENCE: 74
gctcactgga tggtgggaag atg                                         23

<210> SEQ ID NO 75
<211> LENGTH: 22
<212> TYPE: DNA
<213> ORGANISM: Artificial Sequence
<220> FEATURE:
<223> OTHER INFORMATION: PCR primer

<400> SEQUENCE: 75
cccactagtt acccacccca aa                                          22

<210> SEQ ID NO 76
<211> LENGTH: 22
<212> TYPE: DNA
<213> ORGANISM: Artificial Sequence
<220> FEATURE:
<223> OTHER INFORMATION: PCR primer

<400> SEQUENCE: 76
tgttgggctt gcttttccgc tc                                          22

<210> SEQ ID NO 77
<211> LENGTH: 22
<212> TYPE: DNA
<213> ORGANISM: Artificial Sequence
<220> FEATURE:
<223> OTHER INFORMATION: PCR primer

<400> SEQUENCE: 77
ggctcctctg ggagatgtat gc                                          22

<210> SEQ ID NO 78
<211> LENGTH: 22
<212> TYPE: DNA
<213> ORGANISM: Artificial Sequence
<220> FEATURE:
<223> OTHER INFORMATION: PCR primer

<400> SEQUENCE: 78
atcctcacga atgtcagcct cc 22

<210> SEQ ID NO 79
<211> LENGTH: 4
<212> TYPE: PRT
<213> ORGANISM: Artificial Sequence
<220> FEATURE:
<223> OTHER INFORMATION: peptide linker

<400> SEQUENCE: 79

Gly Gly Gly Ser
1

<210> SEQ ID NO 80
<211> LENGTH: 4
<212> TYPE: PRT
<213> ORGANISM: Artificial Sequence
<220> FEATURE:
<223> OTHER INFORMATION: peptide linker

<400> SEQUENCE: 80

Ser Gly Gly Gly
1

<210> SEQ ID NO 81
<211> LENGTH: 5
<212> TYPE: PRT
<213> ORGANISM: Artificial Sequence
<220> FEATURE:
<223> OTHER INFORMATION: peptide linker

<400> SEQUENCE: 81

Gly Gly Gly Gly Ser
1               5

<210> SEQ ID NO 82
<211> LENGTH: 5
<212> TYPE: PRT
<213> ORGANISM: Artificial Sequence
<220> FEATURE:
<223> OTHER INFORMATION: peptide linker

<400> SEQUENCE: 82

Ser Gly Gly Gly Gly
1               5

<210> SEQ ID NO 83
<211> LENGTH: 6
<212> TYPE: PRT
<213> ORGANISM: Artificial Sequence
<220> FEATURE:
<223> OTHER INFORMATION: peptide linker

<400> SEQUENCE: 83

Gly Gly Gly Gly Gly Ser
1               5

<210> SEQ ID NO 84
<211> LENGTH: 6
<212> TYPE: PRT
<213> ORGANISM: Artificial Sequence
<220> FEATURE:
<223> OTHER INFORMATION: peptide linker

<400> SEQUENCE: 84

Ser Gly Gly Gly Gly Gly

```
<210> SEQ ID NO 85
<211> LENGTH: 7
<212> TYPE: PRT
<213> ORGANISM: Artificial Sequence
<220> FEATURE:
<223> OTHER INFORMATION: peptide linker

<400> SEQUENCE: 85

Gly Gly Gly Gly Gly Gly Ser
1               5

<210> SEQ ID NO 86
<211> LENGTH: 7
<212> TYPE: PRT
<213> ORGANISM: Artificial Sequence
<220> FEATURE:
<223> OTHER INFORMATION: peptide linker

<400> SEQUENCE: 86

Ser Gly Gly Gly Gly Gly Gly
1               5
```

DIAGNOSIS AND TREATMENT OF CANCER USING ANTI-ITM2A ANTIBODY

CROSS-REFERENCE TO RELATED APPLICATIONS

This application is a Divisional of U.S. application Ser. No. 14/112,590, filed Oct. 18, 2013; which is a National Stage of International Application No. PCT/JP2012/002697, filed on Apr. 18, 2012; which claims priority from Japanese Patent Application No. 2011-092488, filed on Apr. 18, 2011. The contents thereof are incorporated herein by reference.

TECHNICAL FIELD

The present invention relates to an antibody binding to an ITM2A protein, a method for diagnosing cancer, a method for treating cancer, and an anticancer agent.

BACKGROUND ART

The ITM2A molecule is a type II membrane protein that is expressed in precursor cells involved in chondrogenesis or osteogenesis (Non Patent Literature 1). This protein is known to be expressed at the early stage of chondrogenesis (Non Patent Literature 2) to inhibit the chondrogenesis (Non Patent Literature 3). ITM2A is also expressed in T cells in the thymus gland (Non Patent Literature 4). The inhibition of T cell activation by an anti-ITM2A polyclonal antibody is disclosed (Patent Literature 1). Patent Literature 1 claims the treatment of T cell leukemia/lymphoma using an anti-ITM2A antibody, but does not specifically discuss the expression of ITM2A in T cell leukemia/lymphoma or the treatment of these diseases. According to the reports, the expression of ITM2A at the gene level in Ewing's sarcoma or acute myeloid leukemia has been confirmed by microarray analysis (Non Patent Literatures 5, 6, and 7). Nonetheless, it has not been specifically confirmed so far that T cell leukemia/lymphoma, Ewing's sarcoma, or acute myeloid leukemia can be treated using an anti-ITM2A antibody.

References cited herein are as shown below. The contents described in these literatures are incorporated herein by reference in their entirety.

CITATION LIST

Patent Literature

Patent Literature 1: WO2008137500

Non Patent Literature

Non Patent Literature 1: J Biol Chem (1996) 271: 19475
Non Patent Literature 2: Biol Cell (2004) 96: 463
Non Patent Literature 3: Differentiation (2009) 78: 108
Non Patent Literature 4: J Exp Med (1999) 190: 217
Non Patent Literature 5: Cancer Res (2004) 64: 8213
Non Patent Literature 6: Cancer Res (2008) 68: 2176
Non Patent Literature 7: PLoS One (2010) 5: e9466

SUMMARY OF INVENTION

Technical Problem

An object of the present invention is to provide a novel antibody binding to an ITM2A protein, a novel method for diagnosing cancer, a novel method for treating cancer, a novel cell growth inhibitor, and an anticancer agent.

Solution to Problem

The present inventors have found that ITM2A mRNA is expressed in Ewing's sarcoma having EWS-FLI1 translocation. The present inventors have prepared an anti-ITM2A monoclonal antibody and also found that ITM2A protein is expressed in Ewing's sarcoma, acute myeloid leukemia, T cell lymphoma, and T cell acute lymphocytic leukemia cell lines. The present inventors have further found that the anti-ITM2A monoclonal antibody exerts an antibody-dependent cell-mediated cytotoxicity (ADCC) activity and inhibits the growth of the Ewing's sarcoma cells, acute myeloid leukemia, and T cell lymphoma cell lines, and T cell acute lymphocytic leukemia cells in the presence of a toxin-conjugated secondary antibody. From these results, the present inventors have found that the anti-ITM2A antibody is useful in the treatment and diagnosis of cancer involving ITM2A expression, such as Ewing's sarcoma, acute myeloid leukemia, T cell lymphoma, and T cell acute lymphocytic leukemia, and consequently completed the present invention.

Specifically, the present invention provides a monoclonal antibody binding to an ITM2A protein. The present invention further provides a monoclonal antibody which binds to an ITM2A protein and has a cytotoxic activity against cells expressing the ITM2A protein. Preferably, the cytotoxic activity is an ADCC activity. The present invention also provides an anti-ITM2A monoclonal antibody conjugated with a cytotoxic substance.

The present invention further provides a pharmaceutical composition comprising the monoclonal antibody binding to an ITM2A protein as an active ingredient. The present invention further provides a cell growth inhibitor comprising the monoclonal antibody binding to an ITM2A protein as an active ingredient. The present invention further provides an anticancer agent comprising the monoclonal antibody binding to an ITM2A protein as an active ingredient.

The present invention further provides a pharmaceutical composition comprising the monoclonal antibody binding to an ITM2A protein and a pharmaceutically acceptable carrier. More specifically, the present invention provides the following [1] to [47]:

[1] a monoclonal antibody binding to a fragment of an ITM2A protein having the amino acid sequence represented by SEQ ID NO: 1;
[2] the antibody according to [1], wherein the fragment is a fragment consisting of amino acids 75 to 227 in the amino acid sequence represented by SEQ ID NO: 1;
[3] the antibody according to [1] or [2], wherein the antibody has a cytotoxic activity;
[4] the antibody according to [3], wherein the cytotoxic activity is an antibody-dependent cell-mediated cytotoxicity (ADCC) activity;
[5] the antibody according to [3], wherein the cytotoxic activity is a complement-dependent cytotoxicity (CDC) activity;
[6] the antibody according to any of [1] to [5], wherein the antibody is conjugated with a cytotoxic substance;
[7] the antibody according to [6], wherein the antibody has an internalization activity;
[8] the antibody according to any of [1] to [7], wherein the antibody inhibits cancer cell growth;
[9] the antibody according to [8], wherein the cancer cell is a Ewing's sarcoma cell;

[10] the antibody according to [9], wherein the Ewing's sarcoma cell is a cell having observable chromosomal translocation;
[11] the antibody according to [10], wherein the chromosomal translocation is t(11;22)(q24;q12);
[12] the antibody according to [8], wherein the cancer cell is a blood cancer cell;
[13] the antibody according to [12], wherein the blood cancer is any of T cell leukemia, T cell lymphoma, acute myeloid leukemia, B cell tumor, and multiple myeloma;
[14] an antibody described in any of the following (1) to (27):
(1) an antibody comprising an H chain having the amino acid sequence represented by SEQ ID NO: 3 as CDR1, the amino acid sequence represented by SEQ ID NO: 4 as CDR2, and the amino acid sequence represented by SEQ ID NO: 5 as CDR3;
(2) an antibody comprising an L chain having the amino acid sequence represented by SEQ ID NO: 6 as CDR1, the amino acid sequence represented by SEQ ID NO: 7 as CDR2, and the amino acid sequence represented by SEQ ID NO: 8 as CDR3;
(3) an antibody comprising the H chain described in (1) and the L chain described in (2);
(4) an antibody comprising an H chain having the amino acid sequence represented by SEQ ID NO: 9 as CDR1, the amino acid sequence represented by SEQ ID NO: 10 as CDR2, and the amino acid sequence represented by SEQ ID NO: 11 as CDR3;
(5) an antibody comprising an L chain having the amino acid sequence represented by SEQ ID NO: 12 as CDR1, the amino acid sequence represented by SEQ ID NO: 13 as CDR2, and the amino acid sequence represented by SEQ ID NO: 14 as CDR3;
(6) an antibody comprising the H chain described in (4) and the L chain described in (5);
(7) an antibody comprising an H chain having the amino acid sequence represented by SEQ ID NO: 15 as CDR1, the amino acid sequence represented by SEQ ID NO: 16 as CDR2, and the amino acid sequence represented by SEQ ID NO: 17 as CDR3;
(8) an antibody comprising an L chain having the amino acid sequence represented by SEQ ID NO: 18 as CDR1, the amino acid sequence represented by SEQ ID NO: 19 as CDR2, and the amino acid sequence represented by SEQ ID NO: 20 as CDR3;
(9) an antibody comprising the H chain described in (7) and the L chain described in (8);
(10) an antibody comprising an H chain having the amino acid sequence represented by SEQ ID NO: 21 as CDR1, the amino acid sequence represented by SEQ ID NO: 22 as CDR2, and the amino acid sequence represented by SEQ ID NO: 23 as CDR3;
(11) an antibody comprising an L chain having the amino acid sequence represented by SEQ ID NO: 24 as CDR1, the amino acid sequence represented by SEQ ID NO: 25 as CDR2, and the amino acid sequence represented by SEQ ID NO: 26 as CDR3;
(12) an antibody comprising the H chain described in (10) and the L chain described in (11);
(13) the antibody described in any of (1) to (12) which is a chimeric antibody;
(14) the antibody described in any of (1) to (12) which is a humanized antibody;
(15) the antibody described in (1) or (3), comprising the amino acid sequence represented by SEQ ID NO: 28;
(16) the antibody described in (2) or (3), comprising the amino acid sequence represented by SEQ ID NO: 30;
(17) the antibody described in (4) or (6), comprising the amino acid sequence represented by SEQ ID NO: 32;
(18) the antibody described in (5) or (6), comprising the amino acid sequence represented by SEQ ID NO: 34;
(19) the antibody described in (7) or (9), comprising the amino acid sequence represented by SEQ ID NO: 36;
20) the antibody described in (8) or (9), comprising the amino acid sequence represented by SEQ ID NO: 38;
(21) the antibody described in (10) or (12), comprising the amino acid sequence represented by SEQ ID NO: 40;
(22) the antibody described in (11) or (12), comprising the amino acid sequence represented by SEQ ID NO: 42;
(23) the antibody described in any of (15) to (22) which is a chimeric antibody;
(24) an antibody that has an amino acid sequence of an antibody described in any of (1) to (23) with a substitution, deletion, addition, and/or insertion of one or more amino acid(s) and has an activity equivalent to or a binding activity equivalent to that of the antibody;
(25) an antibody capable of binding to an epitope to which a second antibody binds, wherein the second antibody is the antibody described in any of (1) to (23); and
(26) an antibody capable of inhibiting the binding of a second antibody to an ITM2A protein fragment consisting of amino acids 75 to 227 in the amino acid sequence represented by SEQ ID NO: 1, wherein the second antibody is the antibody described in any of (1) to (23);
[15] the antibody according to any of [1] to [14], wherein the antibody has a human constant region;
[16] the antibody according to [15], wherein the antibody is a chimeric antibody, a humanized antibody, or a human antibody;
[17] the antibody according to any of [1] to [16], wherein the antibody is deficient in fucose added to its sugar chain or has a sugar chain having bisecting GlcNAc;
[18] a pharmaceutical composition comprising an antibody according to any of [1] to [17] as an active ingredient;
[19] a cell growth inhibitor comprising an antibody according to any of [1] to [17] as an active ingredient;
[20] an anticancer agent comprising an antibody according to any of [1] to [17] as an active ingredient;
[21] the anticancer agent according to [20], wherein the cancer to be treated is Ewing's sarcoma;
[22] the anticancer agent according to [21], wherein the Ewing's sarcoma has observable chromosomal translocation;
[23] the anticancer agent according to [22], wherein the chromosomal translocation is t(11;22)(q24;q12);
[24] the anticancer agent according to [20], wherein the cancer cell is a blood cancer cell;
[25] the anticancer agent according to [24], wherein the blood cancer is any of T cell leukemia, T cell lymphoma, acute myeloid leukemia, B cell tumor, and multiple myeloma;
[26] a method for treating cancer, comprising administering an antibody according to any of [1] to [17];
[27] the method according to [26], wherein the cancer to be treated is Ewing's sarcoma;
[28] the method according to [27], wherein the Ewing's sarcoma has observable chromosomal translocation;
[29] the method according to [28], wherein the chromosomal translocation is t(11;22)(q24;q12);
[30] the method according to [26], wherein the cancer cell is a blood cancer cell;

[31] the method according to [30], wherein the blood cancer is any of T cell leukemia, T cell lymphoma, acute myeloid leukemia, B cell tumor, and multiple myeloma;

[32] a method for predicting the efficacy of cancer treatment by the administration of an antibody according to any of [1] to [17], comprising the step of detecting the expression level of an ITM2A in a biological sample collected from a test subject;

[33] the method according to [32], wherein an ITM2A protein in the sample collected from a test subject is detected;

[34] the diagnosis method according to [33], wherein the detection of the ITM2A protein is performed using an antibody binding to the ITM2A protein;

[35] the method according to any of [32] to [34], wherein the cancer to be treated is Ewing's sarcoma;

[36] the method according to [35], wherein the Ewing's sarcoma has observable chromosomal translocation;

[37] the method according to [36], wherein the chromosomal translocation is t(11;22)(q24;q12);

[38] the method according to [35], wherein the cancer cell is a blood cancer cell;

[39] the method according to [38], wherein the blood cancer is any of T cell leukemia, T cell lymphoma, acute myeloid leukemia, B cell tumor, and multiple myeloma;

[40] a method for determining the presence of cancer in a test subject, comprising detecting an ITM2A protein in a sample collected from the test subject;

[41] a method for determining the presence of cancer in a test subject, comprising the following steps:
(a) providing a sample collected from the test subject; and
(b) detecting an ITM2A protein contained in the sample of step (a) using an antibody binding to the ITM2A protein;

[42] a method for determining the presence of cancer in a test subject, comprising the following steps:
(a) administering, to the test subject, a radioisotope-labeled antibody having a binding activity to an ITM2A protein; and
(b) detecting the accumulation of the radioisotope;

[43] the method according to any of [40] to [42], wherein the cancer whose presence is to be determined is Ewing's sarcoma;

[44] the method according to [43], wherein the Ewing's sarcoma has observable chromosomal translocation;

[45] the method according to [44], wherein the chromosomal translocation is t(11;22)(q24;q12);

[46] the method according to [43], wherein the cancer cell is a blood cancer cell; and

[47] the method according to [46], wherein the blood cancer is any of T cell leukemia, T cell lymphoma, acute myeloid leukemia, B cell tumor, and multiple myeloma.

BRIEF DESCRIPTION OF DRAWINGS

FIG. 1A shows the expression profile of ITM2A mRNA in various normal tissues. FIG. 1B shows the expression profile of ITM2A mRNA in blood cancer cell lines, Ewing's sarcoma cell lines, and Ewing's sarcoma tissues.

FIG. 2A shows the binding activity of the anti-ITM2A antibody to GST-ITM2A-L. FIG. 2B shows the binding activity of the anti-ITM2A antibody to GST-ITM2A-S.

FIG. 3A shows the binding activity of the anti-ITM2A antibodies to ITM2A-expressing CHO cells. FIG. 3B shows the binding activity of the anti-ITM2A antibodies to ITM2A-furin-expressing CHO cells. FIG. 3C shows the binding activity of the anti-ITM2A antibodies to CHO cells. FIG. 3C shows the binding activity of an anti-HA antibody to ITM2A- or ITM2A-furin-expressing CHO cells.

FIG. 4A shows the binding activity of the anti-ITM2A antibodies to human ITM2A-expressing CHO cells. FIG. 4B shows the binding activity of the anti-ITM2A antibodies to mouse ITM2A-expressing CHO cells.

FIGS. 5A-5E show results of evaluating the binding activity of the isolated anti-ITM2A antibodies to ITM2A by Western blot. Lane A represents a whole cell lysate of ITM2A-expressing CHO cells. Lane B represents a whole cell lysate of ITM2A-furin-expressing CHO cells. Lane C represents a whole cell lysate of CHO cells. FIG. 5A shows the binding activity of the antibody BE5-1. FIG. 5B shows the binding activity of the antibody BE6-1. FIG. 5C shows the binding activity of the antibody BE7-1-1. FIG. 5D shows the binding activity of the antibody BE13-1. FIG. 5E shows the binding activity of the anti-HA antibody.

FIG. 6A shows the expression of ITM2A in the Ewing's sarcoma cell line A-673. FIG. 6B shows the expression of ITM2A in the Ewing's sarcoma cell line RD-ES. FIG. 6C shows the expression of ITM2A in the Ewing's sarcoma cell line SK-ES-1. FIG. 6D shows the expression of ITM2A in the Ewing's sarcoma cell line SK-N-MC. FIG. 6E shows the expression of ITM2A in the T cell acute lymphocytic leukemia cell line CCRF-CEM. FIG. 6F shows the expression of ITM2A in the T cell acute lymphocytic leukemia cell line Jurkat. FIG. 6G shows the expression of ITM2A in the T cell acute lymphocytic leukemia cell line MOLT4. FIG. 6H shows the expression of ITM2A in the T cell lymphoma cell line HuT78. FIG. 6I shows the expression of ITM2A in the acute myeloid leukemia cell line KG-1a. FIG. 6J shows the expression of ITM2A in the acute myeloid leukemia cell line TF-1a.

FIG. 7A shows the ADCC activity against the Ewing's sarcoma cell line A-673. FIG. 7B shows the ADCC activity against the Ewing's sarcoma cell line SK-N-MC. FIG. 7C shows the ADCC activity against the T cell acute lymphocytic leukemia cell line CCRF-CEM. FIG. 7D shows the ADCC activity against the acute myeloid leukemia cell line KG-1a.

FIG. 8A shows the cytotoxic activity against the Ewing's sarcoma cell line A-673. FIG. 8B shows the cytotoxic activity against the T cell acute lymphocytic leukemia cell line CCRF-CEM. FIG. 8C shows the cytotoxic activity against the T cell lymphoma cell line HuT78.

FIG. 9A shows the expression of EWS-FLI1 fusion genes in clinical Ewing's sarcoma samples. FIG. 9B shows the expression of ITM2A in clinical Ewing's sarcoma samples.

DESCRIPTION OF EMBODIMENTS

ITM2A

Figure 1A:
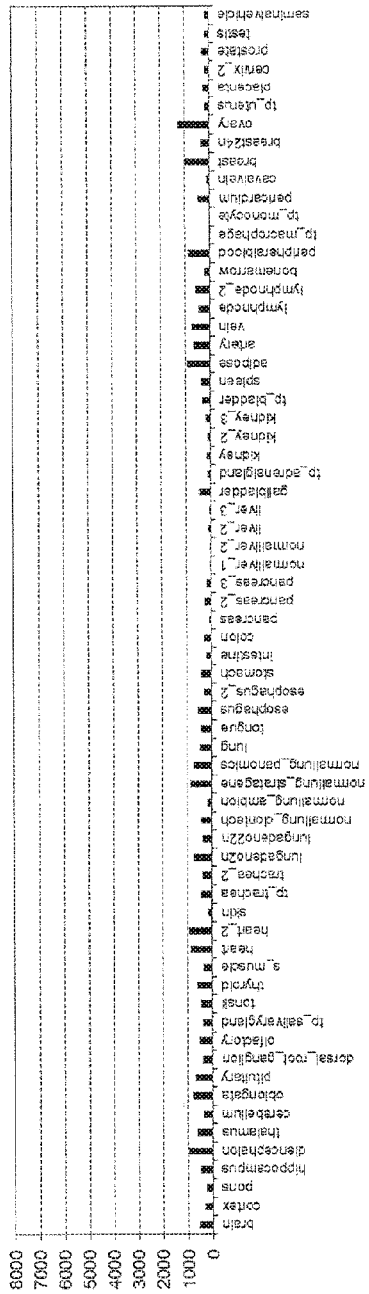
FIGS. 1A-1B show the expression profile of ITM2A mRNA in normal tissues, Ewing's sarcoma cell lines, Ewing's sarcoma tissues, and blood cancer cell lines obtained using Human Exon 1.0 ST Array.

In the present invention, ITM2A is a type II membrane protein. The amino acid sequence of human ITM2A and a gene sequence encoding this amino acid sequence are disclosed in NCBI Accession Nos. NP 004858.1 (SEQ ID NO: 1) and NM_004867.4 (SEQ ID NO: 2), respectively. An ITM2A used in the present invention may be a splicing variant or a variant (or a mutant). In the present invention, the ITM2A protein is meant to include both of the full-length protein and its fragment. The fragment refers to a polypeptide comprising an arbitrary region of the ITM2A protein and may not have the functions of the natural ITM2A protein. Examples of the fragment include a fragment comprising the extracellular region of the ITM2A protein. The extracellular region of the ITM2A protein corresponds to positions 75 to 263 in the amino acid sequence of SEQ ID NO: 1. In another aspect, examples of the fragment preferably include a polypeptide consisting of amino acids 75 to 227 in the ITM2A protein represented by SEQ ID NO: 1.

Preparation of Anti-ITM2A Antibody

The anti-ITM2A antibody used in the present invention needs only to bind to the ITM2A protein and is not limited by its origin, type, shape, etc. Specifically, an antibody known in the art can be used, such as a non-human animal antibody (e.g., a mouse, rat, or camel antibody), a human antibody, a chimeric antibody, or a humanized antibody. In the present invention, a monoclonal or polyclonal antibody can be used. A monoclonal antibody can be preferably used. The binding of the antibody to the ITM2A protein is preferably specific binding. Also, the anti-ITM2A antibody used in the present invention may be an antibody that recognizes human ITM2A. In such a case, an antibody that specifically recognizes human ITM2A can be used. Alternatively, an antibody that simultaneously recognizes human ITM2A and non-human animal-derived ITM2A (e.g., mouse ITM2A) can also be preferably used.

The anti-ITM2A antibody used in the present invention can be obtained as a polyclonal or monoclonal antibody using means known in the art. The anti-ITM2A antibody used in the present invention is particularly preferably a mammal-derived monoclonal antibody. The mammal-derived monoclonal antibody encompasses, for example, those produced by hybridomas and those produced by hosts transformed with expression vectors containing an antibody gene by a genetic engineering approach.

Basically, monoclonal antibody-producing hybridomas can be prepared according to a technique known in the art as follows: first, animals are immunized with an ITM2A protein used as a sensitizing antigen according to a usual immunization method. Immunocytes obtained from the immunized animals can be fused with parental cells known in the art by a usual cell fusion method to obtain hybridomas. These hybridomas can be further screened for cells producing the antibody of interest by a usual screening method to select hybridomas producing anti-ITM2A antibodies.

Specifically, a monoclonal antibody is prepared, for example, as follows: first, ITM2A gene can be expressed to obtain ITM2A protein used as a sensitizing antigen to obtain antibodies. The nucleotide sequence of the ITM2A gene is disclosed in, for example, NCBI Accession No. NM_004867.4 (SEQ ID NO: 2). Specifically, an ITM2A-encoding gene sequence is inserted into an expression vector known in the art, with which appropriate host cells are then transformed. Then, the human ITM2A protein of interest can be purified from the host cells or from a culture supernatant thereof by a method known in the art. Also, purified natural ITM2A protein can be used similarly. Alternatively, fusion proteins comprising the desired partial polypeptide of the ITM2A protein fused with a different polypeptide may be used as immunogens, as used in the present invention. For example, antibody Fc fragments, peptide tags, and the like can be used for producing the fusion proteins serving as immunogens. Two or more genes respectively encoding the desired polypeptide fragments are fused in frame, and the fusion gene can be inserted into expression vectors to prepare expression vectors for the fusion proteins. The method for preparing the fusion proteins is described in Molecular Cloning 2nd ed. (Sambrook, J. et al., Molecular Cloning 2nd ed., 9.47-9.58, Cold Spring Harbor Lab. Press, 1989).

An ITM2A protein thus purified can be used as a sensitizing antigen for the immunization of a mammal. A partial peptide of ITM2A may also be used as a sensitizing antigen. For example, the following peptides can be used as a sensitizing antigen:

a peptide obtained by chemical synthesis on the basis of the amino acid sequence of human ITM2A, a peptide obtained by the incorporation of a portion of the ITM2A gene into an expression vector, followed by gene expression, and a peptide obtained by the degradation of the ITM2A protein with a proteolytic enzyme.

The region and size of the partial peptide of ITM2A used are not limited. A preferable region can be selected from the amino acid sequence constituting the extracellular domain of ITM2A (positions 75 to 263 in the amino acid sequence of SEQ ID NO: 2). The number of amino acids constituting the peptide serving as a sensitizing antigen is preferably at least 3 or more, for example, 5 or more or 6 or more. More specifically, peptides of 6 to 263 residues, preferably 7 to 200 residues, more preferably 8 to 100, 8 to 50, or 10 to 30 residues, can be used as sensitizing antigens.

The mammal to be immunized with the sensitizing antigen is not particularly limited. For obtaining the monoclonal antibody by the cell fusion method, the animal to be immunized is preferably selected in consideration of compatibility with the parental cells used in cell fusion. In general, a rodent is preferable as the animal to be immunized. Specifically, mouse, rat, hamster, or rabbit can be used as the animal to be immunized. In addition, monkey or the like may be used as the animal to be immunized.

The animal can be immunized with the sensitizing antigen according to a method known in the art. For example, a general method can involve immunizing the mammal with the sensitizing antigen by intraperitoneal or subcutaneous injection. Specifically, the sensitizing antigen is administered to the mammal several times at 4- to 21-day intervals. The sensitizing antigen is diluted with PBS (phosphate-buffered saline), saline, or the like at an appropriate dilution ratio and used in the immunization. The sensitizing antigen may be administered together with an adjuvant. For example, the antigen is mixed with a Freund's complete adjuvant and emulsified, and the resulting emulsion can be used as the sensitizing antigens. Also, an appropriate carrier can be used in the immunization with the sensitizing antigens. Particularly, in the case of using partial peptides having a small molecular weight as the sensitizing antigen, the sensitizing antigen peptide bound with a carrier protein such as albumin or keyhole limpet hemocyanin can be preferably used in the immunization.

On the other hand, the monoclonal antibody can also be obtained by DNA immunization. The DNA immunization is an immunostimulation method involving: immunizing an animal by the administration of vector DNA that has been constructed in a form capable of expressing an antigenic protein-encoding gene (e.g., the gene represented by SEQ ID NO: 2) in the immunized animal; and allowing the immunized animal to express the immunizing antigen in vivo. The DNA immunization can be expected to be superior to general immunization methods using the administration of a protein antigen as follows:

the DNA immunization can provide immunostimulation with membrane protein (e.g., ITM2A) with its structure maintained; and the DNA immunization eliminates the need of purifying an immunizing antigen.

The DNA immunization, however, is difficult to combine with immunostimulation means such as an adjuvant. The amino acid sequence of ITM2A is highly homologous among species. The amino acid sequence of human-derived ITM2A represented by SEQ ID NO: 1 has identity of 99%, 98%, 96%, 94%, 94%, and 90% to, for example, the amino acid sequences of rabbit (*Oryctolagus cuniculus*)-, horse-, mouse-, giant panda-, rat-, and pig-derived ITM2A proteins, respectively. In light of such structural identity, it is an unexpected consequence that the monoclonal antibody binding to ITM2A was obtained by the DNA immunization and the administration of protein antigens involving immunostimulation means such as adjuvant.

In order to obtain the monoclonal antibody of the present invention by the DNA immunization, an animal is first immunized by the administration of a DNA expressing an ITM2A protein. An ITM2A-encoding DNA can be synthesized by a method known in the art such as PCR. The obtained DNA is inserted into an appropriate expression vector, which is then administered to an animal. For example, a commercially available expression vector such as pcDNA3.1 can be used as the expression vectors. Also, a method generally used can be used for administering the vectors to the animals. For example, gold particles with the expression vector adsorbed thereon can be inserted into cells using a gene gun to perform the DNA immunization.

A rise in the amount of the desired antibody is confirmed in the serum of the mammals thus immunized. Then, immunocytes are collected from the mammal and subjected to cell fusion. Particularly, spleen cells can be used as preferable immunocytes.

Mammalian myeloma cells are used in the cell fusion with the immunocytes. The myeloma cells preferably have an appropriate selection marker for screening. The selection marker refers to a character that can survive (or cannot survive) under particular culture conditions. For example, hypoxanthine-guanine phosphoribosyltransferase deficiency (hereinafter, abbreviated to HGPRT deficiency) or thymidine kinase deficiency (hereinafter, abbreviated to TK deficiency) is known in the art as the selection marker. Cells having the HGPRT or TK deficiency is sensitive to hypoxanthine-aminopterin-thymidine (hereinafter, abbreviated to HAT-sensitive). The HAT-sensitive cells are killed in a HAT selective medium because the cells fail to synthesize DNA. By contrast, these cells, when fused with normal cells, grow even in the HAT selective medium because the fused cells can continue DNA synthesis by use of the salvage pathway of the normal cells.

The cells having the HGPRT or TK deficiency can be selected in a medium containing 6-thioguanine or 8-azaguanine (hereinafter, abbreviated to 8AG) for the HGPRT deficiency or 5'-bromodeoxyuridine for the TK deficiency. The normal cells are killed by incorporating these pyrimidine analogs into their DNAs. By contrast, the cells deficient in these enzymes can survive in the selective medium because the cells cannot incorporate the pyrimidine analogs therein. A selection marker based on an index of 2-deoxystreptamine antibiotic (gentamicin analog) resistance brought about by a neomycin resistance gene is called G418 resistance. Various myeloma cells suitable for the cell fusion are known in the art. For example, the following myeloma cells can be used in the production of the monoclonal antibody according to the present invention:

P3 (P3x63Ag8.653) (J. Immunol. (1979) 123, 1548-1550),
P3x63Ag8U.1 (Current Topics in Microbiology and Immunology (1978) 81, 1-7),
NS-1 (Kohler. G. and Milstein, C. Eur. J. Immunol. (1976) 6, 511-519),
MPC-11 (Margulies. D. H. et al., Cell (1976) 8, 405-415),
SP2/0 (Shulman, M. et al., Nature (1978) 276, 269-270),
FO (de St. Groth, S. F. et al., J. Immunol. Methods (1980) 35, 1-21),
S194 (Trowbridge, I. S. J. Exp. Med. (1978) 148, 313-323),
R210 (Galfre, G. et al., Nature (1979) 277, 131-133), etc.

Basically, the cell fusion of the immunocytes with the myeloma cells is performed according to a method known in the art, for example, the method of Kohler and Milstein et al. (Kohler. G. and Milstein, C., Methods Enzymol. (1981) 73, 3-46).

More specifically, the cell fusion can be carried out, for example, in a usual nutrient culture medium in the presence of a cell fusion promoter. For example, polyethylene glycol (PEG) or hemagglutinating virus of Japan (HVJ) can be used as the fusion promoter. In addition, an auxiliary such as dimethyl sulfoxide is preferably added thereto, if desired, for enhancing fusion efficiency.

The ratio between the immunocytes and the myeloma cells used can be arbitrarily set. For example, the amount of the immunocytes is preferably set to 1 to 10 times that of the myeloma cells. For example, an RPMI1640 or MEM culture medium suitable for the growth of the myeloma cell line as well as a usual culture medium used in this kind of cell culture can be used as the culture medium in the cell fusion. A solution supplemented with serum (e.g., fetal calf serum (FCS)) can be further added to the culture medium.

In the procedures of the cell fusion, the immunocytes and the myeloma cells are well mixed in the predetermined amounts in the culture medium and mixed with a PEG solution preheated to approximately 37° C. to form the fusion cells (hybridomas) of interest. In the procedures of the cell fusion, for example, PEG having an average molecular weight on the order of 1000 to 6000 can usually be added at a concentration of 30 to 60% (w/v) to the cell suspension containing the immunocytes and the myeloma cells. Subsequently, the appropriate culture medium exemplified above is sequentially added to the cell suspension, and its supernatant is removed by centrifugation. This removal procedure is repeated to remove the cell fusion agents or the like unfavorable for hybridoma growth.

The hybridomas thus obtained can be grown in a selective medium appropriate for the selection marker of the myeloma cells used in the cell fusion. For example, the cells having the HGPRT or TK deficiency can be selected by culture in a HAT medium (culture medium containing hypoxanthine, aminopterin, and thymidine). Specifically, when HAT-sensitive myeloma cells are used in the cell fusion, only cells successfully fused with normal cells can be grown selectively in the HAT culture medium. The culture using the HAT culture medium is continued for a time long enough to kill cells (non-fused cells) other than the hybridomas of interest. Specifically, the culture can generally be performed for a few days to a few weeks to select the hybridomas of interest. Subsequently, hybridomas producing the antibody of interest are screened for and cloned as single clones by a usual limiting dilution method. Alternatively, the antibody that recognizes ITM2A may be prepared by a method described in International Publication No. WO2003104453.

The screening for the antibody of interest and the cloning as single clones thereof can be preferably carried out by a screening method based on antigen-antibody reaction known in the art. For example, a carrier (e.g., beads made of polystyrene or the like) or a commercially available 96-well microtiter plate bound with antigens are reacted with the culture supernatant of the hybridomas. Subsequently, the carrier is washed and then reacted with enzyme-labeled secondary antibodies or the like. When the culture supernatant contains the antibody of interest reactive with the sensitizing antigen, the secondary antibodies bind to the carrier via this antibody. The secondary antibodies bound with the carrier can be finally detected to determine the presence of the antibody of interest in the culture supernatant. As described above, the hybridomas producing the desired antibody capable of binding to the antigen can be cloned by a limiting dilution method or the like. In this screening and cloning as single clones, in addition to the ITM2A protein used in the immunization, an ITM2A protein substantially identical thereto can be preferably used as an antigen. As an example of the ITM2A protein substantially identical thereto, cell lines expressing ITM2A, the extracellular domain of ITM2A, or oligopeptides consisting of a partial amino acid sequence constituting the domain can be used as an antigen.

In addition to the method for obtaining the hybridomas by immunizing non-human animal with the antigen, human lymphocytes may be sensitized with the antigen to obtain the desired antibody. Specifically, the human lymphocytes are first sensitized with an ITM2A protein in vitro. Subsequently, the sensitized lymphocytes are fused with appropriate fusion partners. For example, human-derived myeloma cells capable of dividing throughout their lives can be used as the fusion partners (Japanese Patent Publication No. 1-59878). For example, human myeloma cells such as U266 can be used as the fusion partners. The anti-ITM2A antibody obtained by this method is a human antibody having a binding activity to the ITM2A protein.

The anti-ITM2A human antibody can also be obtained by administering the antigen ITM2A protein to transgenic animals having all repertoires of human antibody genes or by immunizing the animals with a DNA that has been constructed so as to express ITM2A in the animals. Antibody-producing cells from the immunized animals can acquire immortalizing characters by cell fusion with appropriate fusion partners or infection with Epstein-Barr virus. From the immortalized cells thus obtained, human antibodies against the ITM2A protein can be isolated (WO1994025585, WO1993012227, WO1992003918, and WO1994002602). The immortalized antibody-producing cells can be further cloned as cells producing antibodies having the reaction specificity of interest. In the case of immunizing the transgenic animals, the immune systems of the animals recognize human ITM2A as foreigners. Thus, the human antibodies against human ITM2A can be easily obtained.

The monoclonal antibody-producing hybridomas thus prepared can be subcultured in a usual medium. The hybridomas can also be stored over a long period in liquid nitrogen.

The hybridomas can be cultured according to a usual method. The monoclonal antibody of interest can be obtained from the culture supernatant thereof. Alternatively, the hybridomas may be administered to a mammal compatible therewith and grown, and the monoclonal antibody can be obtained from the ascitic fluids thereof. The former method is suitable for obtaining highly pure antibodies.

In the present invention, an antibody encoded by an antibody gene cloned from an antibody-producing cell may also be used. The cloned antibody gene incorporated in an appropriate vector is expressed as an antibody encoded thereby in a host by the introduction of the vector into the host. Methods for the antibody gene isolation, the introduction into vector, and the transformation of host cells have already been established (e.g., Vandamme, A. M. et al., Eur. J. Biochem. (1990) 192, 767-775).

For example, cDNAs encoding the variable regions (V regions) of the anti-ITM2A antibody can be obtained from the anti-ITM2A antibody-producing hybridoma cells. In order to obtain the cDNAs, usually, the total RNA is first extracted from the hybridoma. For example, the following methods can be used for the total RNA extraction from the cells:

guanidine ultracentrifugation method (Chirgwin, J. M. et al., Biochemistry (1979) 18, 5294-5299), and
AGPC method (Chomczynski, P. et al., Anal. Biochem. (1987) 162, 156-159).

From the extracted total RNA, mRNA can be purified using mRNA Purification Kit (manufactured by GE Healthcare Bio-Sciences Corp.) or the like. Alternatively, a kit for directly extracting total mRNA from cells is also commercially available, such as QuickPrep mRNA Purification Kit (manufactured by GE Healthcare Bio-Sciences Corp.). The total mRNA may be obtained from the hybridoma using such a kit. From the mRNA thus obtained, antibody V region-encoding cDNAs can be synthesized using reverse transcriptase. Arbitrary 15- to 30-base sequences selected from sequences common to mouse antibody genes can be used as primers for cDNA synthesis. Specifically, the antibody V region-encoding cDNAs can be obtained using primers having a DNA sequence represented by any of SEQ ID NOs: 97 to 100. The cDNAs can be synthesized using reverse transcriptase such as AMV Reverse Transcriptase First-strand cDNA Synthesis Kit (manufactured by Seikagaku Corp.). Alternatively, 5'-Ampli FINDER RACE Kit (manufactured by Clontech Laboratories, Inc.) and 5'-RACE PCR (Frohman, M. A. et al., Proc. Natl. Acad. Sci. USA (1988) 85, 8998-9002; and Belyavsky, A. et al., Nucleic Acids Res. (1989) 17, 2919-2932) may be appropriately used for the cDNA synthesis and amplification. In the course of such cDNA synthesis, appropriate restriction sites as described later can be introduced into both ends of the cDNAs.

Also, a cDNA library may be appropriately used for obtaining the antibody variable region-encoding genes. First, cDNAs are synthesized with mRNA extracted from the antibody-producing cells as template to obtain a cDNA library. A commercially available kit can be appropriately used in the cDNA library synthesis. In actuality, mRNA from only a small number of cells are obtained in a very small amount. Therefore, the direct purification of the mRNA generally results in low mRNA yields. Thus, the mRNA are usually purified from a mRNA preparation supplemented with carrier RNA shown to be free from the antibody genes. Alternatively, RNA may be extracted in a given amount. In such a case, antibody variable region-encoding mRNAs can be efficiently extracted from RNA obtained only from the antibody-producing cells without the addition of carrier RNA. The addition of the carrier RNA may be unnecessary for RNA extraction from, for example, 10 or more or 30 or more, preferably 50 or more antibody-producing cells.

The antibody genes can be amplified by PCR using the obtained cDNA library as template. A plurality of primers for the PCR amplification of the antibody genes are known in the art. For example, primers for human antibody gene amplification can be preferably designed on the basis of the disclosure of the paper (J. Mol. Biol. (1991) 222, 581-597) or the like. These primers have their respective nucleotide sequences differing on an immunoglobulin subclass basis. Thus, when cDNA library whose subclass is unknown is used as template, PCR is carried out using primers in consideration of every possibility.

From the PCR products thus obtained, the desired cDNA fragments are purified. Subsequently, the purified cDNA fragments are ligated with a vector DNA. The recombinant vectors thus prepared are introduced into E. coli or the like. A colony of E. coli transformed with the recombinant vectors is selected. A recombinant vector can be isolated from the E. coli that has formed the colony. Then, the cDNA inserted in the isolated recombinant vector can be sequenced by a method known in the art, for example, a dideoxynucleotide chain termination method.

Specifically, primers capable of amplifying genes respectively encoding γ1 to γ5 heavy chains and κ and λ light chains can be used, for example, for the purpose of obtaining human IgG-encoding genes. Primers annealing to a portion corresponding to the hinge region are generally used as 3' primers for amplifying IgG variable region genes. On the other hand, primers appropriate for each subclass are used as 5' primers.

The PCR products obtained by amplification using the primers for gene amplification corresponding to these heavy and light chain subclasses are synthesized as their respective independent gene library. The library thus synthesized can be combined to reshape immunoglobulins comprising the heavy and light chains in combination. The immunoglobulins thus reshaped can be screened for the antibody of interest with their binding activities to ITM2A as an index.

For example, for obtaining the antibody against ITM2A, more preferably, the antibody specifically binds to ITM2A. The antibody binding to ITM2A can be screened for, for example, by the following steps:
(1) contacting antibodies comprising V regions encoded by the obtained cDNAs, with ITM2A;
(2) detecting a complex of an ITM2A-bound antibody; and
(3) selecting the antibody binding to ITM2A.

The complex of an ITM2A-bound antibody (antigen-antibody complex) is detected by a method known in the art. Specifically, a test antibody is contacted with ITM2A immobilized on a carrier. Next, a labeled antibody that recognizes the antibody is contacted therewith. When the labeled antibody remaining on the carrier after washing of the carrier is detected, the binding of the test antibody to ITM2A can be demonstrated. An enzymatically active protein such as peroxidase or β-galactosidase, or a fluorescent material such as FITC can be appropriately used in the antibody labeling. Also, fixed preparations of ITM2A-expressing cells can be appropriately used for evaluating the binding activity of the antibody.

Panning using phage vectors may be used as a method for screening for the antibody with its binding activity as an index. When the antibody genes are obtained as libraries of heavy and light chain subclasses as described above, a screening method using phage vectors is advantageous. Genes respectively encoding heavy and light chain variable regions can be linked via an appropriate linker sequence to prepare genes encoding single chain Fv (scFv) molecules in which the heavy and light variable regions of the antibody are arranged on one chain. The scFv-encoding genes can be inserted to phage vectors to obtain phages expressing scFvs on their surface. The phages thus obtained are contacted with the antigen of interest. Then, antigen-bound phages are recovered. In this way, DNAs encoding scFvs having a binding activity to the desired antigen can be recovered. This procedure can be repeated, if necessary, to concentrate scFvs having the desired binding activity to the antigen.

In the present invention, the polynucleotide encoding the antibody may be a polynucleotide encoding the full-length antibody or may be a polynucleotide encoding a portion of the antibody. The term "a portion of the antibody" refers to an arbitrary portion of the antibody molecule. Hereinafter, the term "antibody fragment" is also used to represent a portion of the antibody. The antibody fragment according to the present invention is preferably an antibody fragment comprising a complementarity determining region (CDR) of the antibody. An antibody fragment comprising heavy and light chain complementarity determining regions (CDRs) is also preferable. More preferably, the antibody fragment of the present invention is an antibody fragment comprising three CDRs of a heavy chain variable region or/and a light chain variable region.

After obtainment of each cDNA encoding the V region of the desired anti-ITM2A antibody, the cDNA is digested with restriction enzymes that recognize the restriction sites inserted in both ends of the cDNA. The restriction enzymes are preferably restriction enzymes that can recognize and digest a nucleotide sequence unlikely to appear in the nucleotide sequences constituting the antibody genes. For inserting one copy of the digested fragment in the correct direction in an expression vector, restriction sites that provide cohesive ends are preferably inserted in the ends of the cDNA. The anti-ITM2A antibody V region-encoding cDNAs thus digested can be inserted to appropriate expression vectors to obtain antibody expression vectors. In this case, antibody constant region (C region)-encoding genes and the V region-encoding genes can be fused in frame to obtain chimeric antibodies. In this context, the chimeric antibodies refer to antibodies comprising constant and variable regions of different origins. Thus, heterogeneous (e.g., mouse-human) chimeric antibodies as well as human-human homogeneous chimeric antibodies are also encompassed by the chimeric antibody according to the present invention. The V region genes may be inserted in frame to expression vectors preliminarily having constant region-encoding DNA inserts to construct chimeric antibody expression vectors.

Specifically, for example, recognition sequences for restriction enzymes that digest the ends of the restriction sites inserted in both ends of the V region gene can be located on the 5' side of each expression vector carrying the DNA encoding the desired antibody constant region (C region). This expression vector and a vector having an insert of the V region gene are digested with the same combination of restriction enzymes. The resulting expression vector and V region gene are fused in frame to construct a chimeric antibody expression vector.

In order to produce the anti-ITM2A antibody used in the present invention, the antibody genes can be inserted into an expression vector such that these genes are expressed under the control of expression control regions. The expression control regions for antibody expression encompass, for example, enhancers and promoters. Subsequently, appropriate host cells can be transformed with these expression vectors to obtain recombinant cells expressing anti-ITM2A antibody-encoding DNAs.

For the antibody gene expression, the antibody heavy chain (H chain)- and light chain (L chain)-encoding DNAs can be incorporated separately in different expression vectors. The same host cell can be co-transfected with the H chain- and L chain-incorporated vectors and thereby allowed to express antibody molecules comprising the H and L chains. Alternatively, the H chain- and L chain-encoding DNAs may be inserted to a single expression vector, with which host cells can also be transformed to express antibody molecules comprising the H and L chains (WO1994011523).

Expression systems having many combinations of hosts and expression vectors used for preparing the antibody by introducing the isolated antibody genes into appropriate hosts are known in the art. All of these expression systems can be applied to the present invention. In the case of using eukaryotic cells as the hosts, animal, plant, or fungus cells can be used. Specifically, examples of the animal cells that can be used in the present invention can include the following cells:
(1) mammalian cells such as CHO, COS, myeloma, BHK (baby hamster kidney), Hela, Vero, HEK293, Ba/F3, HL-60, Jurkat, and SK-HEP1 cells;
(2) amphibian cells such as *Xenopus* oocytes; and
(3) insect cells such as sf9, sf21, and Tn5 cells.

Alternatively, antibody gene expression systems using cells derived from the genus *Nicotiana* (e.g., *Nicotiana tabacum*) as the plant cells that can be used in the present invention are known in the art. Cultured callus cells can be appropriately used for the plant cell transformation.

The following cells can be used as the fungus cells according to the present invention:
cells derived from yeasts of the genus *Saccharomyces* (e.g., *Saccharomyces cerevisiae*) and the genus *Pichia* (e.g., *Pichia pastoris*), and
cells derived from filamentous fungi of the genus *Aspergillus* (e.g., *Aspergillus niger*).

Alternatively, antibody gene expression systems using prokaryotic cells as hosts are also known in the art as the expression systems that can be used in the present invention. In the case of using, for example, bacterial cells, cells of bacteria such as *E. coli* and *Bacillus subtilis* can be preferably used in the present invention.

In the case of using mammalian cells in the present invention, a useful promoter routinely used (regardless of the presence or absence of an enhancer), the antibody gene to be expressed, and a poly A signal to be located 3'-downstream thereof can be functionally linked so that the antibody gene is expressed. Examples of the promoter/enhancer preferably include a human cytomegalovirus immediate early promoter/enhancer.

In addition, for example, virus promoters/enhancers or mammalian cell-derived promoters/enhancers (e.g., human elongation factor 1α (HEF1α)) may be used for the antibody expression. Specific examples of the viruses whose promoter/enhancer can be used preferably include retrovirus, polyomavirus, adenovirus, and simian virus 40 (SV40).

The SV40 promoter/enhancer can be preferably used according to the method of Mulligan et al. (Nature (1979) 277, 108). Also, the HEF1α promoter/enhancer can be easily used in the desired gene expression by the method of Mizushima et al. (Nucleic Acids Res. (1990) 18, 5322).

In the case of using *E. coli* as hosts, a useful promoter routinely used, a signal sequence for antibody secretion, and the antibody gene to be expressed can be functionally linked so that the gene is expressed. Examples of the promoter used preferably include lacZ and araB promoters. The lacZ promoter can be used according to the method of Ward et al. (Nature (1989) 341, 544-546; and FASEBJ. (1992) 6, 2422-2427). Alternatively, the araB promoter can be preferably used in the gene expression of interest according to the method of Better et al. (Science (1988) 240, 1041-1043).

In the case of antibody production in *E. coli* periplasm, a pelB signal sequence (Lei, S. P. et al., J. Bacteriol. (1987) 169, 4379) can be used for antibody secretion. The antibody thus produced in the periplasm is isolated and then refolded by use of a protein denaturant such as guanidine hydrochloride of urea such that the resulting antibody has the desired binding activity.

In the case of antibody production using animal cells, the signal sequence of the heavy or light chain gene of the antibody is preferably used as a signal sequence required for the extracellular secretion of the antibody. Alternatively, the signal sequence of a secretory protein such as IL-3 or IL-6 is also preferably used.

A replication origin derived from SV40, polyomavirus, adenovirus, bovine papillomavirus (BPV), or the like can be inserted in the expression vectors. A selection marker may be further inserted in the expression vectors for increasing the copy numbers of the inserted genes in the host cells. Specifically, the following selection markers can be used:
aminoglycoside phosphotransferase (APH) gene,
thymidine kinase (TK) gene,
*E. coli* xanthine-guanine phosphoribosyltransferase (Ecogpt) gene,
dihydrofolate reductase (dhfr) gene, etc.

Subsequently, the host cells transformed by the introduction of these expression vectors are cultured in vitro or in vivo. In this way, the antibody of interest is produced in, for example, the cultures of the host cells. The host cells are cultured according to a method known in the art. For example, a DMEM, MEM, RPMI1640, or IMDM medium can be used and may be used in combination with a solution supplemented with serum such as fetal calf serum (FCS).

The antibody thus expressed and produced can be purified by using, alone or in appropriate combination, usual protein purification methods known in the art. For example, affinity or chromatography columns (e.g., protein A columns), filters, ultrafiltration, salting-out, and dialysis can be selected and combined appropriately to separate and purify the antibody (Antibodies A Laboratory Manual. Ed Harlow, David Lane, Cold Spring Harbor Laboratory, 1988).

In addition to the host cells, transgenic animals may be used for the recombinant antibody production. Specifically, the antibody of interest can be obtained from animals transfected with the genes encoding this antibody of interest. For example, the antibody genes can be inserted in frame into genes encoding proteins specifically produced in milk to construct fusion genes encoding the protein and the antibody. For example, goat β casein can be used as the proteins secreted into milk. DNA fragments comprising the fusion genes having the antibody gene insert are injected into goat embryos, which are in turn introduced into female goats. From milk produced by transgenic goats (or progeny thereof) brought forth by the goats that have received the embryos, the desired antibody can be obtained as a fusion protein with the milk protein. In addition, hormone is appropriately administered to the transgenic goats for increasing the amount of milk containing the desired antibody produced from the transgenic goats (Ebert, K. M. et al., Bio/Technology (1994) 12, 699-702).

Non-human animal antibody-derived C regions can be used as the C regions in the recombinant antibody of the present invention. For example, Cγ1, Cγ2a, Cγ2b, Cγ3, Cμ, Cδ, Cα1, Cα2, and Cε can be used as mouse antibody H chain C regions, and Cκ and Cγ can be used as mouse antibody L chain C regions. Alternatively, an antibody of a rat, a rabbit, a goat, sheep, a camel, a monkey, or the like may be used as an antibody of an animal other than the mouse. Their sequences are known in the art. The C regions may be appropriately modified for improving the stability of the antibody itself or of its production.

In the case of administering the antibody according to the present invention to humans, a genetically recombinant antibody that has been engineered artificially can be administered, for example, for the purpose of reducing heteroantigenicity in humans. The genetically recombinant antibody encompasses, for example, chimeric antibodies and humanized antibodies. These engineered antibodies can be produced using a method known in the art.

The chimeric antibodies refer to antibodies comprising variable and constant regions of different origins linked to each other. For example, mouse-human heterogeneous chimeric antibodies are antibodies consisting of the heavy and light chain variable regions of a mouse antibody and the heavy and light chain constant regions of a human antibody. Mouse antibody variable region-encoding DNAs ligated in frame with human antibody constant region-encoding DNAs can be incorporated into expression vectors to prepare chimeric antibody-expressing recombinant vectors. Cells transformed with these vectors (recombinant cells) can be cultured to express the DNA inserts. The chimeric antibodies produced during the culture can be obtained from the cultures of the recombinant cells. Human antibody C regions are preferably used as the C regions of the chimeric antibodies and humanized antibodies.

For example, Cγ1, Cγ2, Cγ3, Cγ4, Cμ, Cδ, Cα1, Cα2, and Cε can be used as H chain C regions. Also, Cκ and Cλ can be used as L chain C regions. The amino acid sequences of these C regions and nucleotide sequences encoding these amino acid sequences are known in the art. The human antibody C regions may be appropriately modified for improving the stability of the antibody itself or of its production.

In general, the chimeric antibodies are composed of non-human animal-derived antibody V regions and human antibody-derived C regions. By contrast, the humanized antibodies are composed of non-human animal-derived antibody complementarity determining regions (CDRs), human antibody-derived framework regions (FRs), and human antibody-derived C regions. The humanized antibodies are useful as active ingredients for a therapeutic agent of the present invention, owing to their reduced immunogenicity in the human body.

Each antibody variable region is typically composed of three complementarity determining regions (CDRs) flanked by four framework regions (FRs). The CDR regions substantially determine the binding specificity of the antibody for its antigen. The CDRs have diverse amino acid sequences. On the other hand, amino acid sequences constituting the FRs are often highly analogous even among antibodies having binding specificity for different antigens. Therefore, in general, the binding specificity of a certain antibody can allegedly be transplanted to other antibodies through CDR grafting to FRs.

The humanized antibodies are also called reshaped human antibodies. Specifically, for example, humanized antibodies comprising non-human animal (e.g., mouse) antibody CDRs grafted in human antibodies are known in the art. General gene recombination approaches are also known for obtaining the humanized antibodies.

Specifically, for example, Overlap Extension PCR is known in the art as a method for grafting mouse antibody CDRs to human FRs. In the Overlap Extension PCR, a nucleotide sequence encoding each mouse antibody CDR to be grafted is added to the sequences of primers used for human antibody FR synthesis. The primers used are prepared for each of the four FRs. For grafting the mouse CDRs to the human FRs, in general, it is allegedly advantageous to select human FRs highly homologous to the FRs of the mouse antibody from which the mouse CDRs are derived, in order to maintain the CDR functions. Specifically, in general, the mouse CDRs are preferably grafted to human FRs consisting of amino acid sequences highly homologous to those of the mouse FRs adjacent to the mouse CDRs to be grafted.

As described above, the nucleotide sequences to be ligated are designed such that the sequences are ligated in frame. The human FR-encoding nucleotide sequences are individually synthesized by PCR using their respective primers. The resulting PCR products contain the mouse CDR-encoding DNA added to each human FR-encoding sequence. The mouse CDR-encoding nucleotide sequences are designed such that the nucleotide sequence in each product overlaps with another. Subsequently, the overlapping CDR portions in the PCR products synthesized with human antibody genes as templates are annealed to each other for complementary strand synthesis reaction. Through this reaction, the human FR sequences are ligated via the mouse CDR sequences.

Finally, the full-length gene of the V region comprising three CDRs and four FRs ligated is amplified by PCR using primers that respectively anneal to the 5' and 3' ends thereof and have an added recognition sequence for an appropriate restriction enzyme. The V region gene DNA thus obtained and a human antibody C region-encoding DNA can be inserted into expression vectors such that these DNAs are fused in frame to prepare vectors for human-type antibody expression. These expression vectors are introduced into hosts to establish recombinant cells. The recombinant cells are cultured for the expression of the humanized antibody-encoding DNA to produce the humanized antibodies into the cultures of the cultured cells (EP239400 and WO1996002576).

The humanized antibodies thus prepared can be evaluated for their binding activities to the antigen by qualitative or quantitative assay to thereby preferably select human antibody FRs such that these FRs allow CDRs to form a favorable antigen-binding site when ligated via the CDRs. If necessary, human antibody FR amino acid residue(s) may be substituted such that the CDRs of the resulting reshaped human antibody form an appropriate antigen-binding site. For example, the desired mutation can be introduced in the amino acid sequence of human FR by the application of the PCR method used in the mouse CDR grafting to the human FRs. Specifically, a mutation of a partial nucleotide sequence can be introduced to the primers annealing to a human FR nucleotide sequence. The human FR nucleotide sequence synthesized using such primers contains the mutation thus introduced so as to bring about the desired amino acid substitution. The variant antibodies having the substituted amino acid(s) can be evaluated for their binding activities to the antigen by the same assay as above to select variant FR sequences having the desired properties (Sato, K. et al., Cancer Res, 1993, 53, 851-856).

As described above, the method for obtaining human antibodies is also known in the art. In addition, a technique of obtaining human antibodies by panning using human antibody libraries is also known. For example, human antibody V regions are expressed as a single chain antibody (scFv) on the surface of phages by a phage display method. The gene of a phage selected with its binding activity to the antigen as an index can be analyzed to determine DNA sequences encoding the V regions of the human antibody binding to the antigen. After the determination of the DNA sequence of the antigen-binding scFv, the V region sequences fused in frame with the sequences of the desired human antibody C regions are inserted to appropriate expression vectors to prepare human antibody expression vectors. The expression vectors are introduced into the preferable expression cells as exemplified above. The expression cells are cultured for the expression of the human antibody-encoding genes to obtain the human antibodies. These methods are already known in the art (WO1992001047, WO19992020791, WO1993006213, WO1993011236, WO1993019172, WO1995001438, and WO1995015388).

In a preferable aspect, examples of the antibody used in the present invention also include an antibody having a human constant region, as described above.

The antibody of the present invention encompasses not only bivalent antibodies typified by IgG but also monovalent antibodies or polyvalent antibodies typified by IgM as long as these antibodies bind to the ITM2A protein. The polyvalent antibody of the present invention encompasses polyvalent antibodies having antigen-binding sites, all of which are the same as each other or some or all of which are different from each other. The antibody of the present invention is not limited to whole antibody molecules, and a low-molecular antibody or a modified form thereof can be preferably used as long as the antibody binds to the ITM2A protein.

The low-molecular antibody encompasses an antibody fragment deficient in a portion of the whole antibody (e.g., whole IgG). Such partial deficiency of the antibody molecule is accepted as long as the resulting antibody fragment is capable of binding to the ITM2A antigen. The antibody fragment according to the present invention preferably comprises one or both of heavy chain variable (VH) and light chain variable (VL) regions. Also, the antibody fragment according to the present invention preferably contains CDRs. The amino acid sequence of VH or VL may have substitution, deletion, addition, and/or insertion. The antibody fragment of the present invention may be deficient in a portion of one or both of VH and VL as long as the resulting antibody fragment is capable of binding to the ITM2A antigen. Alternatively, a chimerized or humanized variable region may be used. Specific examples of the antibody fragment preferably include Fab, Fab', F(ab')2, and Fv. Specific examples of the low-molecular antibody preferably include Fab, Fab', F(ab')2, Fv, scFv (single chain Fv), Diabody, sc(Fv)2 (single chain (Fv)2), and scFv-Fc. Multimers (e.g., dimmers, trimers, tetramers, and polymers) of these antibodies are also encompassed by the low-molecular antibody of the present invention.

The antibody fragment can be obtained by the enzymatic treatment of the whole antibody. For example, papain, pepsin, or plasmin is known in the art as an enzyme for forming the antibody fragment. Alternatively, genes encoding such antibody fragments may be constructed, and these genes can be introduced into expression vectors so that the antibody fragments are expressed in appropriate host cells (e.g., Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 476-496; Lamoyi, E., Methods in Enzymology (1989) 121, 652-663; Rousseaux, J. et al., Methods in Enzymology (1989) 121, 663-669; and Bird, R. E. et al., TIBTECH (1991) 9, 132-137).

Each digestive enzyme recognizes a particular amino acid sequence in the whole antibody and cleaves the whole antibody into the following antibody fragment having a particular structure:
papain digestion: F(ab)2 or Fab,
pepsin digestion: F(ab')2 or Fab', and
plasmin digestion: Facb.

The use of a genetic engineering approach for the antibody fragments thus obtained enzymatically can delete an arbitrary portion of the antibody.

Thus, the low-molecular antibody according to the present invention encompasses antibody fragments that lack an arbitrary region as long as these antibody fragments have binding affinity for ITM2A.

The Diabody refers to a bivalent antibody fragment constructed by gene fusion (e.g., Holliger P et al., Proc. Natl. Acad. Sci. USA (1993) 90, 6444-6448, EP404097, and WO1993011161). The Diabody is a dimer composed of two polypeptide chains. Usually, each of the polypeptide chains constituting the dimer comprises VL and VH linked in frame via a linker. The linker in the Diabody is generally too short to form a single chain variable region fragment having an antigen-binding site in which VL and VH on the same polypeptide chain are associated with each other. Specifically, the number of amino acid residues constituting the linker is, for example, approximately 5 residues. Therefore, VL and VH encoded on the same polypeptide chain form a dimer by association with VH and VL, respectively, on another polypeptide chain. As a result, the Diabody has two antigen-binding sites.

The scFv is obtained by linking VH and VL of the antibody. In the scFv, VH and VL are linked via a linker, preferably, a peptide linker (Huston, J. S. et al., Proc. Natl. Acad. Sci. USA, (1988), 85, 5879-5883). VH and VL in the scFv may be derived from any of the antibodies described herein. The structure of the peptide linker that links VH and VL is not particularly limited. For example, an arbitrary single chain peptide of approximately 3 to 25 residues can be used as the linker. Specifically, for example, a peptide linker described later can be used.

VL and VH can be linked, for example, by the PCR method described above. First, of the following DNA sequences, DNAs encoding the whole or desired partial amino acid sequence are used as templates for linking VL and VH by PCR:
DNA sequences encoding the H chain or VH of the antibody, and
DNA sequences encoding the L chain or VL of the antibody.

The VL-encoding DNA and the VH-encoding DNA are separately amplified by PCR using a pair of primers respectively having both terminal partial sequences of each DNA to be amplified. Subsequently, a DNA encoding the peptide linker moiety is prepared. The peptide linker-encoding DNA can also be synthesized using PCR. Specifically, nucleotide sequences that can be linked to the amplification products of the VL and VH nucleotide sequences synthesized separately are respectively added in advance to the 5' sequences of primers used. Subsequently, PCR is performed using each DNA of [VH-encoding DNA]-[peptide linker-encoding DNA]-[VL-encoding DNA] and primers for assembly PCR.

The primers for assembly PCR consist of the combination of a primer annealing to the 5' sequence of the [VH-encoding DNA] and a primer annealing to the 3' sequence of the [VL-encoding DNA]. Specifically, the primers for assembly PCR are a primer set that allows PCR amplification of a DNA encoding the full-length sequence of the scFv to be synthesized. By contrast, the [peptide linker-encoding DNA] contains a preliminarily added nucleotide sequence that can be linked to the VH- and VL-encoding DNAs. As a result, these DNAs are linked and, further, finally prepared into a full-length scFv gene amplification product by PCR using the primers for assembly PCR. Once the scFv-encoding DNA is prepared, expression vectors containing this DNA and cells transformed with the expression vectors (recombinant cells) can be obtained according to a routine method. In addition, the resulting recombinant cells can be cultured for the expression of the scFv-encoding DNA to obtain the scFv from the cultures of the cells.

The scFv-Fc is a low-molecular antibody comprising an Fc region fused in frame to scFv comprising antibody VH and VL (Cellular & Molecular Immunology (2006) 3, 439-443). The origin of the scFv used in scFv-Fc preparation is not particularly limited, and, for example, scFv derived from IgM can be preferably used. The origin of the Fc is not particularly limited, and, for example, Fc derived from mouse IgG (mouse IgG2a, etc.) or human IgG (human IgG1, etc.) can be appropriately used. Thus, in a preferable aspect, examples of the scFv-Fc can include scFv-Fc comprising an IgM antibody scFv fragment linked to mouse IgG2a CH2 (e.g., Cγ2) and CH3 (e.g., Cγ3) via the hinge region (Hγ) of mouse IgG2a, and scFv-Fc comprising an IgM antibody scFv fragment linked to human IgG1 CH2 and CH3 via the hinge region of human IgG1.

The sc(Fv)2 is a low-molecular antibody having a single chain polypeptide formed by two VHs and two VLs linked via linkers or the like (Hudson et al, J. Immunol. Methods (1999) 231, 177-189). The sc(Fv)2 can be prepared, for example, by linking two scFvs via a linker.

Examples of the sc(Fv)2 include an antibody wherein two VHs and two VLs are aligned as VH, VL, VH, and VL (i.e., [VH]-linker-[VL]-linker-[VH]-linker-[VL]) in this order starting at the N-terminus of the single chain polypeptide.

The order of two VHs and two VLs is not particularly limited to the arrangement described above and may be any order of arrangement. Examples thereof can also include the following arrangements:
[VL]-linker-[VH]-linker-[VH]-linker-[VL],
[VH]-linker-[VL]-linker-[VL]-linker-[VH],
[VH]-linker-[VH]-linker-[VL]-linker-[VL],
[VL]-linker-[VL]-linker-[VH]-linker-[VH], and
[VL]-linker-[VH]-linker-[VL]-linker-[VH].

For example, an arbitrary peptide linker or a synthetic compound linker (e.g., linkers disclosed in Protein Engineering (1996) 9 (3), 299-305) that can be introduced by genetic engineering can be preferably used as the linker that links the antibody variable regions. The peptide linker can be preferably used as the linker according to the present invention. The length of the peptide linker is not particularly limited and may be appropriately selected by those skilled in the art according to the purpose. The number of amino acid residues constituting the peptide linker is usually 1 to 100 amino acids, preferably 3 to 50 amino acids, more preferably 5 to 30 amino acids, particularly preferably 12 to 18 amino acids (e.g., 15 amino acids).

An arbitrary sequence can be appropriately adopted as the amino acid sequence constituting the peptide linker as long as this sequence does not inhibit the binding effect of the scFv. For example, the following amino acid sequences can be used for the peptide linker:

```
Ser,

Gly-Ser,

Gly-Gly-Ser,

Ser-Gly-Gly,
                                      (SEQ ID NO: 79)
Gly-Gly-Gly-Ser,
                                      (SEQ ID NO: 80)
Ser-Gly-Gly-Gly,
                                      (SEQ ID NO: 81)
Gly-Gly-Gly-Gly-Ser,
                                      (SEQ ID NO: 82)
Ser-Gly-Gly-Gly-Gly,
                                      (SEQ ID NO: 83)
Gly-Gly-Gly-Gly-Gly-Ser,
                                      (SEQ ID NO: 84)
Ser-Gly-Gly-Gly-Gly-Gly,
                                      (SEQ ID NO: 85)
Gly-Gly-Gly-Gly-Gly-Gly-Ser,
                                      (SEQ ID NO: 86)
Ser-Gly-Gly-Gly-Gly-Gly-Gly, (Gly-Gly-Gly-Gly-Ser)$_n$,
and (Ser-Gly-Gly-Gly-Gly)$_n$
``` wherein n is an integer of 1 or larger.

The amino acid sequence of the peptide linker can be appropriately selected by those skilled in the art according to the purpose. For example, the integer n that determines the length of the peptide linker is usually 1 to 5, preferably 1 to 3, more preferably 1 or 2.

Accordingly, in a particularly preferable aspect, examples of the sc(Fv)2 according to the present invention can include the following sc(Fv)2: [VH]-peptide linker (15 amino acids)-[VL]-peptide linker (15 amino acids)-[VH]-peptide linker (15 amino acids)-[VL].

Alternatively, the V regions may be linked using the chemically synthesized linker (chemical cross-linking agent). Cross-linking agents usually used in the cross-link of peptide compounds or the like can be preferably used in the present invention. For example, chemical cross-linking agents as shown below are known in the art. These cross-linking agents are commercially available:
N-hydroxysuccinimide (NHS),
disuccinimidyl suberate (DSS),
bis(sulfosuccinimidyl) suberate (BS3),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSO-COES), and bis[2-(sulfosuccinimidoxycarbonyloxy)ethyl]sulfone (sulfo-BSOCOES), etc.

Three linkers are usually necessary for linking four antibody variable regions. A plurality of linkers having the same sequences may be used, and linkers having different sequences can also be preferably used. In the present invention, the low-molecular antibody is preferably Diabody or sc(Fv)2. Such a low-molecular antibody is formed by the treatment of the whole antibody with an enzyme, for example, papain or pepsin, as described above. Alternatively, such a low-molecular antibody is isolated from the cultures of appropriate host cells transfected with expression vectors having an insert of DNA encoding the antibody fragment (e.g., Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

The antibody of the present invention also encompasses not only monovalent antibodies but also polyvalent antibodies. The polyvalent antibody of the present invention encompasses polyvalent antibodies having antigen-binding sites, all of which are the same as each other or some or all of which are different from each other.

Antibodies conjugated with various molecules such as polyethylene glycol (PEG) may be used as modified antibodies. Alternatively, antibodies conjugated with cytotoxic substances such as chemotherapeutic agents, toxic peptide, or radioactive chemicals may also be used as modified antibodies. Such modified antibodies (hereinafter, referred to as antibody conjugates) can be obtained by chemically modifying the obtained antibody. A method for the antibody modification has already been established in the art. The toxic peptide-conjugated modified antibodies can be obtained by allowing appropriate host cells to express fusion genes of the antibody genes linked in frame with genes encoding the toxic peptides, and then isolating the resulting fusion proteins from the cultures of the cells. As described later, the modified antibody of the present invention may be obtained in a molecular form such as a bispecific antibody designed by a gene recombination technique so as not only to recognize the ITM2A protein but also to recognize a cytotoxic substance such as a chemotherapeutic agent, a toxic peptide, or a radioactive chemical. These antibodies are also encompassed by the "antibody" according to the present invention.

Examples of the chemotherapeutic agent whose cytotoxic activity functions through the conjugation to the ITM2A antibody can include the following chemotherapeutic agents: azaribine, anastrozole, azacytidine, bleomycin, bortezomib, bryostatin-1, busulfan, camptothecin, 10-hydroxycamptothecin, carmustine, Celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, maytansinoid, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, Taxol, testosterone propionate, thalidomide, thioguanine, thiotepa, teniposide, topotecan, uracil mustard, vinblastine, vinorelbine, and vincristine.

In the present invention, the chemotherapeutic agent is preferably a low-molecular chemotherapeutic agent. The low-molecular chemotherapeutic agent is unlikely to interfere with the antibody functions even after its conjugation to the antibody. In the present invention, the low-molecular chemotherapeutic agent usually has a molecular weight of 100 to 2000, preferably 200 to 1000. All of the chemotherapeutic agents exemplified herein are low-molecular chemotherapeutic agents. These chemotherapeutic agents according to the present invention encompass prodrugs that are converted in vivo to active chemotherapeutic agents. The prodrug activation may be enzymatic conversion or nonenzymatic conversion.

Alternatively, the antibody may be modified with the toxic peptide (toxin). Examples of the toxic peptide preferably include the followings:

diphtheria toxin A chain (Langone J. J., et al., Methods in Enzymology (1983) 93, 307-308),

*Pseudomonas* exotoxin (Nature Medicine (1996) 2, 350-353), ricin A chain (Fulton R. J. et al., J. Biol. Chem. (1986) 261, 5314-5319; Sivam G. et al., Cancer Res. (1987) 47, 3169-3173; Cumber A. J. et al., J. Immunol. Methods (1990) 135, 15-24; Wawrzynczak E. J. et al., Cancer Res. (1990) 50, 7519-7562; and Gheeite V. et al., J. Immunol. Methods (1991) 142, 223-230), deglycosylated ricin A chain (Thorpe P. E. et al., Cancer Res. (1987) 47, 5924-5931), abrin A chain (Wawrzynczak E. J. et al., Br. J. Cancer (1992) 66, 361-366; Wawrzynczak E. J., et al. Cancer Res. (1990) 50, 7519-7562; Sivam G., et al. Cancer Res. (1987) 47, 3169-3173; and Thorpe P. E. et al., Cancer Res. (1987) 47, 5924-5931), gelonin (Sivam G. et al., Cancer Res. (1987) 47, 3169-3173; Cumber A. J. et al., J. Immunol. Methods (1990) 135, 15-24; Wawrzynczak E. J. et al. Cancer Res., (1990) 50, 7519-7562; and Bolognesi A. et al., Clin. exp. Immunol. (1992) 89, 341-346), pokeweed anti-viral protein from seeds (PAP-s) (Bolognesi A. et al., Clin. exp. Immunol. (1992) 89, 341-346), bryodin (Bolognesi A. et al., Clin. exp. Immunol. (1992) 89, 341-346), saporin (Bolognesi A., et al., Clin. exp. Immunol. (1992) 89, 341-346), momordin (Cumber A. J. et al., J. Immunol. Methods (1990) 135, 15-24; Wawrzynczak E. J. et al., Cancer Res. (1990) 50, 7519-7562; and Bolognesi A. et al., Clin. exp. Immunol. (1992) 89, 341-346), momorcochin (Bolognesi A. et al., Clin. exp. Immunol. (1992) 89, 341-346), dianthin 32 (Bolognesi A. et al., Clin. exp. Immunol. (1992) 89, 341-346), dianthin 30 (Stirpe F., Barbieri L., FEBS letter (1986) 195, 1-8), modeccin (Stirpe F., Barbieri L., FEBS letter (1986) 195, 1-8), viscumin (Stirpe F., Barbieri L., FEBS letter (1986) 195, 1-8), volkensin (Stirpe F., Barbieri L., FEBS letter (1986) 195, 1-8), dodecandrin (Stirpe F., Barbieri L., FEBS letter (1986) 195, 1-8), tritin (Stirpe F., Barbieri L., FEBS letter (1986) 195, 1-8), luffin (Stirpe F., Barbieri L., FEBS letter (1986) 195, 1-8), and trichokirin (Casellas P., et al., Eur. J. Biochem. (1988) 176, 581-588; and Bolognesi A., et al., Clin. exp. Immunol., (1992) 89, 341-346).

In the present invention, the radioactive chemical refers to a chemical containing a radioisotope. The radioisotope used is not particularly limited, and any radioisotope may be used. Examples thereof can preferably include $^{32}P$, $^{14}C$, $^{125}I$, $^{3}H$, $^{131}I$, $^{186}Re$, and $^{188}Re$.

In another aspect, one or two or more low-molecular chemotherapeutic agents and one or two or more toxic peptides can be used in combination to modify the antibody. The anti-ITM2A antibody can be conjugated to the low-molecular chemotherapeutic agent via a covalent or noncovalent bond. Such a chemotherapeutic agent-conjugated antibody is prepared by a method known in the art.

A proteinous agent or toxin can be conjugated to the antibody by a genetic engineering approach. Specifically, for example, the anti-ITM2A antibody-encoding DNAs are fused in frame with DNAs encoding the toxic peptides, and the resulting fused DNAs can be incorporated into expression vectors to construct recombinant vectors. The vectors are introduced into appropriate host cells, and the resulting transformed cells are cultured so that the DNA inserts are expressed. In this way, toxic peptide-conjugated anti-ITM2A antibodies can be obtained as fusion proteins. In the case of obtaining such antibody-fusion proteins, the proteinous agent or toxin is generally conjugated to the C-terminal side of each antibody. A peptide linker may be allowed to intervene between the antibody and the proteinous agent or toxin.

The antibody of the present invention further encompasses bispecific antibodies. The bispecific antibodies refer to antibodies containing, in the same antibody molecule, variable regions that recognize different epitopes. The bispecific antibody according to the present invention can have antigen-binding sites that recognize different epitopes on the ITM2A molecule. When such bispecific antibody molecules are to bind to ITM2A, two or more molecules of the bispecific antibody can bind to one ITM2A molecule. As a result, the bispecific antibodies, if having cytotoxic activities, can be expected to recruit a larger number of effector cells, resulting in stronger cytotoxic effect.

Alternatively, a bispecific antibody having antigen-binding sites, one of which binds to ITM2A and the other of which binds to a cytotoxic substance may be used in the present invention. The cytotoxic substance specifically encompasses, for example, chemotherapeutic agents, toxic peptides, and radioactive chemicals. Such a bispecific antibody binds to ITM2A-expressing cells, while capturing the cytotoxic substance. As a result, the cytotoxic substance can be allowed to directly act on the ITM2A-expressing cells. Specifically, use of the bispecific antibody that recognizes ITM2A as well as the cytotoxic substance can specifically damage tumor cells, resulting in the inhibited growth of the tumor cells.

Also, a bispecific antibody that binds to ITM2A as well as an antigen other than ITM2A expressed in tumor cells may be used in the present invention. For example, a bispecific antibody that binds to ITM2A and an antigen that is specifically expressed on the surface of target cancer cells, as with ITM2A, but is different from ITM2A, can be used.

The bispecific antibody is produced by a method known in the art. For example, two types of antibodies differing in antigen recognized thereby can be bound to prepare the bispecific antibody. Each of the antibodies bound may be a ½ molecule having H and L chains or may be a ¼ molecule consisting of H chains. Alternatively, different monoclonal antibody-producing hybridomas may be fused to prepare fusion cells producing bispecific antibodies. The bispecific antibody can also be prepared by a genetic engineering approach.

The antigen binding activity of the antibody (Antibodies A Laboratory Manual. Ed Harlow, David Lane, Cold Spring Harbor Laboratory, 1988) can be determined using means known in the art. For example, ELISA (enzyme-linked immunosorbent assay), EIA (enzyme immunoassay), RIA (radioimmunoassay), flow cytometry such as FACS, or fluoroimmunoassay can be preferably used.

The antibody of the present invention also encompasses an antibody having a modified sugar chain of the antibody of the present invention. The cytotoxic activities of antibodies are known to be enhanced by the modification of their sugar chains. For example, the following antibodies are known in the art as the antibody having a modified sugar chain:
glycosylated antibodies (WO1999054342, etc.),
antibodies deficient in fucose added to their sugar chains (WO2000061739, WO2002031140, WO2006067913, etc.), and
antibodies having a sugar chain having bisecting GlcNAc (WO2002079255, etc.).

The antibody of the present invention used for the therapeutic purpose is preferably an antibody having a cytotoxic activity. Examples of the cytotoxic activity according to the present invention preferably include antibody-dependent cell-mediated cytotoxicity (ADCC) and complement-dependent cytotoxicity (CDC) activities. Another example of the antibody having a cytotoxic activity includes an antibody having both ADCC and CDC activities. In the present invention, the CDC activity refers to a cytotoxic activity mediated by the complement system. On the other hand, the ADCC activity refers to an activity of damaging target cells by Fcγ receptor-expressing cells (immunocytes, etc.) as a result of binding of the Fcγ receptor-expressing cells (immunocytes, etc.) via the Fcγ receptors to the Fc domains of antibodies specifically attached to the cell surface antigens of the target cells.

Whether or not the anti-ITM2A antibody has an ADCC activity or has a CDC activity can be determined by a method known in the art (e.g., Current protocols in Immunology, (1993) Chapter 7. Immunologic studies in Humans, Editor, John E, Coligan et al., John Wiley & Sons, Inc.).

Specifically, effector cells, a complement solution, and target cells are first prepared.

(1) Preparation of Effector Cells

The spleens are excised from CBA/N mice or the like, and spleen cells are separated therefrom in an RPMI1640 medium (manufactured by Invitrogen Corp.). The spleen cells can be washed with this medium containing 10% fetal bovine serum (FBS, manufactured by HyClone Laboratories, Inc.) and then adjusted to a cell concentration of $5 \times 10^6$ cells/ml to prepare effector cells.

(2) Preparation of Complement Solution

Baby Rabbit Complement (manufactured by CEDARLANE Laboratories Ltd.) can be diluted 10-fold with a medium (manufactured by Invitrogen Corp.) containing 10% FBS to prepare a complement solution.

(3) Preparation of Target Cells

Cells expressing ITM2A proteins can be cultured at 37° C. for 1 hour, together with 0.2 mCi 51Cr-sodium chromate (manufactured by GE Healthcare Bio-Sciences Corp.), in a DMEM medium containing 10% FBS to radiolabel the target cells. Cells transformed with ITM2A protein-encoding genes, Ewing's sarcoma cells, acute myeloid leukemia cells, T cell lymphoma cells, T cells lymphocytic leukemia cells, or the like can be used as the cells expressing ITM2A proteins. The cells thus radiolabeled can be washed three times with an RPMI1640 medium containing 10% FBS and adjusted to a cell concentration of $2 \times 10^5$ cells/ml to prepare the target cells.

The ADCC or CDC activity can be assayed by a method described below. For the ADCC activity assay, a U-bottom 96-well plate (manufactured by Becton, Dickinson and Company) supplemented with the target cells and the anti-ITM2A antibody (each 50 µl/well) is left standing for 15 minutes on ice. Then, 100 µl of the effector cells is added to each well of the plate, and the resulting plate is incubated for 4 hours in a $CO_2$ incubator. The final concentration of the antibody is adjusted to 0 or 10 µg/ml. After the incubation, the radioactivity of 100 µl of the supernatant recovered from each well is measured using a gamma counter (COBRA II AUTO-GAMMA, MODEL D5005, manufactured by Packard Instrument Company). The cytotoxic activity (%) can be calculated on the basis of the calculation expression $(A-C)/(B-C) \times 100$ using the following values obtained by such measurement:

A represents radioactivity (cpm) from each sample,
B represents radioactivity (cpm) from a sample supplemented with 1% NP-40 (manufactured by Nacalai Tesque, Inc.), and
C represents radioactivity (cpm) from a sample containing only the target cells.

For the CDC activity assay, a flat-bottomed 96-well plate (manufactured by Becton, Dickinson and Company) supplemented with the target cells and the anti-ITM2A antibody (each 50 µl/well) is left standing for 15 minutes on ice. Then, 100 µl of the complement solution is added to each well of the plate, and the resulting plate is incubated for 4 hours in a $CO_2$ incubator. The final concentration of the antibody is adjusted to 0 or 3 µg/ml. After the incubation, the radioactivity of 100 µl of the supernatant recovered from each well is measured using a gamma counter. The cytotoxic activity based on the CDC activity can be calculated according to a calculation expression similar to that of the ADCC activity.

In the case of assaying the cytotoxic activity of the antibody conjugate, a flat-bottomed 96-well plate (manufactured by Becton, Dickinson and Company) supplemented with the target cells and the anti-ITM2A antibody conjugate (each 50 µl/well) is left standing for 15 minutes on ice. Subsequently, the plate is incubated for 1 to 4 hours in a $CO_2$ incubator. The final concentration of the antibody is adjusted to 0 or 3 µg/ml. After the incubation, the radioactivity of 100 µl of the supernatant recovered from each well is measured using a gamma counter. The cytotoxic activity of the antibody conjugate can be calculated according to a calculation expression similar to that of the ADCC activity assay.

In an alternative aspect, examples of the antibody used in the present invention also preferably include an antibody having an internalization activity. In the present invention, the "antibody having an internalization activity" means an antibody that is transported into a cell (cytoplasm, vesicle, any other organelle, etc.) through its binding to ITM2A on the cell surface.

Whether or not the antibody has an internalization activity can be confirmed by a method generally known to those skilled in the art and can be confirmed by, for example, a method involving contacting labeling material-bound anti-ITM2A antibodies with ITM2A-expressing cells and confirming whether or not the labeling material is incorporated into the cells by the contact, or a method involving contacting cytotoxic substance-conjugated anti-ITM2A antibodies with ITM2A-expressing cells and confirming whether or not the death of the ITM2A-expressing cells is induced by the contact. More specifically, whether or not the antibody has an internalization activity can be confirmed by a method described in, for example, Examples below.

For example, the cytotoxic substance-conjugated antibody having an internalization activity can be used as a pharmaceutical composition such as an anticancer agent.

An arbitrary antibody binding to ITM2A can be used as the antibody of the present invention. Preferable examples of the antibody can include antibodies (1) to (25) shown below. These antibodies may be, for example, whole antibodies, low-molecular antibodies, animal antibodies, chimeric antibodies, humanized antibodies, or human antibodies:

(1) an antibody comprising an H chain having the amino acid sequence represented by SEQ ID NO: 3 as CDR1, the amino acid sequence represented by SEQ ID NO: 4 as CDR2, and the amino acid sequence represented by SEQ ID NO: 5 as CDR3;

(2) an antibody comprising an L chain having the amino acid sequence represented by SEQ ID NO: 6 as CDR1, the amino acid sequence represented by SEQ ID NO: 7 as CDR2, and the amino acid sequence represented by SEQ ID NO: 8 as CDR3;

(3) an antibody comprising the H chain described in (1) and the L chain described in (2);

(4) an antibody comprising an H chain having the amino acid sequence represented by SEQ ID NO: 9 as CDR1, the amino acid sequence represented by SEQ ID NO: 10 as CDR2, and the amino acid sequence represented by SEQ ID NO: 11 as CDR3;

(5) an antibody comprising an L chain having the amino acid sequence represented by SEQ ID NO: 12 as CDR1, the amino acid sequence represented by SEQ ID NO: 13 as CDR2, and the amino acid sequence represented by SEQ ID NO: 14 as CDR3;

(6) an antibody comprising the H chain described in (4) and the L chain described in (5);

(7) an antibody comprising an H chain having the amino acid sequence represented by SEQ ID NO: 15 as CDR1, the amino acid sequence represented by SEQ ID NO: 16 as CDR2, and the amino acid sequence represented by SEQ ID NO: 17 as CDR3;

(8) an antibody comprising an L chain having the amino acid sequence represented by SEQ ID NO: 18 as CDR1, the amino acid sequence represented by SEQ ID NO: 19 as CDR2, and the amino acid sequence represented by SEQ ID NO: 20 as CDR3;

(9) an antibody comprising the H chain described in (7) and the L chain described in (8);

(10) an antibody comprising an H chain having the amino acid sequence represented by SEQ ID NO: 21 as CDR1, the amino acid sequence represented by SEQ ID NO: 22 as CDR2, and the amino acid sequence represented by SEQ ID NO: 23 as CDR3;

(11) an antibody comprising an L chain having the amino acid sequence represented by SEQ ID NO: 24 as CDR1, the amino acid sequence represented by SEQ ID NO: 25 as CDR2, and the amino acid sequence represented by SEQ ID NO: 26 as CDR3;

(12) an antibody comprising the H chain described in (10) and the L chain described in (11);

(13) the antibody described in any of (1) to (12) which is a chimeric antibody;

(14) the antibody described in any of (1) to (12) which is a humanized antibody;
(15) the antibody described in (1) or (3), comprising the amino acid sequence represented by SEQ ID NO: 28;
(16) the antibody described in (2) or (3), comprising the amino acid sequence represented by SEQ ID NO: 30;
(17) the antibody described in (4) or (6), comprising the amino acid sequence represented by SEQ ID NO: 32;
(18) the antibody described in (5) or (6), comprising the amino acid sequence represented by SEQ ID NO: 34;
(19) the antibody described in (7) or (9), comprising the amino acid sequence represented by SEQ ID NO: 36;
(20) the antibody described in (8) or (9), comprising the amino acid sequence represented by SEQ ID NO: 38;
(21) the antibody described in (10) or (12), comprising the amino acid sequence represented by SEQ ID NO: 40;
(22) the antibody described in (11) or (12), comprising the amino acid sequence represented by SEQ ID NO: 42;
(23) the antibody described in any of (15) to (22) which is a chimeric antibody;
(24) an antibody that has an amino acid sequence of the antibody described in any of (1) to (23) with a substitution, deletion, addition, and/or insertion of one or more amino acid(s) and has an activity equivalent to or a binding activity equivalent to that of the antibody; and
(25) an antibody capable of binding to an epitope to which a second antibody binds, wherein the second antibody is the antibody described in any of (1) to (23).

In the present invention, the phrase "having an activity equivalent to that of the antibody of the present invention" means that a cytotoxic activity against ITM2A-expressing cells is equivalent to that of the antibody of the present invention. In the present invention, the phrase "having a binding activity equivalent to that of the antibody of the present invention" means that an ITM2A binding activity is equivalent to that of the antibody of the present invention.

A method for introducing a mutation to a polypeptide is one of methods well known to those skilled in the art for preparing a polypeptide functionally equivalent to a certain polypeptide. For example, those skilled in the art can appropriately introduce a mutation in the antibody of the present invention using site-directed mutagenesis (Hashimoto-Gotoh, T. et al. Gene (1995) 152, 271-275; Zoller, M J, and Smith, M. Methods Enzymol., (1983) 100, 468-500; Kramer, W. et al. Nucleic Acids Res., (1984) 12, 9441-9456; Kramer W, and Fritz H J Methods. Enzymol., (1987) 154, 350-367; Kunkel, T A Proc. Natl. Acad. Sci. USA., (1985) 82, 488-492; and Kunkel, Methods Enzymol., (1988) 85, 2763-2766) or the like and thereby prepare an antibody functionally equivalent to the antibody concerned. Amino acid mutations may occur in the natural world. Such an antibody that has an amino acid sequence of the antibody of the present invention with a mutation of one or more amino acid(s) and has an activity functionally equivalent to or a binding activity equivalent to that of the antibody concerned is also encompassed by the antibody of the present invention.

The number of amino acids mutated in such a variant is usually within 50 amino acids, preferably within 30 amino acids, more preferably within 15 amino acids or within 10 amino acids (e.g., within 9, 8, 7, 6, 5, 4, 3, 2, or 1 amino acid(s)).

For amino acid residues to be mutated, this mutation is preferably performed conservatively between amino acids having the same side chain properties. For example, the following classification based on the properties of amino acid side chains has been established:

hydrophobic amino acids (A, I, L, M, F, P, W, Y, and V),
hydrophilic amino acids (R, D, N, C, E, Q, G, H, K, S, and T),
amino acids having an aliphatic side chain (G, A, V, L, I, and P),
amino acids having a hydroxy group-containing side chain (S, T, and Y),
amino acids having a sulfur atom-containing side chain (C and M),
amino acids having a side chain containing carboxylic acid and amide (D, N, E, and Q),
amino acids having a base-containing side chain (R, K, and H), and
amino acids having an aromatic group-containing side chain (H, F, Y, and W)
(all symbols within the parentheses represent single letter codes of amino acids).

A polypeptide having an amino acid sequence modified from a certain amino acid sequence by the deletion and/or addition of one or more amino acid residue(s) and/or the substitution thereof by other amino acids is already known to maintain the biological activity of the original polypeptide (Mark, D. F. et al., Proc. Natl. Acad. Sci. USA (1984) 81, 5662-5666; Zoller, M. J. and Smith, M., Nucleic Acids Research (1982) 10, 6487-6500; Wang, A. et al., Science (1984) 224, 1431-1433; and Dalbadie-McFarland, G. et al., Proc. Natl. Acad. Sci. USA (1982) 79, 6409-6413). Specifically, when amino acids in an amino acid sequence constituting a certain polypeptide are substituted by amino acids classified in the same group thereas, it is generally said that the polypeptide is likely to maintain its activity. In the present invention, the substitution between amino acids within the same amino acid group described above is referred to as conservative substitution.

The present invention also provides an antibody binding to the same epitope as that to which the anti-ITM2A antibody disclosed herein binds. Specifically, the present invention relates to an antibody binding to the same epitope as that to which BE5-1, BE6-1, BE7-1-1, or BE13-1 binds, and use thereof. Such an antibody can be obtained, for example, by a method show below.

Whether a test antibody shares an epitope with a certain antibody can be confirmed on the basis of their competition for the same epitope. The competition between the antibodies is detected by cross-blocking assay or the like. The cross-blocking assay is preferably, for example, competitive ELISA assay.

Specifically, the cross-blocking assay involves preincubating ITM2A proteins coated on the wells of a microtiter plate in the presence or absence of a candidate competing antibody and then adding the anti-ITM2A antibody of the present invention to the wells. The amount of the anti-ITM2A antibody of the present invention bound to the ITM2A protein in each well indirectly correlates with the binding capability of the candidate competing antibody (test antibody) that competes therewith for binding to the same epitope. Specifically, correlation is confirmed such that the higher affinity of the test antibody for the same epitope results in the smaller amount of the anti-ITM2A antibody of the present invention bound to the ITM2A protein-coated well and instead, the larger amount of the test antibody bound to the ITM2A protein-coated well.

The amount of each antibody bound to the well can be easily determined by labeling the antibody in advance. For example, the amount of a biotinylated antibody can be determined using an avidin-peroxidase conjugate and an appropriate substrate. The cross-blocking assay using enzyme (e.g., peroxidase) labeling is particularly called competitive ELISA assay. The antibody may be labeled with any of other detectable or measurable labeling materials. Specifically, for example, radiolabeling or fluorescent labeling is known in the art.

Alternatively, the cross-blocking assay is preferably competitive FACS assay.

Specifically, the competitive FACS assay employs cells containing expressed ITM2A proteins instead of ITM2A proteins coated on the wells of a microtiter plate in the competitive ELISA assay. The cells containing expressed ITM2A proteins are preincubated in the presence or absence of a candidate competing antibody. Then, the biotinylated anti-ITM2A antibody of the present invention is added to the wells. Fluorescence can be detected using a streptavidin-fluorescein conjugate to determine the competition between the antibodies. The cross-blocking assay using flow cytometry is particularly called competitive FACS assay. The antibody can be preferably labeled with any of other detectable or measurable fluorescent labeling materials.

When the test antibody contains constant regions derived from an organism species different from that of the anti-ITM2A antibody of the present invention, the antibody (derived from any organism species) bound to the well can be assayed using a labeled antibody that recognizes the constant region of the antibody of the organism species. Alternatively, even in the case of detecting the binding of antibodies derived from the same organism species but differing in class, each antibody bound to the well can be assayed using an antibody specifically binding to the antibody of each class.

Provided that the candidate antibody can block the binding of the anti-ITM2A antibody by at least 20%, preferably at least 30%, more preferably at least 40%, even more preferably 50%, compared with the binding activity obtained as a result of the control test conducted in the absence of the candidate competing antibody, this candidate competing antibody is determined as an antibody that binds to substantially the same epitope as that to which the anti-ITM2A antibody of the present invention binds or as an antibody that competes therewith for the binding to the same epitope. For the epitope assay, the constant region of the antibody of the present invention may be replaced with the same constant region as that of the test antibody.

The epitope to which the anti-ITM2A antibody of the present invention binds can be appropriately determined by the method described above. Preferably, the epitope can be present in a fragment comprising the extracellular region of the ITM2A protein. Examples of such a fragment also preferably include a polypeptide consisting of amino acids 75 to 263 in the ITM2A protein represented by SEQ ID NO: 1. In another aspect, examples of the fragment preferably include a polypeptide consisting of amino acids 75 to 227 in the ITM2A protein represented by SEQ ID NO: 1.

Pharmaceutical Composition

In an alternative aspect, the present invention provides a pharmaceutical composition comprising the antibody binding to ITM2A protein as an active ingredient. The present invention also relates to a cell growth inhibitor, particularly, an anticancer agent, comprising the antibody binding to ITM2A protein as an active ingredient. The cell growth inhibitor and the anticancer agent of the present invention are preferably administered to a subject having cancer or possibly having cancer. As shown later in Examples, ITM2A is expressed at a low level in normal cells, but is overexpressed in cancer cells. Therefore, the administration of the anti-ITM2A antibody probably produces cancer cell-specific cytotoxic effect.

The anti-ITM2A antibody used in the pharmaceutical composition (e.g., the anticancer agent) of the present invention is not particularly limited and may be any anti-ITM2A antibody. For example, any of the anti-ITM2A antibodies described above can be preferably used.

In the present invention, the phrase "comprising the antibody binding to ITM2A as an active ingredient" means containing the anti-ITM2A antibody as a main active ingredient and is not intended to limit the content of the anti-ITM2A antibody.

When the disease targeted by the pharmaceutical composition of the present invention is cancer, the targeted cancer is not particularly limited as long as the ITM2A protein is expressed in the cancer. The cancer is preferably Ewing's sarcoma or blood cancer such as T cell leukemia, T cell lymphoma, acute myeloid leukemia, B cell tumor, or multiple myeloma, particularly preferably Ewing's sarcoma. Among the Ewing's sarcomas, Ewing's sarcoma having t(11;22)(q24;q12) chromosomal translocation may be preferably targeted. Such cancer may be any of primary foci and metastatic foci.

In the present invention, a method known in the art such as FISH or PCR can be appropriately adopted as a cell damaging method or for determining whether or not Ewing's sarcoma cells whose growth is to be inhibited have t(11;22)(q24;q12) chromosomal translocation.

In order to determine whether to have the t(11;22)(q24;q12) chromosomal translocation by the FISH method, for example, a probe for EWS gene detection and a probe for FLI-1 gene detection separately labeled so as to emit different fluorescences are hybridized to test tissue samples immobilized by a method known in the art. The presence of the t(11;22)(q24;q12) chromosomal translocation can be confirmed by determining whether or not fusion signals of these fluorescences are detected as a result of the hybridization.

Alternatively, FISH using two probes for respectively detecting portions of a chromosome split by the translocation may also be appropriately adopted for determining whether to have the t(11;22)(q24;q12) chromosomal translocation. Specifically, these two probes (e.g., a set of probes for detecting the EWS gene split by the translocation or a set of probes for FLI-1 gene detection) separately labeled so as to emit different fluorescences are hybridized to test tissue samples immobilized by a method known in the art. The presence of the t(11;22)(q24;q12) chromosomal translocation can be confirmed by determining whether or not split signals of these fluorescences are detected as a result of the hybridization.

In order to determine whether to have the t(11;22)(q24;q12) chromosomal translocation by the PCR method, a set of two primers is designed such that the EWS gene and the FLI-1 gene can be detected. The primers are designed such that a fusion gene formed by the translocation is amplified as a result of PCR using the set of the primers. The presence of the t(11;22)(q24;q12) chromosomal translocation can be confirmed by detecting the PCR amplification of the fusion gene formed by the translocation.

Alternatively, a set of two primers that allow detection of fragments of a chromosome split by the translocation is designed for determining whether to have the t(11;22)(q24;q12) chromosomal translocation. For example, PCR is carried out using a set of primers for detecting the EWS gene split by the translocation or a set of primers for FLI-1 gene detection, and a test tissue sample as a template. The presence of the t(11;22)(q24;q12) chromosomal translocation can be confirmed provided that chromosomal fragments formed by PCR using a sample free from the translocation as a template are not detected in the PCR products obtained with the test tissue sample as a template.

The pharmaceutical composition of the present invention can be administered either orally or parenterally to a patient. Parenteral administration is preferable. Specific examples of such an administration method preferably include injection, transnasal, pulmonary, and transdermal administrations. Examples of the injection administration include intravenous, intramuscular, intraperitoneal, and subcutaneous injections, through which the pharmaceutical composition of the present invention can be administered systemically or locally. The administration method can be appropriately selected according to the age or symptoms of the patient. The dose of the pharmaceutical composition of the present invention can be selected from among the range of, for example, 0.0001 mg to 1000 mg per kg body weight per dosing. Alternatively, the dose in each patient may be selected from among the range of, for example, 0.001 to 100000 mg per body. However, the pharmaceutical composition of the present invention is not limited by these doses.

The pharmaceutical composition of the present invention can be formulated according to a routine method (e.g., Remington's Pharmaceutical Science, Latest edition, Mark Publishing Company, Easton, U.S.A). The pharmaceutical composition preferably used may additionally contain pharmaceutically acceptable carriers or additives. Examples of such carriers or additives include, but not limited thereto, surfactants, excipients, coloring agents, flavoring agents, preservatives, stabilizers, buffers, suspending agents, tonicity agents, binders, disintegrants, lubricants, flow promoters, and corrigents. Other carriers routinely used may be appropriately used. Specific examples of such carriers routinely used can include light anhydrous silicic acid, lactose, crystalline cellulose, mannitol, starch, carmellose calcium, carmellose sodium, hydroxypropylcellulose, hydroxypropylmethylcellulose, polyvinyl acetal diethylaminoacetate, polyvinylpyrrolidone, gelatin, medium chain fatty acid triglyceride, polyoxyethylene hydrogenated castor oil 60, white sugar, carboxymethylcellulose, corn starch, and inorganic salts.

The present invention also provides a method for damaging ITM2A-expressing cells or inhibiting the growth of ITM2A-expressing cells, comprising contacting the ITM2A-expressing cells with the antibody binding to ITM2A protein.

The antibody used in the method of the present invention is not particularly limited, and, for example, any of the antibodies described above may be used. The cells to which the anti-ITM2A antibody binds are not particularly limited as long as ITM2A is expressed in the cells. The ITM2A-expressing cells according to the present invention are preferably cancer cells, more preferably Ewing's sarcoma cells or cells of blood cancer such as T cell leukemia, T cell lymphoma, acute myeloid leukemia, B cell tumor, or multiple myeloma. The method of the present invention can be applied to any of primary foci and metastatic foci of these cancers. The cancer cells are more preferably Ewing's sarcoma cells or metastatic Ewing's sarcoma cells. Among the Ewing's sarcoma cells, Ewing's sarcoma cells having t(11;22)(q24;q12) chromosomal translocation may be preferably targeted. Such Ewing's sarcoma cells having the chromosomal translocation may be located in any of primary foci and metastatic foci.

In the present invention, a method known in the art such as FISH or PCR can be appropriately adopted as a cell damaging method or for determining whether or not Ewing's sarcoma cells whose growth is to be inhibited have t(11;22)(q24;q12) chromosomal translocation.

In order to determine whether to have the t(11;22)(q24;q12) chromosomal translocation by the FISH method, for example, a probe for EWS gene detection and a probe for FLI-1 gene detection separately labeled so as to emit different fluorescences are hybridized to test tissue samples immobilized by a method known in the art. The presence of the t(11;22)(q24;q12) chromosomal translocation can be confirmed by determining whether or not adjacent or fusion signals of these fluorescences are detected as a result of the hybridization.

Alternatively, FISH using two probes for respectively detecting portions of a chromosome split by the translocation may also be appropriately adopted for determining whether to have the t(11;22)(q24;q12) chromosomal translocation. Specifically, these two probes (e.g., a set of probes for detecting the EWS gene split by the translocation or a set of probes for FLI-1 gene detection) separately labeled so as to emit different fluorescences are hybridized to test tissue samples immobilized by a method known in the art. The presence of the t(11;22)(q24;q12) chromosomal translocation can be confirmed by determining whether or not split signals of these fluorescences are detected as a result of the hybridization.

In order to determine whether to have the t(11;22)(q24;q12) chromosomal translocation by the PCR method, a set of two primers is designed such that the EWS gene and the FLI-1 gene can be detected. The primers are designed such that a fusion gene formed by the translocation is amplified as a result of PCR using the set of the primers. The presence of the t(11;22)(q24;q12) chromosomal translocation can be confirmed by detecting the PCR amplification of the fusion gene formed by the translocation.

Alternatively, a set of two primers that allow detection of fragments of a chromosome split by the translocation is designed for determining whether to have the t(11;22)(q24;q12) chromosomal translocation. For example, PCR is carried out using a set of primers for detecting the EWS gene split by the translocation or a set of primers for FLI-1 gene detection, and a test tissue sample as a template. The presence of the t(11;22)(q24;q12) chromosomal translocation can be confirmed provided that chromosomal fragments formed by PCR using a sample free from the translocation as a template are not detected in the PCR products obtained with the test tissue sample as a template.

In the present invention, the "contact" is performed, for example, by adding the antibody to cultures of ITM2A-expressing cells cultured in vitro. In the present invention, the "contact" is also performed by administering the antibody to non-human animals implanted with ITM2A-expressing cells in their bodies or to animals endogenously having ITM2A-expressing cancer cells.

Methods shown below are preferably used for evaluating or determining cytotoxicity caused against the ITM2A-expressing cells by the contact of the anti-ITM2A antibody. Examples of the methods for evaluating or determining the cytotoxic activity in vitro can include the antibody-dependent cell-mediated cytotoxicity (ADCC) and complement-dependent cytotoxicity (CDC) activity assay methods described above. Whether or not the anti-ITM2A antibody has an ADCC activity or has a CDC activity can be determined by a method known in the art (e.g., Current protocols in Immunology, Chapter 7. Immunologic studies in Humans, Editor, John E, Coligan et al., John Wiley & Sons, Inc., (1993)). In the activity assay, a binding antibody that has an isotype identical to that of the anti-ITM2A antibody and does not have the cytotoxic activity is used as a control antibody in the same way as in the anti-ITM2A antibody. When the anti-ITM2A antibody exhibits a stronger cytotoxic activity than that of the control antibody, the anti-ITM2A antibody can be determined to have the activity.

The isotype of an antibody is defined by the sequence of the H chain constant region in the amino acid sequence of this antibody. The antibody isotype is finally determined depending on class switching caused by genetic recombination on the chromosome during the maturation of antibody-producing B cells in vivo. Difference in isotype is reflected by the difference between the physiological/pathological functions of antibodies. Specifically, it is known that, for example, the strength of the cytotoxic activity is influenced not only by the expression level of the antigen but also by the isotype of the antibody. Thus, for the cytotoxic activity assay described above, the antibody used as a control preferably has an isotype identical to that of the test antibody.

In order to evaluate or determine the cytotoxic activity in vivo, for example, ITM2A-expressing cancer cells are intradermally or subcutaneously transplanted to non-human test animals. Then, the test antibody is intravenously or intraperitoneally administered thereto on a daily basis or at a few day-intervals from the administration day or the next day. The cytotoxic activity of the test antibody can be determined by measuring tumor sizes over time. A control antibody having an isotype identical thereto is administered, as in the in vitro evaluation. When the test anti-ITM2A antibody-administered group exhibits a significantly smaller tumor size than that of the control antibody-administered group, the test anti-ITM2A antibody can be determined to have the cytotoxic activity. In the case of using mice as the non-human test animals, nude (nu/nu) mice can be preferably used, which are genetically deficient in the thymus gland and thus lack the functions of T lymphocytes. The use of these mice excludes the involvement of the endogenous T lymphocytes of the test animals in the evaluation or determination of the cytotoxic activities of administered antibodies.

In one aspect, the method of the present invention provides the diagnosis of cancer by detecting ITM2A protein in a test sample. In this aspect, preferably, the extracellular region of the ITM2A protein is detected. An antibody that recognizes the ITM2A protein can be preferably used in the detection of the ITM2A protein.

One specific example of the diagnosis method of the present invention can include a method for diagnosing cancer, comprising the following steps:
(a) providing a sample collected from a test subject; and
(b) detecting ITM2A protein contained in the collected sample using an antibody binding to the ITM2A protein.

In the present invention, the detection encompasses quantitative or qualitative detection. Examples of the qualitative detection can include the following assays: assay to simply determine the presence or absence of the ITM2A protein, assay to determine the presence or absence of more than a predetermined amount of the ITM2A protein, and
assay to compare the amount of the ITM2A protein with that contained in another sample (e.g., a control sample).

On the other hand, examples of the quantitative detection can include the measurement of an ITM2A protein concentration and the measurement of the amount of the ITM2A protein.

The test sample according to the present invention is not particularly limited as long as the sample possibly contains the ITM2A protein. Specifically, samples collected from living bodies such as mammals are preferable. Samples collected from humans are more preferable. Specific examples of the test sample can include blood, interstitial fluid, plasma, extravascular fluid, cerebrospinal fluid, synovial fluid, pleural fluid, serum, lymph, saliva, urine, tissues, ascitic fluid, and intraperitoneal lavage. The sample is preferably a sample obtained from the test sample, such as a preparation in which tissues or cells collected from a living body are fixed, or cell cultures.

The cancer diagnosed by the present invention is not particularly limited and may be any cancer. Specific examples thereof can include Ewing's sarcoma and blood cancer such as T cell leukemia, T cell lymphoma, acute myeloid leukemia, B cell tumor, and multiple myeloma. In the present invention, any of primary foci and metastatic foci of these cancers can be diagnosed. Among the Ewing's sarcoma cells, Ewing's sarcoma having t(11;22)(q24;q12) chromosomal translocation may be diagnosed. Such Ewing's sarcoma having the chromosomal translocation may be any of primary foci and metastatic foci.

In the present invention, the cancer is diagnosed using, as an index, the level of the ITM2A protein detected in the test sample. Specifically, when the amount of the ITM2A protein detected in the test sample is larger than that of a negative control or a healthy individual, the test subject is shown to have cancer or be highly likely to have cancer in the future. Specifically, the present invention relates to a method for diagnosing cancer, comprising the following steps:
(1) detecting the expression level of ITM2A in a biological sample collected from a test subject, and
(2) comparing the expression level of ITM2A detected in step (1) with that of a control, wherein when the expression level of ITM2A is higher than that of the control, the test subject is determined to have cancer.

In the present invention, the control refers to a reference sample for comparison and encompasses negative controls and biological samples of healthy individuals. The negative controls can be obtained by collecting biological samples of healthy individuals and mixing them, if necessary. The expression level of ITM2A in the control can be detected in parallel with the detection of the expression level of ITM2A in the biological sample of the test subject. Alternatively, the expression level of ITM2A in a large number of biological samples of healthy individuals may be detected in advance to statistically determine the standard expression level in the healthy individuals. Such statistically determined values are also used as control values for the expression level of ITM2A in the test biological sample. Specifically, for example, mean±2×standard deviation (S.D.) or mean±3×standard deviation (S.D.) can be used as the standard value. Statistically, the mean±2×standard deviation (S.D.) and the mean±3×standard deviation (S.D.) include values of 80% and 90% of the healthy individuals, respectively.

Alternatively, the expression level of ITM2A in the control may be set using an ROC curve. The ROC curve, or receiver operating characteristic curve, is a graph showing detection sensitivity in the ordinate and false positive rates (i.e., "1−specificity") in the abscissa. In the present invention, the ROC curve can be obtained by plotting changes in sensitivity and false positive rate at a series of varying reference values for determining the expression level of ITM2A in the biological sample.

The "reference value" for obtaining the ROC curve is a numeric value temporarily used for statistical analysis. In general, the "reference value" for obtaining the ROC curve is serially varied within a range which can cover all selectable reference values. For example, the reference value can be varied between the minimal and maximal measured values of ITM2A in a population to be analyzed.

A standard value that can be expected to offer the desired detection sensitivity and precision can be selected on the basis of the obtained ROC curve. The standard value statistically set on the basis of the ROC curve or the like is also called a cut-off value. In a method for detecting cancer on the basis of the cut-off value, step (2) described above comprises comparing the expression level of ITM2A detected in step (1), with the cut-off value. Then, when the expression level of ITM2A detected in step (1) is higher than the cut-off value, cancer is detected in the test subject.

In the present invention, the expression level of ITM2A can be determined by an arbitrary method. Specifically, the expression level of ITM2A can be determined by evaluating the amount of the ITM2A protein and the biological activity of the ITM2A protein. The amount of the ITM2A protein can be determined by the method as described herein.

In the present invention, an arbitrary animal species expressing the ITM2A protein can be selected as the test subject. For example, many non-human mammalian individuals such as rhesus macaque (*Macaca mulatta*) (ENSMMUG00000003564), common marmoset (*Callithrix jacchus*) (ENSCJAG00000009591), Sumatran orangutan (*Pongo abelii*) (LOC100431628), rabbit (*Oryctolagus cuniculus*) (ENSOCUG00000008651), horse (*Equus caballus*) (ENSECAG00000011335), mouse (*Mus musculus*) (ENSMUSG00000031239), giant panda (*Ailuropoda melanoleuca*) (LOC100476516), rat (*Rattus norvegicus*) (ENSRNOG00000002365), pig (*Sus scrofa*) (ENSSSCG00000012448), and chicken (*Gallus gallus*) (ENSGALG00000004107) are known to express the ITM2A protein. Thus, these animals are encompassed by the test subject according to the present invention. The test subject is particularly preferably a human. When a non-human animal is used as the test subject, the ITM2A protein of the animal species is detected.

The anti-ITM2A antibody may be used for detecting the ITM2A protein of a non-human animal species. In such a case, an anti-ITM2A antibody binding to only the ITM2A protein of the animal species may be used. Alternatively, an anti-ITM2A antibody capable of binding to not only the ITM2A protein derived from the animal species but also the ITM2A protein derived from another animal species, i.e., having so-called cross reactivity, can also be preferably used. The anti-ITM2A antibody may be further used for detecting the human ITM2A protein. In such a case, an anti-ITM2A antibody binding to only human ITM2A as well as an anti-ITM2A antibody capable of binding to both of human ITM2A and the ITM2A protein derived from another animal species can be preferably used.

A method for detecting the ITM2A protein contained in the test sample is not particularly limited and is preferably an immunological detection method using the anti-ITM2A antibody as exemplified below:
radioimmunoassay (RIA),
enzyme immunoassay (EIA),
fluoroimmunoassay (FIA),
luminescent immunoassay (LIA),
immunoprecipitation (IP),
turbidimetric immunoassay (TIA),
Western blot (WB),
immunohistochemical (IHC) method, and
single radial immunodiffusion (SRID).

Among these approaches, the immunohistochemical (IHC) method is a preferable immunological assay method for diagnosing cancer, comprising the step of detecting the ITM2A protein on sections in which tissues or cells obtained from a patient having cancer are fixed. The immunological methods described above, such as the immunohistochemical (IHC) method, are generally known to those skilled in the art.

Specifically, since ITM2A is a membrane protein specifically overexpressed in cancer cells, cancer cells or cancer tissues can be detected using the anti-ITM2A antibody. Cancer cells contained in cells or tissues collected from living bodies can be detected by the immunohistological analysis.

In another preferable aspect, cancer tissues can be detected in vivo by a noninvasive method using the anti-ITM2A antibody. Specifically, the present invention relates to a method for detecting cancer, comprising the steps of: (1) administering, to a test subject, a labeling material (e.g., radioisotope)-labeled antibody binding to ITM2A protein; and (2) detecting the accumulation of the labeling material. The anti-ITM2A antibody can be detectably labeled for tracing the anti-ITM2A antibody administered into the living body. For example, the in vivo behavior of the antibody labeled with a fluorescent or luminescent material or a radioisotope can be traced. The fluorescent or luminescent material-labeled anti-ITM2 antibody can be observed using an endoscope or peritoneoscope. The localization of the anti-ITM2A antibody can be imaged by tracing the radioactivity of the radioisotope. In the present invention, the in vivo localization of the anti-ITM2A antibody represents the presence of cancer cells.

A positron-emitting nuclide can be used as the radioisotope for labeling the anti-ITM2A antibody used for the purpose of detecting cancer in vivo. For example, the antibody can be labeled with a positron-emitting nuclide such as $^{15}$F, $^{55}$Co, $^{64}$Cu, $^{66}$Ga, $^{68}$Ga, $^{76}$Br, $^{89}$Zr, and $^{124}$I. A method known in the art (Acta Oncol. 32, 825-830, 1993) can be used in the labeling of the anti-ITM2A antibody with these positron-emitting nuclides.

The anti-ITM2A antibody labeled with the positron-emitting nuclide is administered to humans or animals. Then, radiation emitted by the radionuclide is measured ex vivo using PET (positron emission tomograph). The measurement results are converted to images by a computed tomographic approach. The PET apparatus is intended to noninvasively obtain data about in vivo pharmacokinetics or the like. The PET can quantitatively image radiation intensity indicated by signal intensity. By such use of the PET, antigen molecules highly expressed in particular cancer can be detected without collecting samples from patients. Specifically, in the present invention, the ITM2A protein highly expressed in Ewing's sarcoma or blood cancer such as T cell leukemia, T cell lymphoma, acute myeloid leukemia, B cell tumor, or multiple myeloma can be detected. In the present invention, the ITM2A protein expressed in Ewing's sarcoma having t(11;22)(q24;q12) chromosomal translocation, among the Ewing's sarcoma cells, can be detected. The Ewing's sarcoma, the acute myeloid leukemia, the B cell tumor, the multiple myeloma, or the Ewing's sarcoma having t(11;22)(q24;q12) chromosomal translocation may be any of primary foci and metastatic foci. The anti-ITM2A antibody may be radiolabeled with a short-life nuclide using a positron-emitting nuclide such as $^{11}$C, $^{13}$N, $^{15}$O, $^{18}$F, or $^{45}$Ti, in addition to the nuclides described above. i Research and development have been pursued as to, for example, techniques of producing short-life nuclides using a medical cyclotron and the nuclides described above or producing short-life radiolabeling compounds. The anti-ITM2A antibody can be labeled with various radioisotopes by these techniques. The anti-ITM2A antibody administered to patients accumulates in primary foci and metastatic foci according to the specificity of the anti-ITM2A antibody for pathological tissues at each site. When the anti-ITM2A antibody is labeled with the positron-emitting nuclide, its radioactivity can be detected to detect the presence of the primary foci and the metastatic foci based on the localization of the radioactivity. An active value of gamma radiation or positron emission of 25 to 4000 keV can be appropriately used for the diagnostic use. Moreover, therapeutic effect can also be expected by selecting an appropriate nuclide and administering the selected nuclide in larger amounts. A nuclide that provides a value of gamma radiation or positron emission of 70 to 700 keV can be used for obtaining anticancer effect attributed to radiation.

In an alternative aspect, the present invention provides a method for selecting a test subject to receive the pharmaceutical composition comprising the antibody binding to ITM2A protein as an active ingredient, or a test subject applicable to a method for damaging ITM2A-expressing cells or inhibiting the growth of ITM2A-expressing cells by contacting the ITM2A-expressing cells with the antibody binding to ITM2A protein. In a further alternative aspect, the present invention provides a method for predicting the efficacy of cancer treatment using the anti-ITM2A antibody of the present invention.

As described above, a test subject containing the ITM2A protein expressed in Ewing's sarcoma cells or cells of blood cancer such as T cell leukemia, T cell lymphoma, acute myeloid leukemia, B cell tumor, or multiple myeloma in vivo is preferably selected as a test subject to receive the antibody binding to ITM2A protein or the pharmaceutical composition comprising this antibody as an active ingredient, or as a test subject for which the efficacy of treatment by the administration thereof is predicted. The method of the present invention is not limited by whether or not these tumors or cancers are primary foci or metastatic foci. A test subject having in vivo Ewing's sarcoma having t(11;22)(q24;q12) chromosomal translocation, among the Ewing's sarcomas, may be selected as a preferable subject. Such Ewing's sarcoma having the chromosomal translocation may be any of primary foci and metastatic foci.

The cell damaging method or the method for determining whether or not Ewing's sarcoma cells whose growth is to be inhibited have t(11;22)(q24;q12) chromosomal translocation according to the present invention is as described above.

The present invention also provides a diagnostic drug or kit for cancer diagnosis, comprising a reagent for detecting ITM2A protein in a test sample. The diagnostic drug of the present invention comprises at least the anti-ITM2A antibody.

The reagent for cancer diagnosis of the present invention can be used as a kit for cancer diagnosis, in combination with other factors used in ITM2A detection. Specifically, the present invention relates to a kit for cancer diagnosis which comprises: an antibody binding to ITM2A; and a reagent for detecting the binding of the antibody to ITM2A and may further comprise a control sample consisting of a biological sample containing ITM2A. A manual for instruction of assay procedures may be further included in the kit of the present invention.

An aspect represented by the expression "comprising" used herein encompasses an aspect represented by the expression "essentially consisting of" and an aspect represented by the expression "consisting of".

All prior art documents cited herein are incorporated herein by reference.

EXAMPLES

Hereinafter, the present invention will be described further specifically with reference to Examples. However, the technical scope of the present invention is not limited by these Examples.

Example 1

Expression Analysis of ITM2A mRNA

The expression of ITM2A mRNA was assayed in clinical Ewing's sarcoma samples, Ewing's sarcoma cell lines, blood cancer cell lines, and normal tissues using Human Exon 1.0 ST Array (Affymetrix, Inc.). The expression analysis employed 1 μg of total RNAs from each sample shown in FIGS. 1A-1B. The analysis was conducted according to a method described in GeneChip Whole Transcript (WT) Sense Target Labeling Assay Manual (Affymetrix, Inc.). The data was digitized using Exon Array Computational Tool software (Affymetrix, Inc.). The total RNAs of normal tissues used in the analysis were normal tissues-derived total RNAs purchased from Clontech Laboratories, Inc., Ambion, Inc., Stratagene Corp., Cell Applications, Inc., Panomics, Inc., CHEMICON International, Inc., and BioChain Institute, Inc. Total RNAs were prepared from the tumor sites and normal sites of clinical cancer tissues (sampled after informed consent was obtained) and from cancer cell lines using Trizol (Invitrogen Corp.) or Isogen (Nippon Gene Co., Ltd.) according to methods included in these products. A mean of numeric values obtained with ITM2A core probe sets (probe set IDs: 4013550, 4013551, 4013552, 4013553, 4013554, 4013557, 4013559, 4013560, 4013561, 4013564, and 4013565) was estimated as expression data.

Figure 1B:
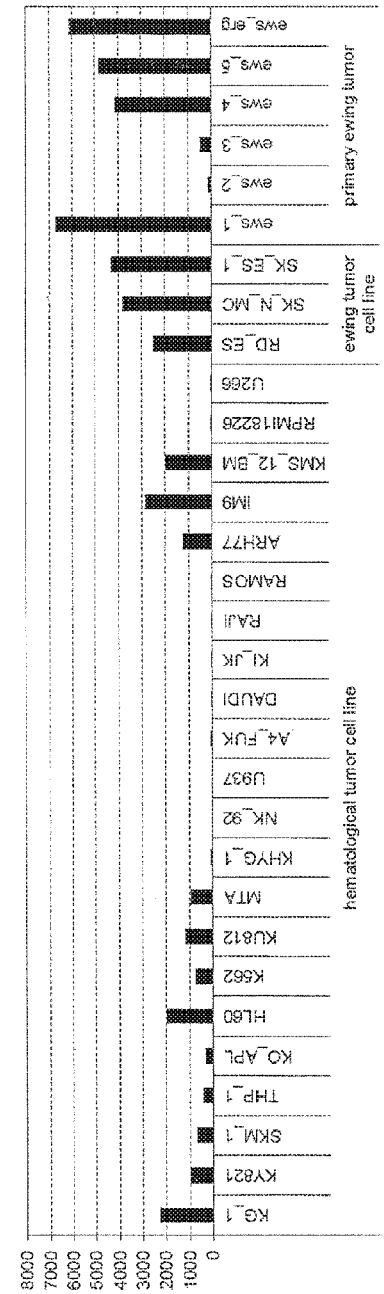

As a result of the expression analysis, the expression level of ITM2A mRNA was around 1000 counts at the maximum in normal tissues, but was 2000 to 7000 counts in cell lines or clinical samples of Ewing's sarcoma, demonstrating the expression of ITM2A in Ewing's sarcoma (FIGS. 1A-1B). Also, the expression of ITM2A was confirmed at a level around 2000 in an acute myeloid leukemia cell line KG-1 or HL60, a B cell tumor cell line IM9, and a multiple myeloma cell line KMS-12-BM. These results showed that ITM2A was able to serve as a therapeutic target and a diagnostic marker for Ewing's sarcoma or blood cancer such as T cell leukemia, T cell lymphoma, acute myeloid leukemia, B cell tumor, or multiple myeloma.

Example 2

Preparation of Monoclonal Antibody Against ITM2A (2-1) Cloning of ITM2A Gene cDNAs were prepared using SuperScript III Reverse Transcriptase (Invitrogen Corp.) with total RNAs prepared from a cancer cell line IM9 using Trizol as a template. A nucleotide sequence encoding ITM2A was amplified by PCR using the cDNAs as a template, a forward primer (SEQ ID NO: 43), and a reverse primer (SEQ ID NO: 44). This PCR employed PrimeSTAR GXL DNA Polymerase (Takara Bio Inc.) and was performed by 30 repetitive reaction cycles each involving 98° C. for 10 seconds, 55° C. for 15 seconds, and 68° C. for 1 minute. The amplification products formed from the PCR were cloned into pCR2.1-TOPO vectors (Invitrogen Corp.) to obtain pCR2.1_ITM2A. The inserted sequence of pCR2.1_ITM2A was sequenced to confirm that the inserted sequence was the same as a sequence registered under RefSeq Accession No. NM_004867.4.

(2-2) Preparation of Expression Vector for DNA Immunization

A nucleotide sequence encoding the extracellular region of ITM2A (predicted to be Tyr75-Glu263 as a result of analysis according to http://www.uniprot.org/) was cloned into expression vectors (pMCN2i) for mammal cells. The vector pMCN2i allows induction of expression of a gene insert under the control of mouse CMV promoter (GenBank Accession No. U68299) and contains a neomycin resistance gene incorporated therein. The signal sequence used was the signal sequence of mouse interleukin 3. First, the ITM2A extracellular region-encoding nucleotide sequence was amplified by PCR using pCR2.1_ITM2A as a template, a forward primer (SEQ ID NO: 45) having SfiI site, and a reverse primer (SEQ ID NO: 46) having NotI site. The amplification products formed from the PCR were cloned into pCR2.1-TOPO vectors. SfiI/NotI-digested fragments of the plasmids obtained as a result of the cloning were cloned into the SfiI-NotI sites of pMCN2i_mIL3ss-mIgG2aFc vectors to obtain plasmids (pMCN2i_mIL3ss-ITM2Aoutside). The pMCN2i_mIL3ss-mIgG2aFc vectors contained the mouse interleukin 3 signal sequence cloned in the EcoRI-SfiI site and the mouse IgG2a antibody Fc region gene cloned in the CpoI-NotI site. The nucleotide sequence from start codon to stop codon in the inserted sequence comprising the ITM2A extracellular region-encoding nucleotide sequence in pMCN2i_mIL3ss-ITM2Aoutside is shown in SEQ ID NO: 47, and an amino acid sequence encoded thereby is shown in SEQ ID NO: 48.

(2-3) Preparation of Protein for Immunization

A fusion protein (ITM2A-Fc) of the ITM2A extracellular region (Tyr75-Glu263) and the Fc region of mouse IgG2a was prepared. First, the ITM2A extracellular region-encoding nucleotide sequence was amplified by PCR using pCR2.1_ITM2A as a template, a forward primer (SEQ ID NO: 49) having SfiI site, and a reverse primer (SEQ ID NO: 50) having CpoI site, and cloned into pCR2.1-TOPO vectors. SfiI/CpoI-digested fragments of the plasmids obtained as a result of the cloning were cloned into the SfiI-CpoI sites of pMCN2i_mIL3ss-mIgG2aFc vectors to obtain plasmids pMCN2i_mIL3ss-ITM2Aoutside-Fc. The nucleotide sequence from start codon to stop codon in the inserted sequence comprising the ITM2A-Fc-encoding nucleotide sequence in pMCN2i_mIL3ss-ITM2Aoutside-Fc is shown in SEQ ID NO: 51, and an amino acid sequence encoded thereby is shown in SEQ ID NO: 52.

Next, pMCN2i_mIL3ss-ITM2Aoutside-Fc digested with PvuI was transduced into a CHO cell line DG44 (Invitrogen Corp.) by electroporation. Transductants were screened for with Geneticin (500 µg/mL) to establish a CHO cell line constantly secreting ITM2A-Fc. The cells were cultured using a CHO-S-SFM II medium (Invitrogen Corp.) supplemented with Geneticin (500 µg/mL), HT Supplement (Invitrogen Corp.), and penicillin/streptomycin (Invitrogen Corp.) as a culture medium. ITM2A-Fc proteins were purified from the culture supernatant of the cells thus established. First, the culture supernatant was applied to a HiTrap rProtein A FF column (GE Healthcare Bio-Sciences Corp.). The column was washed with a binding buffer (20 mM sodium phosphate, pH 7.0), followed by antibody elution with an eluting buffer (0.1 M glycine-HCl, pH 2.7). The buffer solution of the eluate neutralized with a neutralizing buffer (1 M Tris-HCl, pH 9.0) was replaced with PBS using a PD-10 column (GE Healthcare Bio-Sciences Corp.). The protein concentration was measured using DC Protein Assay Kit I (Bio-Rad Laboratories, Inc.).

(2-4) Preparation of Cell Line Forced to Express ITM2A

A nucleotide sequence encoding C-terminally HA-tagged ITM2A was cloned into pMCN2i vectors. First, the ITM2A-encoding nucleotide sequence was amplified by PCR using pCR2.1_ITM2A as a template, a forward primer (SEQ ID NO: 53) having EcoRI site, and a reverse primer (SEQ ID NO: 54) having NotI site and an HA tag sequence, and cloned into pCR2.1-TOPO vectors. EcoRI/NotI-digested fragments of the plasmids obtained as a result of the cloning were cloned into the EcoRI-NotI sites of pMCN2i vectors to obtain plasmids pMCN2i_ITM2A-HA. The nucleotide sequence from start codon to stop codon in the inserted sequence comprising the ITM2A-encoding nucleotide sequence in pMCN2i_ITM2A-HA is shown in SEQ ID NO: 55, and an amino acid sequence encoded thereby is shown in SEQ ID NO: 56. pMCN2i_ITM2A-HA digested with PvuI was transduced into DG44 cells by electroporation. Transductants were screened for with Geneticin (500 µg/mL) to establish a CHO cell line constantly expressing C-terminally HA-tagged ITM2A (ITM2A_CHO).

(2-5) Preparation of Anti-ITM2A Monoclonal Antibody

A Balb/c mouse (female, 8 weeks old, Charles River Laboratories Japan Inc.) was subjected to DNA immunization seven times (days 0, 7, 11, 14, 17, 21, and 24) using Helios Gene Gun (Bio-Rad Laboratories, Inc.). The DNA immunization employed pMCN2i_mIL3ss-ITM2Aoutside. Following the DNA immunization, 50 µg of the ITM2A-Fc proteins mixed with a Freund's incomplete adjuvant (BD Diagnostics) was subcutaneously injected to the mouse (days 49, 91, 99, and 107). At day 115, 50 µg of the ITM2A-Fc proteins was administered to the tail vein without being mixed with an adjuvant. Three days thereafter, the spleen was excised and used as a starting material to prepare hybridomas. First, the excised spleen cells were mixed with a mouse myeloma cell line P3-X63Ag8U1 (P3U1, ATCC) at a ratio of 2:1. PEG1500 (Roche Diagnostics K.K.) was gradually added to the mixed solution to perform cell fusion. An RPMI1640 medium (Invitrogen Corp.) supplemented with penicillin/streptomycin was added to the mixed solution, and the mixture was centrifuged, followed by the removal of the supernatant to remove PEG1500 from the mixed solution. Next, the cells were suspended in a HAT medium (RPMI1640 medium supplemented with 10% fetal bovine serum (FBS), penicillin-streptomycin, 1×HAT Media Supplement (Sigma-Aldrich Corp.), and 0.5×BM-Condimed H1 Hybridoma Cloning Supplement (Roche Diagnostics K.K.)), and the resulting cell suspension was inoculated at a concentration of $1 \times 10^5$ P3U1 cells/well to eight 96-well plates. The plates were incubated at 37° C. for 8 days in a 5% CO2 incubator, followed by screening using the culture supernatant in each well. The screening was performed by assaying binding to the ITM2A_CHO cells and the parent CHO cells using a flow cytometer (FACSCalibur, Becton, Dickinson and Company). Clones producing antibodies specifically binding to the ITM2A_CHO cells were selected and cloned as single clones by the limiting dilution method to isolate hybridomas producing antibodies binding to ITM2A. From these experiments, anti-ITM2A monoclonal antibodies BE5-1, BE6-1, BE7-1-1, and BE13-1 were established.

These antibodies were isotyped using Isostrip (Roche Diagnostics K.K.) and consequently, all determined to be mouse IgG1κ.

The established hybridomas of BE5-1, BE6-1, BE7-1-1, and BE13-1 were each cultured in a HAT medium supplemented with Ultra Low IgG FBS (Invitrogen Corp.) instead of FBS. From each culture supernatant, each anti-ITM2A antibody (BE5-1, BE6-1, BE7-1-1, and BE13-1) was purified using a HiTrap Protein G HP column (GE Healthcare Bio-Sciences Corp.). The concentration of the purified antibody was measured using DC Protein Assay Kit I.

Example 3

Analysis on Epitope for Anti-ITM2A Monoclonal Antibody by ELISA (3-1) Preparation of Partial ITM2A Protein The ITM2A extracellular region (Tyr75-Glu263) or a portion thereof (Tyr75-Lys182) was expressed as a GST-fusion protein in *E. coli* (Tyr75-Glu263: GST-ITM2A-L, and Tyr75-Lys182: GST-ITM2A-S). The fusion protein was C-terminally His-tagged. First, a nucleotide sequence encoding ITM2A (Tyr75-Glu263) or ITM2A (Tyr75-Lys182) was amplified by PCR using pCR2.1_ITM2A as a template, a forward primer (SEQ ID NO: 57) having EcoRI site, and a reverse primer (SEQ ID NO: 58 or 59) having SalI site and a His tag sequence, and cloned into pCR2.1-TOPO vectors. EcoRI/SalI-digested fragments of the plasmids obtained as a result of the cloning were cloned into the EcoRI-SalI sites of pGEX6P-1 vectors (GE Healthcare Bio-Sciences Corp.) to obtain plasmids pGEX_GST-ITM2A-L and pGEX_GST-ITM2A-S, respectively. The nucleotide sequence from start codon to stop codon in pGEX_GST-ITM2A-L is shown in SEQ ID NO: 60, and an amino acid sequence encoded thereby is shown in SEQ ID NO: 61. The nucleotide sequence from start codon to stop codon in the inserted sequence comprising the ITM2A-encoding nucleotide sequence in pGEX_GST-ITM2A-S is shown in SEQ ID NO: 62, and an amino acid sequence encoded thereby is shown in SEQ ID NO: 63.

BL21 (DE3) Competent Cells (Takara Bio Inc.) were transformed with pGEX_GST-ITM2A-L or pGEX_GST-ITM2A-S, and each transformant was induced to express GST-ITM2A-L or GST-ITM2A-S using isopropyl-thiogalactopyranoside. After washing with B-PER (Thermo Fisher Scientific K.K.), cell pellets were solubilized with a solubilizing buffer (8 M urea, 50 mM Tris-HCl (pH 8.0), and 300 mM NaCl). Cell extracts prepared with a solubilizing buffer supplemented with 10 mM imidazole were applied to a HisTrap HP column (GE Healthcare Bio-Sciences Corp.). The column was washed with a solubilizing buffer supplemented with 40 mM imidazole, followed by the elution of GST-ITM2A-L and GST-ITM2A-S using a solubilizing buffer supplemented with 500 mM imidazole. The protein concentrations of GST-ITM2A-L and GST-ITM2A-S were calculated on the basis of absorbance at 280 nm.

(3-2) Analysis on Epitope for Anti-ITM2A Monoclonal Antibody by ELISA

Each anti-ITM2A monoclonal antibody prepared in Example 2 was evaluated for its binding to GST-ITM2A-L and GST-ITM2A-S by ELISA. First, 100 μL each of GST-ITM2A-L and GST-ITM2A-S solutions having a concentration of 3 μg/mL was added to each well of a 96-well plate for ELISA (Nunc-Immuno Plate, Thermo Fisher Scientific K.K.) to coat the well with GST-ITM2A-L or GST-ITM2A-S. The coated well was blocked with a buffer containing 1% bovine serum albumin. Then, 100 μL each of solutions of the antibodies BE5-1, BE6-1, BE7-1-1, and BE13-1 diluted with the same buffer as above was added to each well. The plate was incubated at room temperature for 1 hour. The positive control used was an anti-His antibody (mouse IgG1, Santa Cruz Biotechnology, Inc.). The negative control used was mouse IgG1 (BD Pharmingen). Each antibody was diluted into 8 dilutions at a common ratio of 3.16 from a concentration of 1 μg/mL. After reaction with a secondary antibody (alkaline phosphatase-goat anti-mouse IgG (Gamma), Invitrogen Corp.), a substrate (phosphatase substrate, Sigma-Aldrich Corp.) was added to each well. Color developed by the reaction solution in each well was determined by the measurement of absorbance at 405 nm to 655 nm.

Figure 2A:
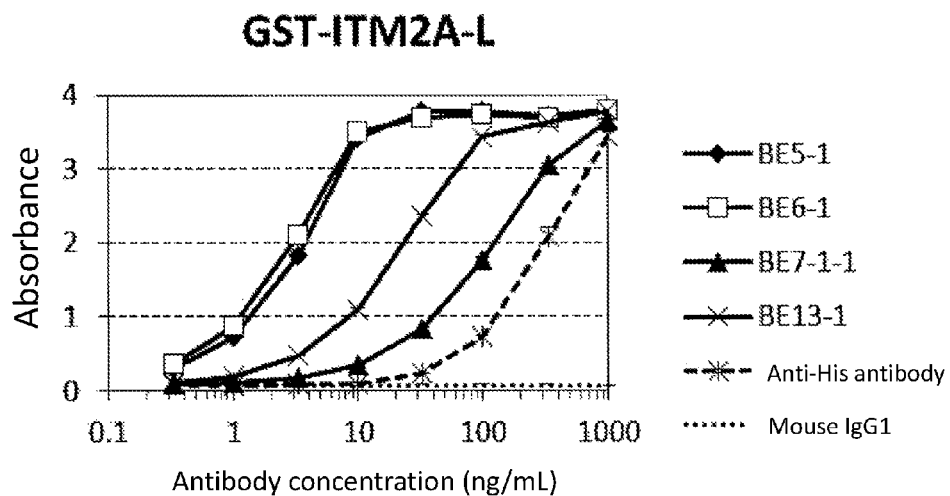
FIGS. 2A-2B show the binding activity of an isolated anti-ITM2A antibody to GST-ITM2A-L and GST-ITM2A-S obtained using ELISA assay.
Figure 2B:
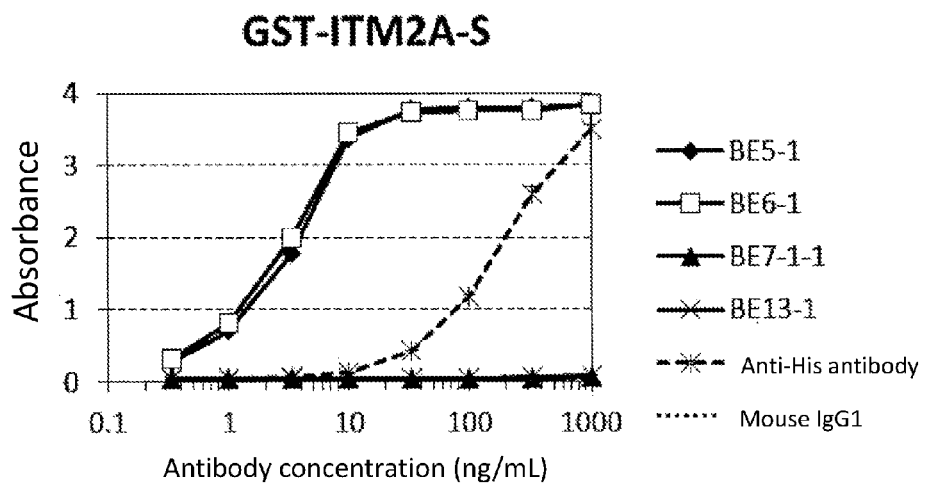

As a result, all the antibodies BE5-1, BE6-1, BE7-1-1, and BE13-1 bound to GST-ITM2A-L, whereas only the antibodies BE5-1 and BE6-1 bound to GST-ITM2A-S (FIGS. 2A-2B). This suggested that the antibodies BE5-1 and BE6-1 recognized ITM2A Tyr75-Lys182 and the antibodies BE7-1-1 and BE13-1 recognized ITM2A Leu183-Glu263.

Example 4

Analysis on Epitope for Anti-ITM2A Monoclonal Antibody by FACS (4-1) Preparation of Cell Line Forced to Express C-Terminally Truncated ITM2A The extracellular region of ITM2A contains a consensus sequence (Arg226-Leu227-Arg228-Arg229) that is cleaved by furin. Thus, a cell line expressing a protein (ITM2A-furin) comprising the sequence from Met1 to Leu227 of ITM2A and an HA tag added downstream thereof was prepared. First, a nucleotide sequence encoding ITM2A (Met1-Leu227) was amplified by PCR using pCR2.1_ITM2A as a template, a forward primer (SEQ ID NO: 53) having EcoRI site, and a reverse primer (SEQ ID NO: 64) having NotI site and an HA tag sequence, and cloned into pCR2.1-TOPO vectors. EcoRI/NotI-digested fragments of the plasmids obtained as a result of the cloning were cloned into the EcoRI-NotI sites of pMCN2i vectors to obtain plasmids pMCN2i_ITM2A-furin-HA. The nucleotide sequence from start codon to stop codon in the inserted sequence comprising the ITM2A-furin-encoding nucleotide sequence in pMCN2i_ITM2A-furin-HA is shown in SEQ ID NO: 65, and an amino acid sequence encoded thereby is shown in SEQ ID NO: 66. pMCN2i_ITM2A-furin-HA digested with PvuI was transduced into DG44 cells by electroporation. Transductants were screened for with Geneticin (500 μg/mL) to establish a CHO cell line (ITM2A-furin_CHO) constantly expressing C-terminally HA-tagged ITM2A-furin.

(4-2) Analysis on Epitope for Anti-ITM2A Monoclonal Antibody by FACS

Each anti-ITM2A monoclonal antibody prepared in Example 2 was assayed for its binding to ITM2A-furin by flow cytometry (FACS). The cells used were ITM2A-furin_CHO prepared in the paragraph (4-1), ITM2A_CHO prepared in the paragraph (2-4), and host cells CHO. These cells were separately suspended in PBS supplemented with 0.2% bovine serum albumin and 0.1% NaN3 (FACS buffer). To each cell suspension, the antibody BE5-1, BE6-1, BE7-1-1, or BE13-1, mouse IgG1, or an anti-HA antibody (clone HA-7, mouse IgG1, Sigma-Aldrich Corp.) was added, and the resulting cell suspension was incubated for 1 hour on ice.

Each antibody was diluted into 6 dilutions at a common ratio of 5 from a concentration of 10 μg/mL. After washing of the cells with a FACS buffer, an FITC-labeled anti-mouse IgG antibody (Goat F(ab')2 Fragment Anti-mouse IgG (Fcγ)-FITC, Beckman Coulter, Inc.) was added thereto as a secondary antibody. The resulting cell suspension was incubated for 1 hour on ice. The cells were washed with a FACS buffer, then suspended in a FACS buffer supplemented with 10 μg/mL propidium iodide (PI, Sigma-Aldrich Corp.), and subjected to assay using a flow cytometer. The assay data was analyzed using CELLQuest software (Becton, Dickinson and Company) to evaluate a PI-negative live cell population.

Figure 3A:
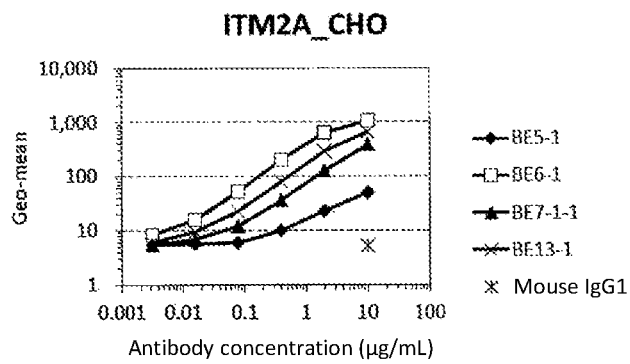
FIGS. 3A-3D show results of examining binding domains of isolated anti-ITM2A antibodies obtained using FACS.
Figure 3B:
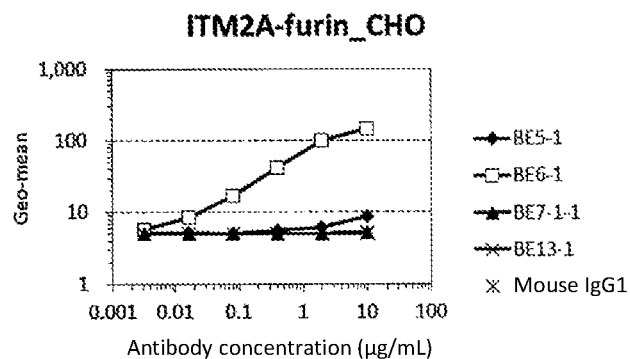
Figure 3C:
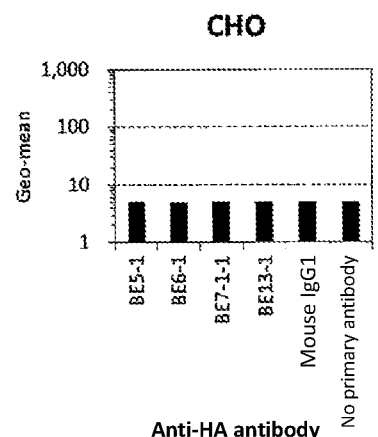
Figure 3D:
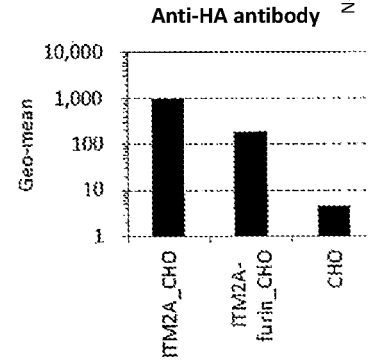

All the antibodies BE5-1, BE6-1, BE7-1-1, and BE13-1 bound to ITM2A_CHO, whereas only the antibodies BE5-1 and BE6-1 bound to ITM2A-furin_CHO (FIGS. 3A and 3B). This suggested that the antibodies BE5-1 and BE6-1 recognized ITM2A Tyr75-Leu227 and the antibodies BE7-1-1 and BE13-1 recognized Arg228-Glu263. None of the antibodies BE5-1, BE6-1, BE7-1-1, and BE13-1 (each 10 μg/mL) bound to host CHO cells (FIG. 3C). The anti-HA antibody (10 μg/mL) was used to confirm the expression of ITM2A or ITM2A-furin in each cell line (FIG. 3D).

Example 5

Analysis on Binding of Anti-ITM2A Monoclonal Antibody to Mouse ITM2A (5-1) Cloning of Mouse ITM2A Gene A nucleotide sequence encoding mouse ITM2A was amplified by PCR using mouse brain cDNA (Mouse MTC Panel I, Clontech Laboratories, Inc.) as a template, a forward primer (SEQ ID NO: 67), and a reverse primer (SEQ ID NO: 68), and cloned into pCR2.1-TOPO vectors to obtain pCR2.1_mITM2A. This PCR employed KOD Plus (Toyobo Co., Ltd.) and was performed by denaturation at 94° C. for 2 minutes followed by 30 repetitive reaction cycles each involving 98° C. for 10 seconds, 59° C. for 30 seconds, and 68° C. for 1 minute. The inserted sequence in pCR2.1_mITM2A was sequenced to confirm that the inserted sequence was the same as a sequence registered under RefSeq Accession No. NM_008409.

(5-2) Preparation of Cell Line Forced to Express Mouse ITM2A

A nucleotide sequence encoding C-terminally HA-tagged mouse ITM2A was cloned into pMCN2i vectors. First, the mouse ITM2A-encoding nucleotide sequence was amplified by PCR using pCR2.1_mITM2A as a template, a forward primer (SEQ ID NO: 69) having EcoRI site, and a reverse primer (SEQ ID NO: 70) having NotI site and an HA tag sequence. The amplified fragments were digested with EcoRI and NotI and cloned into the EcoRI-NotI sites of pMCN2i vectors to obtain plasmids pMCN2i_mITM2A-HA. The nucleotide sequence from start codon to stop codon in the inserted sequence comprising the mouse ITM2A-encoding nucleotide sequence in pMCN2i_mITM2A-HA is shown in SEQ ID NO: 71, and an amino acid sequence encoded thereby is shown in SEQ ID NO: 72. pMCN2i_mITM2A-HA digested with PvuI was transduced into DG44 cells by electroporation. Transductants were screened for with Geneticin (500 μg/mL) to establish a CHO cell line (mITM2A_CHO) constantly expressing C-terminally HA-tagged mouse ITM2A.

(5-3) Analysis on Binding of Anti-ITM2A Monoclonal Antibody to Mouse ITM2A

Each anti-ITM2A monoclonal antibody prepared in Example 2 was evaluated for its binding to mouse ITM2A by FACS. The cells used were ITM2A_CHO prepared in the paragraph (2-4), and mITM2A_CHO prepared in the paragraph (5-2). The binding was detected using FACS in the same way as the procedures described in the paragraph 4-2.

Figure 4A:
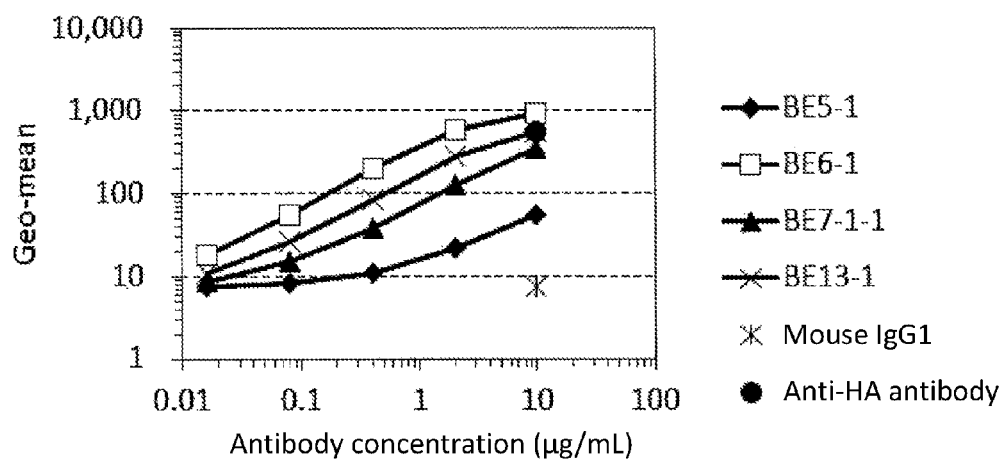
FIGS. 4A-4B show results of examining interspecies cross reactivity of the isolated anti-ITM2A antibodies.
Figure 4B:
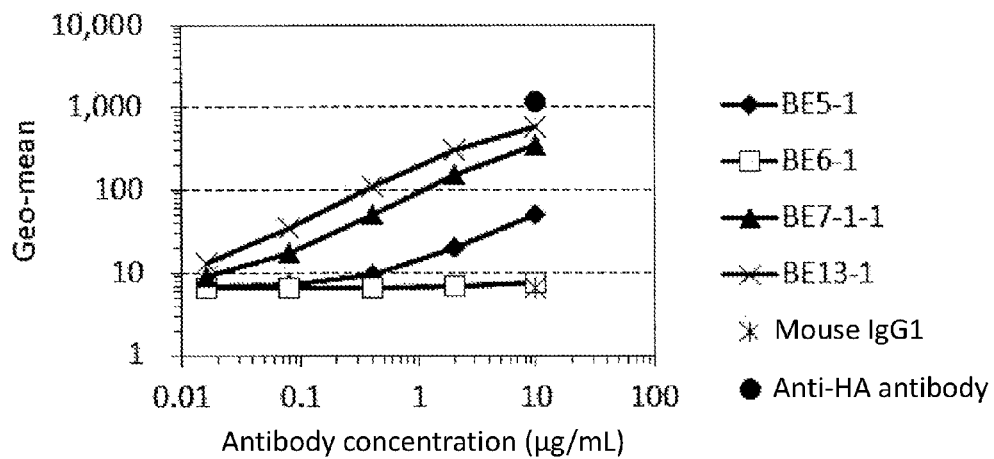
Figure 6A:
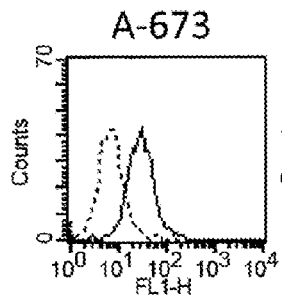
FIGS. 6A-6J show the expression of ITM2A in human cancer cell lines examined using FACS.
Figure 6B:
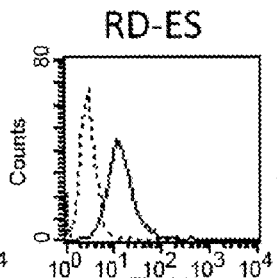
Figure 6C:
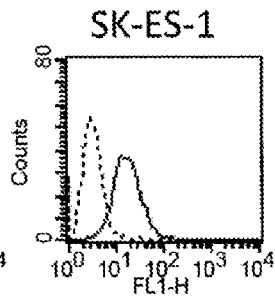
Figure 6D:
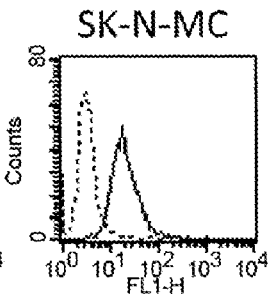
Figure 6E:
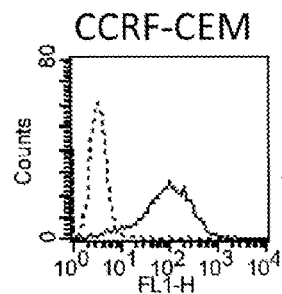
Figure 6F:
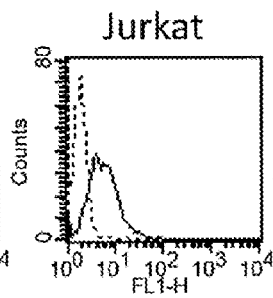
Figure 6G:
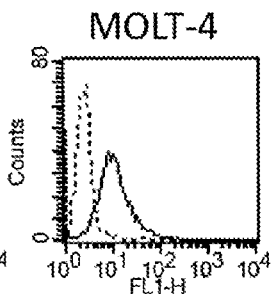
Figure 6H:
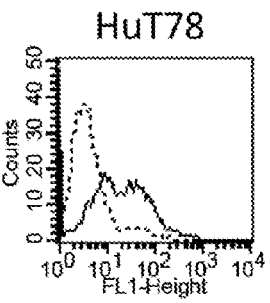
Figure 6I:
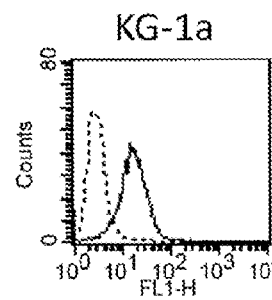
Figure 6J:
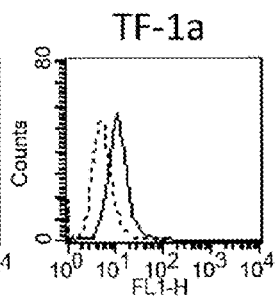
Figure 7A:
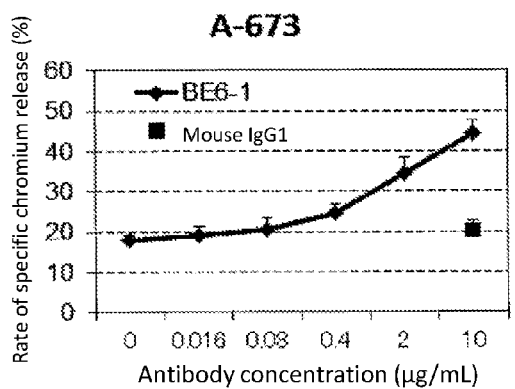
FIGS. 7A-7D show an ADCC activity exerted by an isolated anti-ITM2A antibody against various cancer cell lines.
Figure 7B:
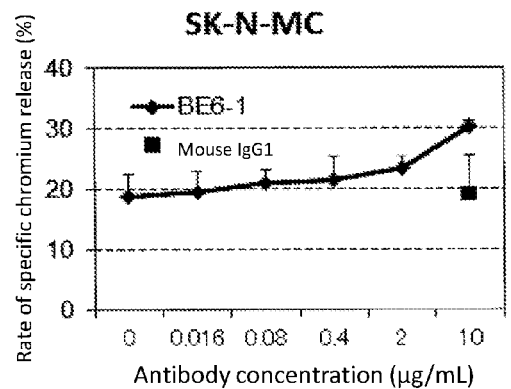
Figure 7C:
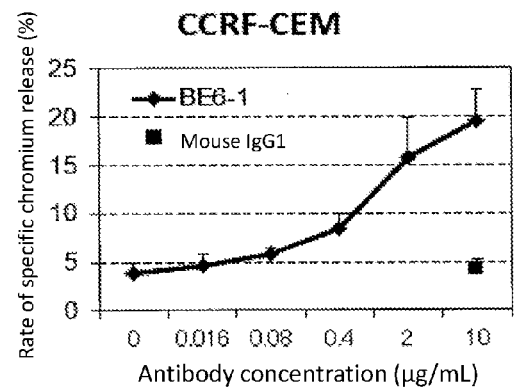
Figure 7D:
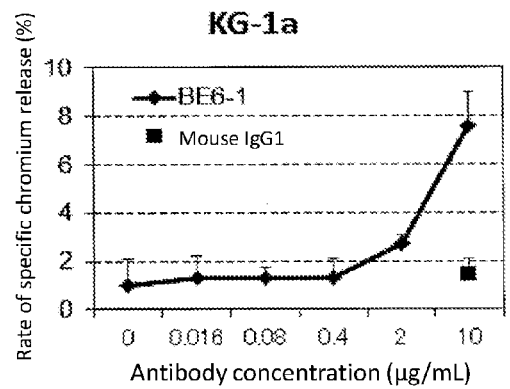

The antibodies BE5-1, BE7-1-1, and BE13-1 bound to mITM2A_CHO, whereas the antibody BE6-1 did not bound thereto (FIGS. 4A-4B). This suggested that the antibodies BE5-1, BE7-1-1, and BE13-1 cross-reacted with mouse ITM2A whereas the antibody BE6-1 did not cross-react therewith.

Example 6

Evaluation of Anti-ITM2A Monoclonal Antibody for its Binding Activity to ITM2A Using Western Blot Each anti-ITM2A monoclonal antibody prepared in Example 2 was evaluated for whether its binding to ITM2A was detectable using Western blot. First, $1 \times 10^7$ cells each of ITM2A_CHO prepared in the paragraph (2-4), ITM2A-furin_CHO prepared in the paragraph (4-1), and host CHO cells were washed with PBS and then lysed using 1 mL of a lysis buffer (50 mM Tris-HCl (pH 7.4), 150 mM NaCl, 1 mM EDTA, 1% Triton X-100, and Protease Inhibitor Cocktail (Sigma-Aldrich Corp.)) to obtain whole cell lysates. Each lysate and 2×Sample Buffer (Sigma-Aldrich Corp.) mixed in equal amounts were heat-treated. Then, 5 μL of each lysate was subjected to SDS-PAGE. After the electrophoresis, proteins, etc. contained in SDS-PAGE gel were transferred to a PVDF membrane (Immobilon-P, Millipore Corp.), which was then incubated at room temperature for 1 hour with 10 μg/mL of the antibody BE5-1, BE6-1, BE7-1-1, or BE13-1, or an anti-HA antibody (clone F-7, Santa Cruz Biotechnology, Inc.). The membrane was incubated at room temperature for 1 hour with an HRP-labeled anti-mouse IgG antibody (GE Healthcare Bio-Sciences Corp.) used as a secondary antibody. Finally, light emitted using ECL Western Blotting Detection Reagents (GE Healthcare Bio-Sciences Corp.) was exposed onto an X-ray film to detect a band representing an antigen-antibody complex.

The Western blot under these conditions showed that only the antibody BE6-1 was able to form an antigen-antibody reaction complex with the antigen ITM2A (FIGS. 5A-5E).

Example 7

Determination of Gene Sequence Encoding Variable Region of Anti-ITM2A Monoclonal Antibody The gene sequences of variable regions of each anti-ITM2A monoclonal antibody prepared in Example 2 were determined. Total RNAs were prepared from hybridomas ($1 \times 10^6$ cells) producing each antibody using RNeasy Mini Kit (Qiagen N.V.). Next, cDNAs were synthesized using Smarter Race cDNA Amplification Kit (Clontech Laboratories, Inc.) with the RNAs as a template. The primers used were a primer (SEQ ID NO: 73) complementary to a nucleotide sequence encoding the heavy chain constant region of a mouse IgG1κ antibody and a primer (SEQ ID NO: 74) complementary to a nucleotide sequence encoding the light chain constant region thereof. The amplification products cloned into pCR2.1-TOPO vectors were sequenced. The variable region sequences of each antibody are summarized in Table 1, and the variable region CDR sequences thereof are summarized in Table 2.

TABLE 1

Sequence of variable region of ITM2A antibody

| Antibody | | SEQ ID NO (nucleotide sequence) | SEQ ID NO (amino acid sequence) |
|---|---|---|---|
| BE5-1 | Heavy chain variable region | 27 | 28 |
| | Light chain variable region | 29 | 30 |
| BE6-1 | Heavy chain variable region | 31 | 32 |
| | Light chain variable region | 33 | 34 |
| BE7-1-1 | Heavy chain variable region | 35 | 36 |
| | Light chain variable region | 37 | 38 |
| BE13-1 | Heavy chain variable region | 39 | 40 |
| | Light chain variable region | 41 | 42 |

TABLE 2

Amino acid sequence of variable region CDR of ITM2A antibody

| Antibody | | | SEQ ID NO (amino acid sequence) |
|---|---|---|---|
| BE5-1 | Heavy chain | CDR1 | 3 |
| | | CDR2 | 4 |
| | | CDR3 | 5 |
| | Light chain | CDR1 | 6 |
| | | CDR2 | 7 |
| | | CDR3 | 8 |
| BE6-1 | Heavy chain | CDR1 | 9 |
| | | CDR2 | 10 |
| | | CDR3 | 11 |
| | Light chain | CDR1 | 12 |
| | | CDR2 | 13 |
| | | CDR3 | 14 |
| BE7-1-1 | Heavy chain | CDR1 | 15 |
| | | CDR2 | 16 |
| | | CDR3 | 17 |
| | Light chain | CDR1 | 18 |
| | | CDR2 | 19 |
| | | CDR3 | 20 |
| BE13-1 | Heavy chain | CDR1 | 21 |
| | | CDR2 | 22 |
| | | CDR3 | 23 |
| | Light chain | CDR1 | 24 |
| | | CDR2 | 25 |
| | | CDR3 | 26 |

Example 8

Analysis on Expression of ITM2A in Human Cancer Cell Line and Evaluation of Anti-ITM2A Monoclonal Antibody for its ADCC Activity and Cell Growth Inhibitory Activity (8-1) Analysis on Expression of ITM2A in Human Cancer Cell Line The expression of ITM2A was assayed in human cancer cell lines by FACS. The antibody used was the antibody BE6-1 having a concentration of 10 μg/mL. The expression of ITM2A was assayed in the same way as the procedures described in Example 4. The secondary antibody used was an FITC-labeled anti-mouse Ig antibody (goat F(ab')2) included in Qifi-Kit (Dako). The negative control used was mouse IgG1 having a concentration of 10 μg/mL. The assay results demonstrated that ITM2A was expressed on the cells of Ewing's sarcoma cell lines (A-673, RD-ES, SK-ES-1, and SK-N-MC), T cell acute lymphocytic leukemia cell lines (CCRF-CEM, Jurkat, and MOLT-4), a T cell lymphoma cell line (HuT78), and acute myeloid leukemia cell lines (KG-1a and TF-1a) (FIGS. 6A-6J).

(8-2) Study on ADCC Activity of Anti-ITM2A Monoclonal Antibody

The antibody-dependent cell-mediated cytotoxicity (ADCC) activity of the antibody BE6-1 was assayed. Human cancer cell lines CCRF-CEM and KG-1a were separately cultured for 1 hour in the presence of chromium-51 (GE Healthcare Bio-Sciences Corp.) and then washed three times with an RPMI1640 medium supplemented with 10% fetal bovine serum and penicillin/streptomycin (hereinafter, referred to as an RPMI medium). Each cell suspension of 1×10$^5$ cells/mL was prepared using the RPMI medium. The cell suspension was added at a concentration of 100 μL/well to a 96-well plate. Next, the antibody BE6-1 or mouse IgG1 was diluted with the RPMI medium and added thereto at a concentration of 50 μL/well. The final concentration of the antibody BE6-1 was adjusted to 10, 2, 0.4, 0.08, and 0.016 μg/mL. The final concentration of the mouse IgG1 was adjusted to 10 μg/mL. The plate was left standing at room temperature for 15 minutes. Then, a cell suspension of effector cells adjusted to 1×10$^6$ cells/mL with the RPMI medium was added thereto at a concentration of 50 μL/well. The effector cells used were NK-92 cells (ATCC) constantly expressing chimeric proteins comprising the extracellular region of mouse Fcγ receptor III (RefSeq Accession No. NM_010188) fused in frame with the transmembrane and intracellular regions of human Fcε receptor I-gamma (RefSeq Accession No. NM_004106) (WO2008093688). The plate was incubated at 37° C. for 4 hours in a 5% CO2 incubator. Then, 100 μL/well of the culture supernatant was recovered, and the radioactivity (cpm) of the culture supernatant was measured using a gamma counter (1480 WIZARD 3", Wallac). The measurement value was applied to the following expression to calculate the rate (%) of specific chromium release:

$$\text{Rate (\%) of specific chromium release} = (A-C) \times 100 / (B-C).$$

In the expression, A represents the radioactivity in each well; B represents a mean of radioactivity values of wells containing cells lysed with 1% (final concentration) Nonidet P-40; and C represents a mean of radioactivity values of wells supplemented with only target cells. The experiment was triplicated to calculate a mean of the rates of specific chromium release and standard deviation.

Human cancer cell lines A-673 and SK-N-MC were inoculated at each concentration of 5×10$^3$ cells/well to a plate (Cellbind surface 96-well cell culture plate (Corning Inc.)). The plate was incubated at 37° C. for 4 days in a 5% CO2 incubator. After addition of chromium-51 to each well, the plate was further incubated for 1 hour. Each well was carefully washed with a medium so as not to dissociate the cells. Then, a medium was added thereto at a concentration of 50 μL/well. Next, the antibody BE6-1 or mouse IgG1 was added thereto at a concentration of 50 μL/well. The final concentration of the antibody BE6-1 was adjusted to 10, 2, 0.4, 0.08, and 0.016 μg/mL. The final concentration of the mouse IgG1 was adjusted to 10 μg/mL. The plate was left standing at room temperature for 15 minutes. Then, effector cells adjusted to 8×10$^5$ cells/mL with a medium were added thereto at a concentration of 100 μL/well. The rate of specific chromium release was calculated according to the expression described above. All the media used were a DMEM medium (Invitrogen Corp.) supplemented with 10% fetal bovine serum and penicillin/streptomycin.

The antibody BE6-1 induced an ADCC activity against the cells A-673, SK-N-MC, CCRF-CEM, and KG-1a in a concentration-dependent manner (FIGS. 7A-7D).

(8-3) Study on Cell Growth Inhibitory Activity of Anti-ITM2A Monoclonal Antibody The cell growth inhibitory activity of the antibody BE6-1 was assayed in the presence of a toxin-conjugated secondary antibody. The toxin-conjugated secondary antibody used was a saporin-labeled anti-mouse IgG antibody (Mab-Zap, Advanced Targeting Systems). A human cancer cell line CCRF-CEM was inoculated at a concentration of 6×10$^3$ cells/well to a 96-well plate. The antibody BE6-1 (500, 100, 20, and 4 ng/mL) or mouse IgG1 (500 ng/mL) was added to each well. Mab-Zap was added at a concentration of 500 ng/mL to each well. The plate was incubated for 3 days. Then, cell growth in each well was assayed using WST-8 (Cell Count Reagent SF, Nacalai Tesque, Inc.). The experiment was triplicated to calculate a mean and standard deviation with cell grown in a well supplemented with only a medium as 0% and cell growth in a well supplemented with only cells as 100%. The medium used was an RPMI1640 medium supplemented with 10% fetal bovine serum and penicillin/streptomycin.

A human cancer cell line HuT78 was inoculated at a concentration of 1×10$^4$ cells/well to a 96-well plate. The antibody BE6-1 (2500, 500, 100, and 20 ng/mL) or mouse IgG1 (2500 ng/mL) was added to each well. Mab-Zap was added at a concentration of 2500 ng/mL to each well. The plate was incubated for 4 days. Then, cell growth in each well was assayed using WST-8. The medium used was an IMDM medium (Invitrogen Corp.) supplemented with 20% fetal bovine serum and penicillin/streptomycin.

A human cancer cell line A-673 was inoculated at a concentration of 3×10$^3$ cells/well to a 96-well plate. The plate was incubated for 1 day. Then, the antibody BE6-1 (1000, 200, 40, and 8 ng/mL) or mouse IgG1 (1000 ng/mL) was added to each well of the plate. Mab-Zap was added at a concentration of 1000 ng/mL to each well. The plate was incubated for 3 days. Then, cell growth in each well was assayed using WST-8. The medium used was a DMEM medium supplemented with 10% fetal bovine serum and penicillin/streptomycin.

Figure 8A:
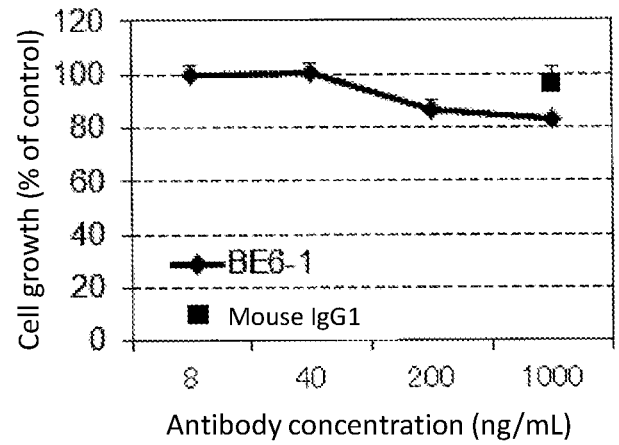
FIGS. 8A-8C show a cytotoxic activity exerted by an isolated anti-ITM2A antibody against various cancer cell lines in the presence of a toxin-conjugated secondary antibody.
Figure 8B:
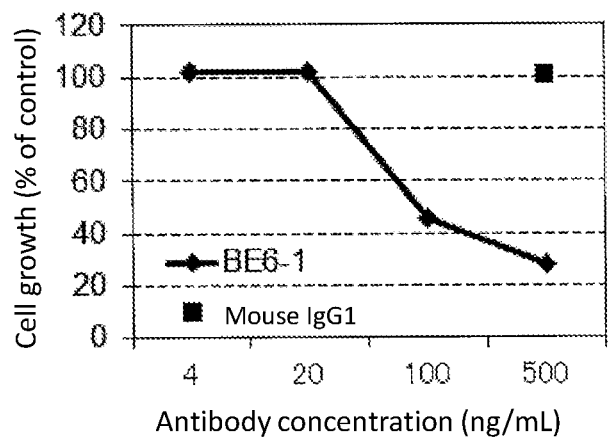
Figure 8C:
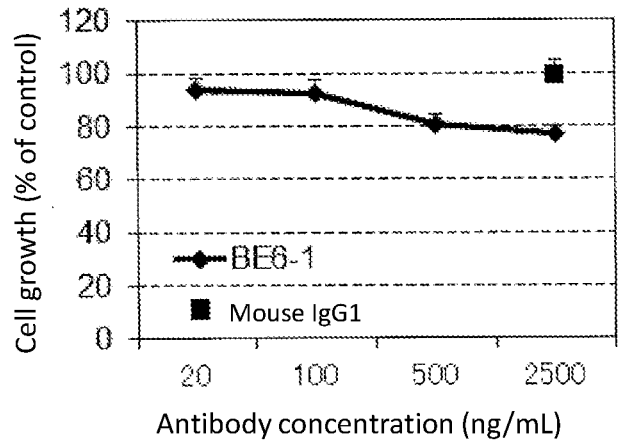

The antibody BE6-1 inhibited cell growth of each cell line in a concentration-dependent manner in the presence of the toxin-conjugated secondary antibody (FIGS. 8A-8C). This suggested that the anti-ITM2A monoclonal antibody directly conjugated with toxin was also able to inhibit the growth of cancer cells.

Example 9

Correlation Between Expression of EWS-FLI1 Fusion Gene and ITM2A (9-1) Expression Analysis of EWS-FLI1 Fusion Gene in Clinical Ewing's Sarcoma Sample 85% of Ewing's sarcoma cases are known to have observable t(11;22)(q24;q12) chromosomal translocation and the expression of a fusion gene (EWS-FLI1) comprising the 5' end of the EWS gene fused with the 3' end of the FLI-1 gene (Cancer Lett (2007) 254, 1-10). Thus, 13 clinical Ewing's sarcoma samples including the samples used in the expression analysis of Example 1 (ews_2, ews_3, ews_4, ews_5, ews_6, ews_7, ews_8, ews_9, ews_10, ews_11, ews_12, ews_13, and ews_15) were analyzed for the expression of the EWS-FLI1 fusion gene by PCR. First, cDNAs were synthesized from the RNAs of each clinical Ewing's sarcoma sample using SuperScript III First-Strand Synthesis System for RT-PCR (Invitrogen Corp.). Next, the EWS-FLI1 fusion gene was amplified by PCR using the cDNAs as a template, a forward primer (SEQ ID NO: 75), and a reverse primer (SEQ ID NO: 76). This amplification employed KOD Plus Version 2 (Toyobo Co., Ltd.) and was performed by thermal denaturation at 94° C. for 2 minutes followed by 30 repetitive cycles each involving 98° C. for 10 seconds and 68° C. for 1.5 minutes. The primer sequences used were the same as those described in the literature (N Engl J Med (1994) 331, 294-9). A nucleotide sequence encoding β-actin was amplified as a control using primers included in the kit (SuperScript III First-Strand Synthesis System for RT-PCR). The amplification reaction using PCR employed KOD Plus Version 2 and was performed by thermal denaturation at 94° C. for 2 minutes followed by 25 repetitive cycles each involving 98° C. for 10 seconds, 58° C. for 30 seconds, and 68° C. for 30 seconds. The positive control used was a Ewing's sarcoma cell line SK-ES-1 expressing the EWS-FLI1 fusion gene. The negative control used was a lymphoma cell line NK-92.

Figure 9A:
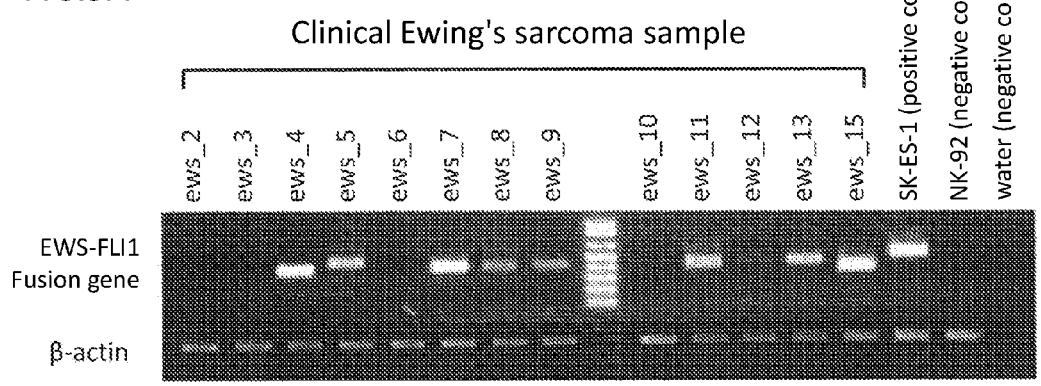
FIGS. 9A-9B show results of evaluating the expression of EWS-FLI1 fusion genes and ITM2A in clinical Ewing's sarcoma samples by PCR.

The PCR results demonstrated the expression of the EWS-FLI1 fusion gene in 9 (ews_4, ews_5, ews_7, ews_8, ews_9, ews_11, ews_12, ews_13, and ews_15) out of the 13 clinical Ewing's sarcoma samples (FIG. 9A).

(9-2) Analysis on Expression of ITM2A in Clinical Ewing's Sarcoma Sample

The expression of the ITM2A gene was analyzed in clinical Ewing's sarcoma samples by PCR. The ITM2A gene was amplified by PCR using the cDNAs synthesized in the paragraph (9-1) as a template, a forward primer (SEQ ID NO: 77), and a reverse primer (SEQ ID NO: 78). This amplification employed KOD Plus Version 2 and was performed by thermal denaturation at 94° C. for 2 minutes followed by 25 repetitive cycles each involving 98° C. for 10 seconds, 65° C. for 30 seconds, and 68° C. for 30 seconds. The positive control used was pCR2.1_ITM2A prepared in the paragraph (2-1). The negative control used was a lymphoma cell line NK-92.

Figure 9B:
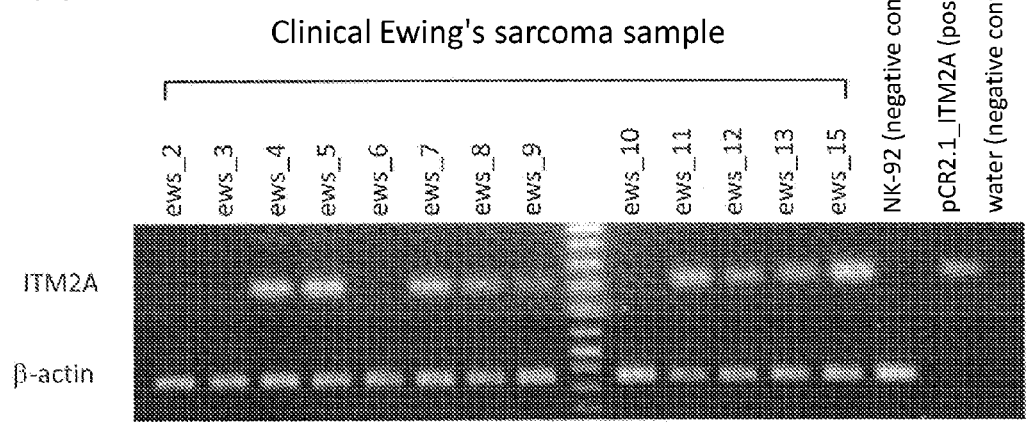

As a result of the PCR, ITM2A was expressed in the 9 cases expressing the EWS-FLI1 fusion gene, demonstrating high correlation between their expression (FIG. 9B).

The invention claimed is:

1. A method for damaging ITM2A-expressing cancer cells, comprising contacting ITM2A-expressing cells with a monoclonal antibody binding to a fragment of an ITM2A protein consisting of amino acids 75 to 263 of SEQ ID NO: 1 by administering the antibody to an animal endogenously having the ITM2A-expressing cells, and damaging the ITM2A-expressing cells with Fcγ receptor-expressing cells as a result of binding of the Fcγ receptor-expressing cells, via the Fcγ receptor, to the Fc domain of the antibody attached to the ITM2A-expressing cells.

2. The method according to claim 1, wherein the cancer cells are Ewing's sarcoma cells.

3. The method according to claim 2, wherein said method further comprises determining that Ewing's sarcoma cells have a chromosomal translocation.

4. The method according to claim 3, wherein the chromosomal translocation is t(11;22)(q24;q12).

5. The method according to claim 1, wherein the cancer cell is a blood cancer cell.

6. The method according to claim 5, wherein the blood cancer is any of T cell leukemia, T cell lymphoma, acute myeloid leukemia, B cell tumor, and multiple myeloma.

7. The method according to claim 1, wherein the antibody binds to a fragment of an ITM2A protein consisting of Tyr75 to Lys182.

8. The method according to claim 1, wherein the antibody binds to a fragment of an ITM2A protein consisting of Arg228 to Glu263.

* * * * *